US008109981B2

(12) United States Patent
Gertner et al.

(10) Patent No.: US 8,109,981 B2
(45) Date of Patent: Feb. 7, 2012

(54) OPTICAL THERAPIES AND DEVICES

(75) Inventors: Michael Gertner, Menlo Park, CA (US); Erica Rogers, Emerald Hills, CA (US)

(73) Assignee: Valam Corporation, New York, NY (US)

( * ) Notice: Subject to any disclaimer, the term of this patent is extended or adjusted under 35 U.S.C. 154(b) by 1610 days.

(21) Appl. No.: 11/152,946

(22) Filed: Jun. 14, 2005

(65) Prior Publication Data

US 2006/0167531 A1 Jul. 27, 2006

Related U.S. Application Data

(60) Provisional application No. 60/646,818, filed on Jan. 25, 2005, provisional application No. 60/661,688, filed on Mar. 14, 2005.

(51) Int. Cl.
*A61N 5/06* (2006.01)
(52) U.S. Cl. .................. 607/88; 607/92; 606/3; 606/13
(58) Field of Classification Search .......... 606/3, 13–17; 607/88–92, 135; 128/898
See application file for complete search history.

(56) References Cited

U.S. PATENT DOCUMENTS

| 1,616,722 A | 2/1927 | Vernon |
| 1,677,016 A | 7/1928 | Berry |
| 1,782,906 A | 11/1930 | Newman |
| 1,800,277 A | 4/1931 | Boerstler |
| 2,227,422 A | 1/1941 | Boerstler |
| 2,992,644 A | 7/1961 | Plantinga et al. |
| 3,416,525 A | 12/1968 | Yeremian |
| 3,706,000 A | 12/1972 | Retzer et al. |
| 3,769,963 A | 11/1973 | Goldman et al. |
| 3,900,034 A | 8/1975 | Katz et al. |
| 3,927,669 A | 12/1975 | Glatt |
| 3,970,856 A | 7/1976 | Mahaffey et al. |
| 3,981,023 A | 9/1976 | King |
| 4,126,130 A | 11/1978 | Cowden et al. |
| 4,207,892 A | 6/1980 | Binder |
| 4,229,658 A | 10/1980 | Gonser |
| 4,233,493 A | 11/1980 | Nath |
| 4,309,617 A | 1/1982 | Long |
| 4,313,431 A | 2/1982 | Frank |
| 4,385,344 A | 5/1983 | Gonser |

(Continued)

FOREIGN PATENT DOCUMENTS

EP 0 435 506 A2 7/1991

(Continued)

OTHER PUBLICATIONS

Asawanonda, P., 2000. 308 nm Excimer Laser for the Treatment of Psoriasis. *Arch Dermatol.* 136: 619-624.

(Continued)

*Primary Examiner* — Ahmed Farah
(74) *Attorney, Agent, or Firm* — K&L Gates

(57) ABSTRACT

An optical therapy device for providing therapeutic light to a person's nasal cavity includes a body and at least one UV light source in or on the body. A distal end of the body is configured to be inserted into the person's nasal cavity. The body can be configured to be hand-held. The optical therapy device is configured such that the UV light source emits a dose of UV light toward tissue in the patient's nasal cavity.

30 Claims, 22 Drawing Sheets

U.S. PATENT DOCUMENTS

| | | |
|---|---|---|
| 4,421,987 A | 12/1983 | Herold |
| 4,444,189 A | 4/1984 | Seiverd |
| 4,450,139 A | 5/1984 | Bussiere et al. |
| 4,561,435 A | 12/1985 | McKnight et al. |
| 4,576,160 A | 3/1986 | Tanaka |
| 4,612,938 A | 9/1986 | Dietrich et al. |
| 4,616,644 A | 10/1986 | Saferstein et al. |
| 4,671,266 A | 6/1987 | Lengyel et al. |
| 4,676,231 A | 6/1987 | Hisazumi et al. |
| 4,686,979 A | 8/1987 | Gruen et al. |
| 4,762,120 A | 8/1988 | Hussein |
| 4,765,322 A | 8/1988 | Charmillot et al. |
| 4,782,819 A | 11/1988 | Adair |
| 4,809,678 A | 3/1989 | Klein |
| 4,842,356 A | 6/1989 | Mori |
| 4,846,172 A | 7/1989 | Berlin |
| 4,861,704 A | 8/1989 | Reemtsma et al. |
| 4,862,886 A | 9/1989 | Clarke |
| 4,899,732 A | 2/1990 | Cohen |
| 4,901,714 A | 2/1990 | Jensen |
| 4,909,254 A | 3/1990 | Wilkinson |
| 4,926,861 A | 5/1990 | Fenyo et al. |
| 4,926,880 A | 5/1990 | Claude et al. |
| 4,930,504 A | 6/1990 | Diamantopoulos et al. |
| 4,946,438 A | 8/1990 | Reemtsma et al. |
| 4,952,369 A | 8/1990 | Belilos |
| 4,998,930 A | 3/1991 | Lundahl |
| 5,013,924 A | 5/1991 | Armstrong et al. |
| 5,053,033 A | 10/1991 | Clarke |
| 5,059,191 A | 10/1991 | Beyer et al. |
| 5,119,461 A | 6/1992 | Beyer et al. |
| 5,146,917 A | 9/1992 | Wagnieres et al. |
| 5,184,044 A | 2/1993 | Thomas |
| 5,239,981 A | 8/1993 | Anapliotis |
| 5,259,380 A | 11/1993 | Mendes et al. |
| 5,260,020 A | 11/1993 | Wilk et al. |
| 5,284,869 A | 2/1994 | Bisaccia et al. |
| 5,292,346 A | 3/1994 | Ceravolo |
| 5,336,209 A | 8/1994 | Porzilli |
| 5,344,433 A | 9/1994 | Talmore |
| 5,363,458 A | 11/1994 | Pan et al. |
| 5,405,368 A | 4/1995 | Eckhouse |
| 5,409,482 A | 4/1995 | Diamantopoulos |
| 5,426,116 A | 6/1995 | Bisaccia et al. |
| 5,439,462 A | 8/1995 | Bille et al. |
| 5,445,608 A * | 8/1995 | Chen et al. ............ 604/20 |
| 5,462,644 A | 10/1995 | Woodson |
| 5,463,250 A | 10/1995 | Nguyen et al. |
| 5,479,543 A | 12/1995 | Black |
| 5,519,534 A | 5/1996 | Smith et al. |
| 5,591,219 A | 1/1997 | Dungan |
| 5,611,793 A | 3/1997 | Wilson et al. |
| 5,616,140 A | 4/1997 | Prescott |
| 5,620,478 A | 4/1997 | Eckhouse |
| 5,626,631 A | 5/1997 | Eckhouse |
| 5,634,711 A | 6/1997 | Kennedy et al. |
| 5,643,253 A | 7/1997 | Baxter et al. |
| 5,671,314 A | 9/1997 | Gregory et al. |
| 5,683,436 A | 11/1997 | Mendes et al. |
| 5,695,448 A | 12/1997 | Kimura et al. |
| 5,704,709 A | 1/1998 | Zwick et al. |
| 5,720,772 A | 2/1998 | Eckhouse |
| 5,728,090 A | 3/1998 | Martin et al. |
| 5,731,589 A | 3/1998 | Sief et al. |
| 5,755,751 A | 5/1998 | Eckhouse |
| 5,773,835 A | 6/1998 | Sinofsky |
| 5,803,729 A | 9/1998 | Tsimerman |
| 5,834,503 A | 11/1998 | Kelly et al. |
| 5,835,648 A | 11/1998 | Narciso, Jr. et al. |
| 5,843,143 A | 12/1998 | Whitehurst |
| 5,855,203 A | 1/1999 | Matter |
| 5,855,595 A | 1/1999 | Fujishima et al. |
| 5,865,829 A | 2/1999 | Kitajima |
| 5,871,522 A | 2/1999 | Sentilles |
| 5,882,328 A | 3/1999 | Levy et al. |
| 5,898,277 A | 4/1999 | Farnsworth et al. |
| 5,913,883 A | 6/1999 | Alexander et al. |
| 5,919,217 A | 7/1999 | Hughes |
| 5,920,075 A | 7/1999 | Whitehead |
| 5,925,034 A | 7/1999 | Buckley et al. |
| 5,947,959 A | 9/1999 | Sinofsky |
| 5,954,679 A | 9/1999 | Baranitsky |
| 5,975,895 A | 11/1999 | Sullivan |
| 5,976,124 A | 11/1999 | Reiser |
| 5,989,283 A | 11/1999 | Wilkens |
| 5,997,571 A | 12/1999 | Farr et al. |
| 5,999,836 A | 12/1999 | Nelson et al. |
| 6,004,438 A | 12/1999 | Woodson |
| 6,013,053 A | 1/2000 | Bower et al. |
| 6,014,489 A | 1/2000 | Johanson |
| 6,027,524 A | 2/2000 | Petit |
| 6,045,575 A | 4/2000 | Rosen et al. |
| 6,053,172 A | 4/2000 | Hovda et al. |
| 6,056,741 A | 5/2000 | Van Saarloos |
| 6,058,937 A | 5/2000 | Doiron et al. |
| 6,071,302 A | 6/2000 | Sinofsky |
| 6,086,558 A | 7/2000 | Bower et al. |
| 6,087,781 A | 7/2000 | Leppelmeier |
| 6,089,740 A | 7/2000 | Forehand et al. |
| 6,096,066 A | 8/2000 | Chen et al. |
| 6,109,268 A | 8/2000 | Thapliyal et al. |
| 6,159,236 A | 12/2000 | Biel |
| 6,168,591 B1 | 1/2001 | Sinofsky |
| 6,170,320 B1 | 1/2001 | Scaringe et al. |
| 6,174,325 B1 | 1/2001 | Eckhouse |
| 6,177,678 B1 | 1/2001 | Brass et al. |
| 6,188,527 B1 | 2/2001 | Bohn |
| 6,201,989 B1 | 3/2001 | Whitehead et al. |
| 6,251,127 B1 | 6/2001 | Biel |
| 6,270,492 B1 | 8/2001 | Sinofsky |
| 6,273,904 B1 | 8/2001 | Chen et al. |
| 6,283,986 B1 | 9/2001 | Johnson |
| 6,284,223 B1 | 9/2001 | Luiken |
| 6,290,496 B1 | 9/2001 | Azar et al. |
| 6,290,713 B1 | 9/2001 | Russell |
| 6,299,860 B1 | 10/2001 | Luiken |
| 6,309,216 B1 | 10/2001 | Parker |
| 6,318,996 B1 | 11/2001 | Melikechi et al. |
| 6,327,897 B1 | 12/2001 | Scaringe et al. |
| 6,328,733 B1 | 12/2001 | Trost |
| 6,331,286 B1 | 12/2001 | Dees et al. |
| 6,343,604 B1 | 2/2002 | Beall |
| 6,345,194 B1 | 2/2002 | Nelson et al. |
| 6,345,215 B1 | 2/2002 | Drechsler |
| 6,355,027 B1 | 3/2002 | Le et al. |
| 6,358,272 B1 | 3/2002 | Wilden |
| 6,362,451 B1 | 3/2002 | Karni et al. |
| 6,364,829 B1 | 4/2002 | Fulghum |
| 6,364,874 B1 | 4/2002 | Bays et al. |
| 6,367,629 B1 | 4/2002 | Bautista et al. |
| 6,373,866 B1 | 4/2002 | Black |
| 6,384,294 B1 | 5/2002 | Levin |
| 6,387,044 B1 | 5/2002 | Tachibana et al. |
| 6,406,474 B1 | 6/2002 | Neuberger et al. |
| 6,409,719 B1 | 6/2002 | Manning |
| 6,413,268 B1 | 7/2002 | Hartman |
| 6,423,055 B1 | 7/2002 | Farr et al. |
| 6,436,127 B1 | 8/2002 | Anderson et al. |
| 6,439,888 B1 | 8/2002 | Boutoussov |
| 6,443,147 B1 | 9/2002 | Matter |
| 6,443,974 B1 | 9/2002 | Oron et al. |
| 6,443,978 B1 | 9/2002 | Zharov |
| 6,447,537 B1 | 9/2002 | Hartman |
| 6,451,010 B1 | 9/2002 | Angeley |
| 6,454,789 B1 | 9/2002 | Chen et al. |
| 6,461,568 B1 | 10/2002 | Eckhardt |
| 6,461,569 B1 | 10/2002 | Boudreaux |
| 6,468,077 B1 | 10/2002 | Melikechi et al. |
| 6,470,888 B1 | 10/2002 | Matter |
| 6,478,730 B1 | 11/2002 | Bala et al. |
| 6,482,004 B1 | 11/2002 | Senn et al. |
| 6,482,201 B1 | 11/2002 | Olsen et al. |
| 6,491,618 B1 | 12/2002 | Ganz |
| 6,491,715 B1 | 12/2002 | Abels et al. |
| 6,494,897 B2 | 12/2002 | Sterman et al. |
| 6,494,899 B1 | 12/2002 | Griffin et al. |
| 6,511,317 B2 | 1/2003 | Melikechi et al. |

| Patent No. | Date | Inventor |
|---|---|---|
| 6,520,957 B1 | 2/2003 | Kasinkas |
| 6,530,919 B1 | 3/2003 | Chodorow et al. |
| 6,532,244 B1 | 3/2003 | Dewey et al. |
| 6,565,803 B1 | 5/2003 | Bolton et al. |
| 6,572,609 B1 | 6/2003 | Farr et al. |
| 6,586,419 B1 | 7/2003 | Crean et al. |
| 6,593,574 B2 | 7/2003 | Thomas et al. |
| 6,626,900 B1 | 9/2003 | Sinofsky et al. |
| 6,641,578 B2 | 11/2003 | Mukai |
| 6,645,230 B2 | 11/2003 | Whitehurst |
| 6,656,112 B2 | 12/2003 | Miyanaga |
| 6,663,659 B2 | 12/2003 | McDaniel |
| 6,679,855 B2 | 1/2004 | Horn et al. |
| 6,692,486 B2 | 2/2004 | Jaafar et al. |
| 6,719,558 B2 | 4/2004 | Cao |
| 6,719,559 B2 | 4/2004 | Cao |
| 6,730,113 B2 | 5/2004 | Eckhardt et al. |
| 6,733,487 B2 | 5/2004 | Keith et al. |
| 6,755,647 B2 | 6/2004 | Melikechi et al. |
| 6,755,648 B2 | 6/2004 | Cao |
| 6,755,649 B2 | 6/2004 | Cao |
| 6,755,849 B1 | 6/2004 | Gowda et al. |
| 6,763,262 B2 | 7/2004 | Hohla et al. |
| 6,764,501 B2 | 7/2004 | Ganz |
| 6,780,010 B2 | 8/2004 | Cao |
| 6,784,366 B1 | 8/2004 | Boucher et al. |
| 6,799,967 B2 | 10/2004 | Cao |
| 6,835,202 B2 | 12/2004 | Harth et al. |
| 6,866,678 B2 | 3/2005 | Shenderova et al. |
| 6,888,319 B2 | 5/2005 | Inochkin et al. |
| 6,890,346 B2 | 5/2005 | Ganz et al. |
| 6,902,397 B2 | 6/2005 | Farrell et al. |
| 6,916,889 B2 | 7/2005 | Rubinsztajn et al. |
| 6,921,929 B2 | 7/2005 | LeBoeuf et al. |
| 6,929,472 B2 | 8/2005 | Cao |
| 6,932,600 B2 | 8/2005 | Cao |
| 6,955,684 B2 | 10/2005 | Savage, Jr. et al. |
| 6,964,662 B2 | 11/2005 | Kidooka |
| 6,967,673 B2 | 11/2005 | Ozawa et al. |
| 6,976,985 B2 | 12/2005 | Altshuler et al. |
| 6,986,782 B2 | 1/2006 | Chen et al. |
| 7,001,413 B2 | 2/2006 | Butler |
| 7,074,233 B1 | 7/2006 | Gowda et al. |
| 7,101,384 B2 | 9/2006 | Benedict |
| 7,107,996 B2 | 9/2006 | Ganz et al. |
| 7,135,034 B2 | 11/2006 | Friedman et al. |
| 7,144,248 B2 | 12/2006 | Irwin |
| 7,201,767 B2 | 4/2007 | Bhullar |
| 7,208,007 B2 | 4/2007 | Nightingale et al. |
| 7,233,115 B2 | 6/2007 | Lys |
| 7,233,831 B2 | 6/2007 | Blackwell |
| 7,241,306 B2 | 7/2007 | Minamoto et al. |
| 7,253,566 B2 | 8/2007 | Lys et al. |
| 7,256,554 B2 | 8/2007 | Lys et al. |
| 2001/0010371 A1 | 8/2001 | Carey et al. |
| 2001/0028943 A1 | 10/2001 | Mashiko et al. |
| 2002/0009275 A1 | 1/2002 | Williams et al. |
| 2002/0029071 A1 | 3/2002 | Whitehurst |
| 2002/0045848 A1 | 4/2002 | Jaafar et al. |
| 2002/0052390 A1 | 5/2002 | Ponikau |
| 2002/0055736 A1 | 5/2002 | Horn et al. |
| 2002/0074559 A1 | 6/2002 | Dowling et al. |
| 2002/0128557 A1 | 9/2002 | Hohla et al. |
| 2002/0128580 A1 | 9/2002 | Carlson et al. |
| 2002/0161282 A1 | 10/2002 | Fulghum |
| 2002/0161418 A1 | 10/2002 | Wilkens et al. |
| 2002/0173833 A1 | 11/2002 | Korman et al. |
| 2002/0183808 A1 | 12/2002 | Biel |
| 2002/0183813 A1 | 12/2002 | Augustine et al. |
| 2002/0187455 A1 | 12/2002 | Melikechi et al. |
| 2003/0009205 A1 | 1/2003 | Biel |
| 2003/0017073 A1 | 1/2003 | Eckhardt et al. |
| 2003/0074034 A1 | 4/2003 | Penner et al. |
| 2003/0091510 A1 | 5/2003 | Ponikau |
| 2003/0143264 A1 | 7/2003 | Margiotta |
| 2003/0153861 A1 | 8/2003 | Royer |
| 2003/0153961 A1 | 8/2003 | Babaev |
| 2003/0163074 A1 | 8/2003 | McGowan et al. |
| 2003/0191459 A1 | 10/2003 | Ganz et al. |
| 2003/0199800 A1 | 10/2003 | Levin |
| 2003/0216795 A1 | 11/2003 | Harth et al. |
| 2003/0217641 A1 | 11/2003 | Palestro et al. |
| 2003/0235800 A1 | 12/2003 | Qadar |
| 2004/0030269 A1 | 2/2004 | Horn et al. |
| 2004/0030368 A1* | 2/2004 | Kemeny et al. ............ 607/88 |
| 2004/0039242 A1 | 2/2004 | Tolkoff et al. |
| 2004/0049144 A1 | 3/2004 | Cea |
| 2004/0059397 A1 | 3/2004 | Sinofsky et al. |
| 2004/0064150 A1 | 4/2004 | Becker |
| 2004/0073278 A1 | 4/2004 | Pachys |
| 2004/0087884 A1 | 5/2004 | Haddock et al. |
| 2004/0111132 A1 | 6/2004 | Shenderova et al. |
| 2004/0120162 A1 | 6/2004 | Tsimerman et al. |
| 2004/0127776 A1 | 7/2004 | Walker et al. |
| 2004/0158302 A1 | 8/2004 | Chornenky et al. |
| 2004/0176823 A1 | 9/2004 | Island et al. |
| 2004/0176824 A1 | 9/2004 | Weckwerth et al. |
| 2004/0186082 A1 | 9/2004 | Hartman |
| 2004/0204747 A1 | 10/2004 | Kemeny et al. |
| 2004/0232339 A1 | 11/2004 | Lanoue |
| 2004/0232359 A1 | 11/2004 | Fiset |
| 2004/0249426 A1 | 12/2004 | Hoenig et al. |
| 2004/0254424 A1 | 12/2004 | Simkulet et al. |
| 2004/0258765 A1 | 12/2004 | Gee |
| 2004/0260161 A1 | 12/2004 | Melker et al. |
| 2004/0260365 A1 | 12/2004 | Groseth et al. |
| 2004/0260367 A1 | 12/2004 | De Taboada et al. |
| 2004/0267236 A1 | 12/2004 | Sun et al. |
| 2005/0010154 A1 | 1/2005 | Wright et al. |
| 2005/0019256 A1 | 1/2005 | Dobkine et al. |
| 2005/0043706 A1 | 2/2005 | Eaton et al. |
| 2005/0077623 A1 | 4/2005 | Roberts et al. |
| 2005/0080465 A1 | 4/2005 | Zelickson et al. |
| 2005/0099824 A1 | 5/2005 | Dowling et al. |
| 2005/0107849 A1 | 5/2005 | Altshuler et al. |
| 2005/0107853 A1* | 5/2005 | Krespi et al. ............ 607/89 |
| 2005/0119643 A1 | 6/2005 | Sobol et al. |
| 2005/0137654 A1 | 6/2005 | Hoenig et al. |
| 2005/0143793 A1 | 6/2005 | Korman et al. |
| 2005/0177208 A1 | 8/2005 | Irwin |
| 2005/0221251 A1 | 10/2005 | Soukos et al. |
| 2005/0228463 A1 | 10/2005 | Mac et al. |
| 2005/0231983 A1 | 10/2005 | Dahm |
| 2005/0240147 A1 | 10/2005 | Makower et al. |
| 2005/0245906 A1 | 11/2005 | Makower et al. |
| 2005/0256553 A1 | 11/2005 | Strisower |
| 2005/0264172 A1 | 12/2005 | Wojnarowski et al. |
| 2005/0267551 A1 | 12/2005 | Bhullar |
| 2005/0287139 A1 | 12/2005 | Ferguson et al. |
| 2006/0004286 A1 | 1/2006 | Chang et al. |
| 2006/0004323 A1 | 1/2006 | Chang et al. |
| 2006/0009821 A1 | 1/2006 | Perez |
| 2006/0047329 A1 | 3/2006 | Krespi et al. |
| 2006/0063973 A1 | 3/2006 | Makower et al. |
| 2006/0095066 A1 | 5/2006 | Chang et al. |
| 2006/0095102 A1 | 5/2006 | Perez |
| 2006/0111760 A1 | 5/2006 | Kemeny et al. |
| 2006/0167532 A1 | 7/2006 | Parker |
| 2006/0196651 A1 | 9/2006 | Board et al. |
| 2006/0200213 A1 | 9/2006 | McDaniel |
| 2006/0206007 A1 | 9/2006 | Bala |
| 2006/0212099 A1 | 9/2006 | Riddell |
| 2006/0214177 A1 | 9/2006 | Jones |
| 2006/0268946 A1 | 11/2006 | Levatter |
| 2006/0276862 A1 | 12/2006 | Irwin |
| 2006/0282028 A1 | 12/2006 | Howard et al. |
| 2006/0293727 A1 | 12/2006 | Spooner et al. |
| 2007/0002582 A1 | 1/2007 | Burwell et al. |
| 2007/0005094 A1 | 1/2007 | Eaton et al. |
| 2007/0014830 A1 | 1/2007 | Tijsma et al. |
| 2007/0032843 A1 | 2/2007 | Hsu et al. |
| 2007/0038117 A1 | 2/2007 | Bala |
| 2007/0049911 A1 | 3/2007 | Brown |
| 2007/0049996 A1 | 3/2007 | Black |
| 2007/0073362 A1 | 3/2007 | Campbell |
| 2007/0073366 A1 | 3/2007 | Porce |
| 2007/0123957 A1 | 5/2007 | Friedman et al. |
| 2007/0135789 A1 | 6/2007 | Chang et al. |

| | | | |
|---|---|---|---|
| 2007/0135874 A1 | 6/2007 | Bala | |
| 2007/0149956 A1 | 6/2007 | Liedel et al. | |
| 2007/0152797 A1 | 7/2007 | Chemel et al. | |
| 2007/0156009 A1 | 7/2007 | Hanlon-Pena et al. | |
| 2007/0156129 A1 | 7/2007 | Kovalcheck | |
| 2007/0156131 A1 | 7/2007 | Datta | |
| 2007/0156132 A1 | 7/2007 | Drysen | |
| 2007/0161882 A1 | 7/2007 | Pappone | |
| 2007/0167666 A1 | 7/2007 | Lubock et al. | |
| 2007/0167667 A1 | 7/2007 | Lubock et al. | |
| 2007/0167999 A1 | 7/2007 | Breden et al. | |
| 2007/0168000 A1 | 7/2007 | Happawana et al. | |
| 2007/0173793 A1 | 7/2007 | Rathjen | |
| 2007/0173804 A1 | 7/2007 | Wham et al. | |
| 2007/0173805 A1 | 7/2007 | Weinberg et al. | |
| 2007/0173806 A1 | 7/2007 | Orszulak et al. | |
| 2007/0179498 A1 | 8/2007 | MacDonald | |
| 2007/0185474 A1 | 8/2007 | Nahen | |
| 2007/0185476 A1 | 8/2007 | Maksimovich | |
| 2007/0185553 A1 | 8/2007 | Kennedy | |
| 2007/0194717 A1 | 8/2007 | Belikov | |
| 2007/0219600 A1 | 9/2007 | Gertner et al. | |
| 2007/0233209 A1 | 10/2007 | Whitehurst | |
| 2007/0239146 A1 | 10/2007 | Wang | |
| 2010/0076526 A1* | 3/2010 | Krespi et al. | 607/88 |

FOREIGN PATENT DOCUMENTS

| | | |
|---|---|---|
| EP | 0435 506 A3 | 8/1991 |
| EP | 0619100 A1 | 2/1994 |
| EP | 0552189 B1 | 3/1995 |
| EP | 0672435 A1 | 9/1995 |
| EP | 0730883 A2 | 9/1996 |
| EP | 0730883 A3 | 2/1999 |
| EP | 1 043 308 A1 | 11/2000 |
| EP | 0817544 B1 | 3/2004 |
| EP | 0724894 B1 | 6/2004 |
| EP | 1051655 B1 | 9/2005 |
| EP | 1736204 A1 | 12/2005 |
| EP | 1719541 A1 | 11/2006 |
| EP | 1797923 A2 | 6/2007 |
| GB | 2 212 010 A | 8/1988 |
| HU | 212060 | 5/1996 |
| JP | 01241557 | 9/1989 |
| RU | 2 045 971 C1 | 10/1995 |
| RU | 2116745 C1 | 8/1998 |
| RU | 1553143 | 3/2001 |
| RU | 2169022 C1 | 6/2001 |
| WO | WO 87/00038 A1 | 1/1987 |
| WO | WO 87/02256 A1 | 4/1987 |
| WO | WO 92/06741 A2 | 4/1992 |
| WO | WO 92/06741 A3 | 8/1992 |
| WO | WO 94/12240 A1 | 6/1994 |
| WO | WO 95/07731 A1 | 3/1995 |
| WO | WO 96/07451 | 3/1996 |
| WO | WO 96/07451 A3 | 5/1996 |
| WO | WO 96/22741 A1 | 8/1996 |
| WO | WO 96/27335 A1 | 9/1996 |
| WO | WO 96/36396 | 11/1996 |
| WO | WO 96/36396 A3 | 1/1997 |
| WO | WO 97/02058 A1 | 1/1997 |
| WO | WO 97/43965 A1 | 11/1997 |
| WO | WO 98/04321 A1 | 2/1998 |
| WO | WO 98/22184 | 5/1998 |
| WO | WO 99/02112 A1 | 1/1999 |
| WO | WO 99/39238 A1 | 8/1999 |
| WO | WO 99/39328 A1 | 8/1999 |
| WO | WO 00/15296 A1 | 3/2000 |
| WO | WO 00/21576 A2 | 4/2000 |
| WO | WO 00/21576 A3 | 7/2000 |
| WO | WO 00/41767 A1 | 7/2000 |
| WO | WO 00/42910 A1 | 7/2000 |
| WO | WO 00/44441 A1 | 8/2000 |
| WO | WO 00/53252 A1 | 9/2000 |
| WO | WO 00/78393 A1 | 12/2000 |
| WO | WO 01/03599 A2 | 1/2001 |
| WO | WO 01/03599 A3 | 5/2001 |
| WO | WO 01/49194 A2 | 7/2001 |
| WO | WO 02/05722 A1 | 1/2002 |
| WO | WO 02/09610 A1 | 2/2002 |
| WO | WO 02/12127 A2 | 2/2002 |
| WO | WO 02/12127 A3 | 2/2002 |
| WO | WO 02/13905 A1 | 2/2002 |
| WO | WO 01/49194 A3 | 5/2002 |
| WO | WO 02/45578 A1 | 6/2002 |
| WO | WO 02/056746 A2 | 7/2002 |
| WO | WO 02/102418 A2 | 12/2002 |
| WO | WO 02/102418 A3 | 12/2002 |
| WO | WO 03/013653 A1 | 2/2003 |
| WO | WO 03/047682 A2 | 6/2003 |
| WO | WO 03/047682 A3 | 12/2003 |
| WO | WO 2004/004562 A1 | 1/2004 |
| WO | WO 2004/004569 A1 | 1/2004 |
| WO | WO 2004/014229 A1 | 2/2004 |
| WO | WO 2004/014486 A1 | 2/2004 |
| WO | WO 2004/026122 A2 | 4/2004 |
| WO | WO 2004/026363 A3 | 5/2004 |
| WO | WO 2004/026122 A3 | 10/2004 |
| WO | WO 2004/096074 A2 | 11/2004 |
| WO | WO 2004/110465 A1 | 12/2004 |
| WO | WO 2005/000389 A2 | 1/2005 |
| WO | WO 2005/008802 A1 | 1/2005 |
| WO | WO 2005/049127 A1 | 6/2005 |
| WO | WO 2005/049131 A1 | 6/2005 |
| WO | WO 2005/058360 A2 | 6/2005 |
| WO | WO 2005/086846 A2 | 9/2005 |
| WO | WO 2005/117755 A2 | 12/2005 |
| WO | WO 2004/096074 A3 | 1/2006 |
| WO | WO 2006/028461 A2 | 3/2006 |
| WO | WO 2006/034008 A2 | 3/2006 |
| WO | WO 2005/058360 A3 | 5/2006 |
| WO | WO 2006/054179 A1 | 5/2006 |
| WO | WO 2006/058062 A2 | 6/2006 |
| WO | WO 2006/074078 A1 | 7/2006 |
| WO | WO 2006/058062 A3 | 11/2006 |
| WO | WO 2006/115761 A1 | 11/2006 |
| WO | WO 2007/008859 A2 | 1/2007 |
| WO | WO 2007/081674 A1 | 7/2007 |
| WO | WO 2007/084608 A2 | 7/2007 |
| WO | WO 2007/090256 A1 | 8/2007 |
| WO | WO 2007/092349 A2 | 8/2007 |
| WO | WO 2007/106339 A2 | 9/2007 |

OTHER PUBLICATIONS

Bionase Nasal Applicator (Web ad).
Bonis, B., et al., 1997. 308 nm UVB excimer laser for psoriasis. *The Lancet* 350:1522.
Csato, M., 1987. Enhancement of Cadida albicans killing activity of separated human epidermal cells by ultraviolet radiation. *British Journal of Dermatology* 116: 469-475.
Csoma, Zsanett 2004. Intranasal irradiation with the xenon chloride ultraviolet B laser improves allergic rhinitis. *Journal of Photochemistry B: Biology* 75: 137-144.
Degitz, K., et al., 1998. Schmalspektrum-UVB 311 nm versus Breitspektrum-UVB. *Der Hautarzt* 49: 795-806.
Folwaczny, M., et al., 1998. Bacterial Action of 308 nm Excimer-Laser Radiation: an In Vitro Investigation. *Journal of Endodontics* 24 (12): 781-785.
Folwaczny, M., et al., 1999. Substance removal on teeth with and without calculus using 308 nm XeCL excimer laser radiation. *J. Clin. Periodontal* 26: 306-312.
Guhl, et al., 2005. Bivalent Effect of UV Light on Human Skin Mast Cells—Low-Level Mediator Release at Baseline but Potent Suppression upon Mast Cell Triggering. *J. Invest. Dermatol.* 124: 453-56.
Hanovia. 1933. Early American Energy Medicine—Part II. Http://www.meridianinstitute.com/eaem/hanovia/hanpart2.html, Aug. 2003 version downloaded from Archive.net May 4, 2006.
Hansen, Jim 2006. High intensity curing lights. *The Orthodontic Cyberjournal* 1-6.
Hollender, A., et al., 1924. The Role of Ultra-Violet Light in the Treatment of Perennial and Seasonal Hay Fever. *The Eye, Ear Nose and Throat Monthly* 327-330.
Hollender, A., et al., 1925. Further Studies in Hay Fever and Asthma with Special Reference to Quartz Ray Therapy. *The Medical Herald and Physiotherapist XLIV*: 153-160.

Howarth, P. et al., 2000. Allergic rhinitis: not purely a histamine-related diesease. *Allergy* 55: 7-16.

International Programme on Chemical Safety. 1994. Ultraviolet Radiation. 256 pages.

Jeckler, J., et al., UVB Phototherapy of Atopic Dermatitis. *British Journal of Dermatology* 119: 697-705.

Joseph, et al., Topical Tacrolimus Ointment for Treatment of Refractory Anterior Segment Inflammatory Disorders. *Cornea* 24 (4): 417-20.

Kemeny, L., et al., 2001. 308-nm Excimer Laser Therapy for Psoriasis. *Arch. Dermatol.* 137: 95-96.

Koreck, A, et al. 2005. Rhinophototherapy: A new therapeutic tool for the management of allergic rhinitis. *Journal of Allergy and Clinical immunology* vol (no) : 1-4.

Krutmann, Jean 2005. Ultraviolet-free phototherapy. *Photodermatology Photoimmunology and Photomedine* 21: 59-61.

Lang, J., 1989. Clinical Anatomy of the Nose, Nasal Cavity, and Paranasal Sinuses. 31-55.

Loo, et al., 2004. Nanoshell-Enabled Photonics-Based Imaging and Therapy of Cancer. *Technol Cancer Res Treat* 3 (1): 33-40.

Neuman, I., et al., 1997. Narrow-band red light phototherapy in perenial allergic rhinitis and nasal polyposis. *Annals of Allergy, Asthma, & Immunology* 78: 399-406.

Novak, Zoltan 2004. Efficacy of Different UV-emitting light sources in the induction of T-cell apoptosis. *Photochemistry and Photobiology* 79 (5): 434-435.

Ozawa, et al., (no date). 312-Nanometer Ultraviolet B (UVB) Light (Narrow-Band UVB) Induces Apoptosis of T Cells within Psoriatic Lesions. *J. Exp. Med.* 189 (4): 711-18.

Perre, et al., 2002. UVB-Activated Psoralen Reduces Luminal Narrowing After Balloon Dilation Because of Inhibition of Constructive Remodeling. *Photochem. Photobiol* 75 (1): 68-75.

Peters, et al., 1997. Dysregulated Proteolytic Balance as the Basis of Excess Extracellular in Fibrotic Disease. *Am. J. Physiol.* Jun, 272 (6 pt 2): R1960-5.

Pin-Ching Maness, et al., 1999. Bacterial Activity of Photocatalytic TiO2 Reaction: toward an Understanding of its Killing Mechanism. *Applied and Environmental Microbiology* 65 (9): 4094-4098.

Plank, T.H., circa 1928. Sinusitis. *The Medical Herald* 220-221.

Reynolds, et al., 2001. Narrow-Band Ultraviolet B and Broad-Band Ultraviolet A Phototherapy in Adult Atopic Eczema: A Randomized Controlled Trial. *Lancet*.357: 2012-16.

Ruxiong, C., et al., 1992. Induction of Cytotoxity by Photoexcited TiO2 Particles. *Cancer Research* 52: 2346-2348.

See, F. and Kompa, A., et al., Fibrosis as a Therapeutic Target Post-Myocardial Infraction. *Curr Pharm Des.* 11 (4): 477-87.

Specification Sheet, Hilltech from Apr. 28, 2006 web page on quartz, short arc lamps; Dec. 2001 web page downloaded from Archive.net May 9, 2006.

Streilein, W. J., et al., 1988. Genetic basis of ultraviolet-B effects on contract hypersensitivity. *Immunogenetics* 27: 252-258.

Szeimes, R., et al., 2002. Photodynamic therapy using topical methyl 5-aminolevulinate compare with cryotherapy for actinic keratosis: a prospective randomized study. *Journal of the American Academy of Dermatology* 47 (2): 258-262.

Tang-Liu, et al., 2005. Ocular Pharmacokinetics and Safety of Cyclosporine, a Novel Treatment for Dry Eye. *Clin Pharmacokinetics* 44 (3): 247-61.

Taube, K.M., et al., 1992. Hochkonzentrierte UV-Bestrahlung kleiner Hautbezirke mit einem neuen puktstrahler-grundlagen und klinische ergebnisse. *Der Deutsche Dermatologe* 10: 1453-1458.

The Eye, Ear, Nose and Throat Monthly. 1925. Physics and Therapeutic Action of Radiant Heat Rays. 38-41.

Gertner, M., et al., U.S. Appl. No. 11/244,812 "Devices, Methods and Kits for Radiation Treatment via a Target Body Surface," filed Oct. 5, 2005.

Gertner, M., et al., U.S. Appl. No. 11/340,824 "Optical Therapy Devices, Systems, Kits and Methods for Providing Therapy to a Body Cavity," filed Jan. 25, 2006.

Gertner, M., et al., U.S. Appl. No. 11/276,787 "Devices, Methods and Kits for Radiation Treatment via a Target Body Surface," filed Mar. 14, 2006.

Arnold, et al. Extracts from "clinical evidence": age related macular degeneration. BMJ. 2000; 321(7263):741-4.

Browning, et al. Treatment of age-related macular degeneration. J R Soc Med. 2004; 97(4):166-9.

Burgess, et al. Histologic changes in porcine eyes treated with high-intensity focused ultrasound. Ann Ophthalmol. 1987; 19(4):133-8.

Eye pharmaceuticals and disease treatments. OptiStock MarketWatch. Access Media Group, LLC; Feb. 2004; (7 pages).

Guidelines for using Verteporfin (VISUDYNE) in photodynamic therapy to treat choroidal neovascularization due to age-related macular degeneration and other causes. Availabe at http://www.gril-leamsler.ch/files/eNerteporfin.pdf. Accessed Dec. 28, 2006. (13 pages).

Peyman, et al. Transpupillary thermotherapy threshold parameters: funduscopic, angiographic, and histologic findings in pigmented and nonpigmented rabbits. Retina. 2003; 23(3):371-7.

Roth, et al. Keypathophysiologic pathways in age-related macular disease. Graefes Arch Chit Exp Ophthalmol. 2004; 242(8):710-6.

Russian Office Action for Application No. 2004104624/14(005059) filed Oct. 24, 2001. (in English).

Schule, et al. Noninvasive optoacoustic temperature determination at the fundus of the eye during laser irradiation. J Biomed Opt. 2004; 9(1):173-9.

SolRx 100 Series Brochure (2 pages). Available at http://www.solarcsystems.com/pdfs/solrx_100_series_home_phototherapy_handheld.pdf. Accessed Jul. 17, 2007.

The Eye Diseases Prevalence Research Group. Prevalence of Age-Related Macular Degeneration in the United States. Arch Ophthalmol. 2004;122:564-572.

Young, et al. Ed. The eye. Special Sense Organs. Weather's Functional Histology. Churchill Livingston, NY. 1993; 376-387.

* cited by examiner

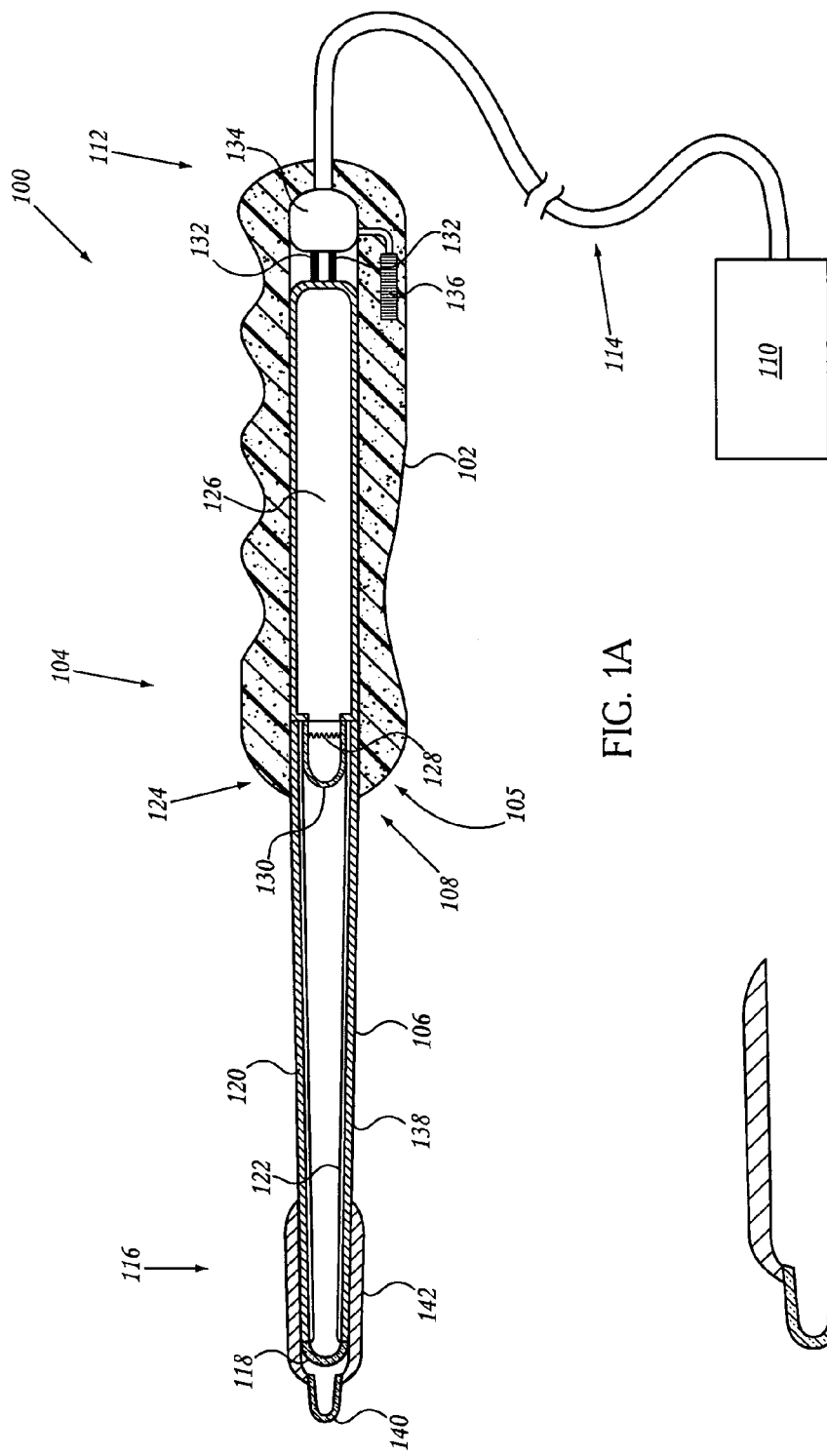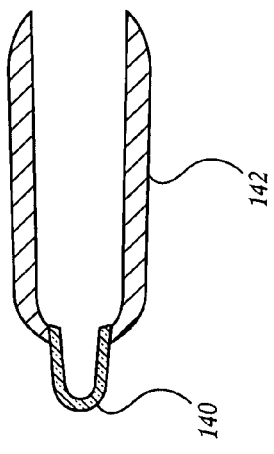
FIG. 1A
FIG. 1B

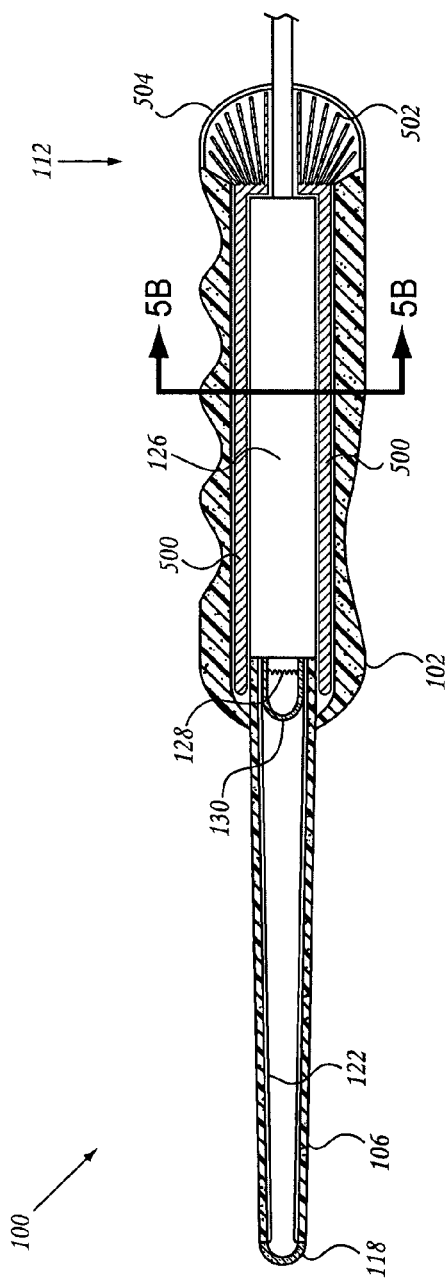
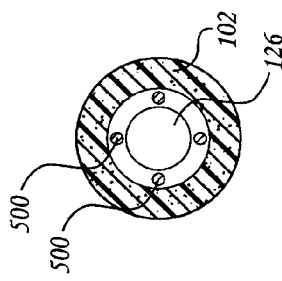
FIG. 5A
FIG. 5B

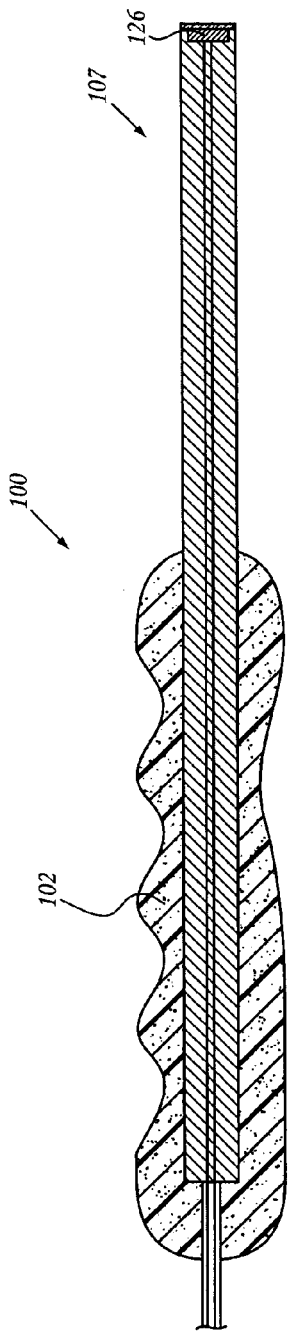
FIG. 11A
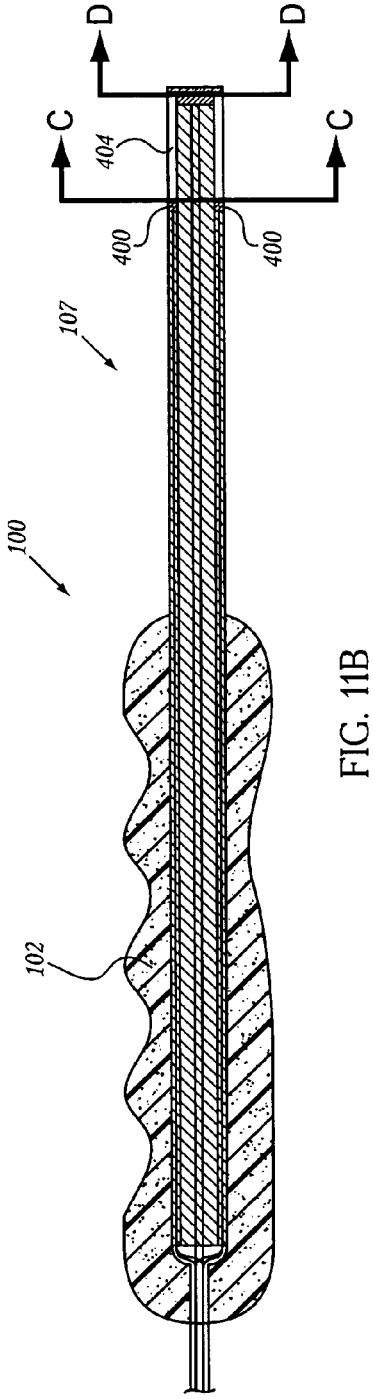
FIG. 11B
FIG. 11D
FIG. 11C

OPTICAL THERAPIES AND DEVICES

CROSS-REFERENCE TO RELATED APPLICATIONS

This application claims the priority benefit of U.S. Provisional Application No. 60/646,818, filed Jan. 25, 2005, and U.S. Provisional Application No. 60/661,688, filed Mar. 14, 2005, both of which are incorporated by reference herein in their entireties.

BACKGROUND

1. Field of the Invention

The present invention relates generally to optical therapies and phototherapies for treatment of diseases and physiological disorders, such as, for example, rhinitis.

2. Background of Invention

Phototherapy has been used to treat skin disorders, such as psoriasis and atopic dermatitis. As the understanding of the pathophysiologic mechanisms of disease has become better understood, it has been learned that psoriasis is mediated by an immune reaction orchestrated by activated T-cells specific for an antigen. It has also been learned that the T cells undergo apoptosis (or programmed cell death) in response to ultraviolet light therapy (see, for example, Ozawa et al, 312-Nanometer Ultraviolet B Light (Narrow-Band UVB) Induces Apoptosis of T Cells within Psoriatic Lesions, 189(4) J. Exp. Med. 711-18, which is incorporated by reference herein). Ultraviolet-B (UVB) light, generally in the range of about 280 nm to about 320 nm, has also been shown to induce cytokines such as interleukin 10 (IL10) and tumor necrosis factor alpha (TNF-α) (see, for example, Narrow-Band Ultraviolet B and Broad-Band Ultraviolet A Phototherapy in Adult Atopic Eczema: A Randomized Controlled Trial, 357 Lancet 2012-16 (2001), which is incorporated by reference herein).

Ultraviolet therapy was also studied in the context of atopic dermatitis and was found to have a beneficial effect (see, for example, Narrow-Band Ultraviolet B and Broad-Band Ultraviolet A Phototherapy in Adult Atopic Eczema: A Randomized Controlled Trial, 357 Lancet 2012-16 (2001) and UVB Phototherapy of Atopic Dermatitis, 119 British Journal of Dermatology 697-705 (1988), both of which are incorporated by reference herein). Similar mechanistic actions of ultraviolet light are invoked in atopic dermatitis as in psoriasis; that is, apoptosis of immune regulatory cells. Additional mechanisms are invoked for atopic dermatitis as well. For example, Guhl, et al., (Bivalent Effect of UV Light on Human Skin Mast Cells—Low-Level Mediator Release at Baseline but Potent Suppression upon Mast Cell Triggering, 124 J. Invest. Dermatol. 453-56 (2005), which is incorporated by reference,) showed that mast cells from skin are sensitive to UVA light having a wavelength in the range of 320 nm to 400 nm, and that these wavelengths (albeit at higher doses) can inhibit the degranulation of mast cells, thereby preventing histamine release.

More recent work in atopic dermatitis has revealed that light concentrated in the blue range (which is generally light having a wavelength in the range of about 400 nm to about 450 nm) can also improve the symptomatology of atopic dermatitis. See, for example, Krutman, et al., Ultraviolet-Free Phototherapy, 21 Photodermatology, Photoimmunology, and Photomedicine 59-61 (2005), which is incorporated by reference. Krutman, et al. showed that the application 40 J/cm$^2$ of essentially blue light can dramatically improve the symptomatology of atopic dermatitis even when one observes patients further out over time.

SUMMARY

In one embodiment, an optical therapy device for providing therapeutic light to a person's nasal cavity comprises a body, wherein at least a distal end of the body is configured to be inserted into the person's nasal cavity and wherein said body is further configured to be hand-held; and at least one UV light source positioned in or on said body, wherein said device is configured such that said at least one UV light source emits a dose of UV light toward tissue in said patient's nasal cavity when the distal end of the body is positioned in the nasal cavity.

The body may further comprise a microcontroller electrically coupled to the at least one UV light source. The at least one UV light source may comprise a solid-state light source, a light emitting diode (LED), at least one of a mercury vapor lamp and a UV enhanced halogen lamp, a UVA light source, a UVB light source, and/or a UVA light source and a UVB light source.

In one embodiment, the optical therapy device further comprises a light conditioner. The light conditioner may comprise a light scattering medium, a light focusing element, a lens, a light reflecting element, a mirror, a filter, an optical filter and/or a sheath.

In another embodiment, the optical therapy device body further comprises a body proximal portion and a body distal portion, wherein the at least one UV light source is located at the body distal portion. In yet another embodiment, the optical therapy device body further comprises a body proximal portion and a body distal portion, the body distal portion comprising the distal end of the body, wherein the at least one UV light source is located at the body proximal portion. The body may be elongate and have a length extending from a proximal end of the body to the distal end, and the length may be less than or equal to about 30 cm.

In another embodiment, the optical therapy device body further comprises a body proximal portion and a body distal portion, the body distal portion comprising the distal end of the body, wherein said optical therapy device further comprises a window, wherein the window is located at or near the body distal portion. The window may be at least partially transmissive of UV light generated by the UV light source.

The optical therapy device may further comprise a sheath, wherein the sheath is configured to at least partially cover the body. The sheath may be manufactured using a mold. In addition, the sheath may comprise at least one material that is at least partially transmissive of UV light. The at least one material may condition the light.

In another embodiment, the optical therapy device further comprises a controller, wherein said controller controls a parameter of the dose. The controller may be in or on said body. The parameter may comprise at least one of an on-time and an off-time of the optical therapy device and/or a sequence for activating said at least one UV light source. The controller may record a total number of doses and prevents the emission of the dose after the total number of doses reaches a predetermined level.

In another embodiment, the optical therapy device further comprises a power supply for powering said at least one UV light source, wherein said power supply is positioned in or on the body. In yet another embodiment, the optical therapy device further comprises a cooling module that dissipates heat generated by said optical therapy device. The cooling module may comprise a heat pipe and/or an active cooling device.

In another embodiment, the optical therapy device further comprises a visible light source. The visible light source may comprise at least one LED.

In another embodiment, the at least one UV light source provides a UVA percentage and a UVB percentage of total optical energy delivered by the optical therapy device, and the UVB percentage is less than said UVA percentage. In another embodiment, the at least one UV light source comprises an LED chipset, wherein the LED chipset comprises at least one UVA LED that emits UVA light and at least one UVB LED that emits UVB light.

In another embodiment, an optical therapy device for providing therapeutic light to a nasal cavity, comprises: a body, wherein at least a portion of the body is configured to be inserted into the nasal cavity; at least one UV light source positioned on or in said body, wherein said at least one UV light source generates light that is emitted toward tissue inside said nasal cavity when the portion of the body is inserted into the nasal cavity; and a light conditioner configured to condition light emitted from the at least one UV light source.

In another embodiment, an optical therapy device for providing therapeutic light to a nasal cavity, comprises: a body, wherein at least a portion of the body is configured to be inserted into the nasal cavity; at least one UV light source positioned on or in said body, wherein said at least one UV light source generates light that is emitted toward tissue inside said nasal cavity; and a sheath, configured to cover at least a portion of the body.

In another embodiment, an optical therapy device for providing therapeutic light to a nasal cavity, comprises: a body, comprising a distal portion, wherein at least the distal portion is configured to be inserted into the nasal cavity; and at least one UV light source that generates UV light, said UV light source positioned at said distal portion.

In another embodiment, an optical therapy device for providing therapeutic light to a nasal cavity, comprises: a body, wherein at least a portion of the body is configured to be inserted into the nasal cavity; and at least one solid-state UV light source positioned in or on said body, wherein said at least one solid-state UV light source is configured to emit light into the nasal cavity when the portion of the body is inserted into the nasal cavity.

In another embodiment, an optical therapy device for providing therapeutic light to a nasal cavity, comprises: an elongate body, wherein at least a distal end of the elongate body is configured to be inserted into the nasal cavity, wherein the elongate body has a length, extending from a proximal end of the body to the distal end, that is less than or equal to about 30 cm; and at least one UV light source positioned in or on said elongate body, wherein said at least one UV light source is configured to emit light into the nasal cavity when the distal end is inserted into the nasal cavity.

In yet another embodiment, an optical therapy device for providing therapeutic light to a person's body cavity, comprises: a body, wherein at least a portion of the body is configured to be inserted into the person's body cavity; at least one UV light source positioned in or on said body, wherein said at least one UV light source is configured to emit light into the person's body cavity; and a light conditioner, configured to condition light emitted from the at least one UV light source.

In another embodiment, an optical therapy device for providing therapeutic light to a person's body cavity, comprises: a body, wherein at least a portion of the body is configured to be inserted into the person's body cavity; at least one UV light source positioned in or on said body, wherein said at least one UV light source is configured to emit light into the person's body cavity; and a sheath, configured to cover at least a portion of the body.

In another embodiment, an optical therapy device for providing therapeutic light to a nasal cavity, comprises: a body, wherein at least a distal portion of the body is configured to be inserted into the nasal cavity; at least one UV light source located at the distal portion, said optical therapy device being configured to activate said at least one UV light source to generate a therapeutic dose of UV light to tissue in the nasal cavity when the portion of the body is positioned in the nasal cavity.

In another embodiment, an optical therapy device for providing therapeutic light to a nasal cavity, comprises: an elongate body, wherein at least a distal end of the elongate body is configured to be inserted into the nasal cavity; and a light conditioner configured to condition light emitted from at least one UV light source located in or on the body, wherein the elongate body has a length, from a proximal end of the body to the distal end, that is less than or equal to about 30 cm.

In another embodiment, an optical therapy device for providing therapeutic light to a nasal cavity, comprises: an elongate body, wherein at least a distal end of the elongate body is configured to be inserted into the nasal cavity; and a sheath, configured to cover at least a portion of the body, wherein the elongate body has a length, from a proximal end of the body to the distal end, that is less than or equal to about 30 cm.

In yet another embodiment, an optical therapy device for providing therapeutic light to a mammal's nasal cavity, the optical therapy device comprises: inserting means for delivering light to the mammal's nasal cavity, said inserting means comprising an insertion portion that is configured to be wholly inserted into the mammal's nasal cavity; and UV light-emission means, positioned on or in said insertion portion of said inserting means, such that said UV light-emission means generates UV light that is emitted toward tissue in said mammal's nasal cavity when the insertion portion is inserted into the patient's nasal cavity.

In another embodiment, a method of delivering optical therapy to a patient, comprises: providing an optical therapy device, said optical therapy device comprising: a body that is configured to be hand-held, said body comprising a distal portion, wherein at least the distal portion is configured to be inserted into the patient's nasal cavity; and at least one UV light source positioned in or on said body; inserting the optical therapy device in the patient's nasal cavity; and emitting UV light for a period of time from said UV light source toward tissue inside said patient's nasal cavity. In another embodiment of the method, the at least one UV light source comprises a light emitting diode.

In another embodiment, a method of delivering optical therapy to a patient, comprises: providing an optical therapy device, said optical therapy device comprising: an elongate body, wherein at least a distal end of the elongate body is configured to be inserted into the person's nasal cavity, and wherein the elongate body has a length, from a proximal end of the body to the distal end, that is less than or equal to about 30 cm; and at least one UV light source located in or on said elongate body; and emitting a dose of UV light from said UV light source toward tissue in said patient's nasal cavity when the distal end of the body is positioned in the nasal cavity. In another embodiment of the method, the at least one UV light source comprises is a light emitting diode.

In one embodiment, an optical therapy device includes a proximal end, a distal end, a connecting structure, and one or more independently controllable light emitting semiconductor devices at the distal end, wherein at least one independently controllable light emitting semiconductor device emits electromagnetic radiation in the range of between about 200 nm and about 400 nm. The device may be further configured for medical use and/or for research use. In one embodiment, at least one of said one or more of the light emitting semiconductor devices emits electromagnetic radiation in the range of between about 250 nm and about 350 nm. In another embodiment, at least one of said one or more of the light emitting semiconductor elements emits electromagnetic radiation in the range of between about 270 nm and about 320 nm. In another embodiment, at least one of said one or more light emitting semiconductor elements emits electromagnetic radiation between about 300 nm and about 315 nm.

In another embodiment, the device also includes a controller configured to modulate the spectral characteristics of the device. At least one light emitting semiconductor devices may emit electromagnetic radiation with more than one individually controllable wavelength. The medical use may be an optical therapy. The device may be configured to enter a body cavity. The electromagnetic radiation of the independently controllable semiconductor device may emit directly into a body cavity. The electromagnetic radiation of the at least one independently controllable semiconductor device may emit electromagnetic radiation into a body cavity without an optical guidance system. The connector of the device can include a rigid and/or a flexible material. In one embodiment, the connector includes a catheter, laparoscope, and/or an endoscope.

In another embodiment of the present invention, an optical therapy device includes a proximal end, a distal end, and a connecting structure between the proximal and distal ends, wherein the distal end includes more than one individually controllable light emitting semiconductor devices. The device may be configured for medical and/or research use, and may further comprise a control system to independently control light emitting semiconductor devices. The device may be configured to apply light therapy to a body surface. The proximal end may be configured to control the orientation of the distal end.

In one embodiment of the present invention, a method of treating a patient includes providing a device having a proximal end, a distal end, and at least one light-emitting semiconductor device at the distal end, and applying the device to a patient such that the distal end resides within 20 mm of a body surface.

In one embodiment of the method, the at least one light-emitting semiconductor device emits electromagnetic radiation with a wavelength in the range of between about 200 nm and about 400 nm. In one embodiment, the body surface is the skin. In another embodiment, the body surface is a mucosal surface of an airway. In yet another embodiment, the mucosal surface of the airway is the nasal mucosa. The mucosal surface may be the mucosa of a paranasal sinus. As used herein. "nasal cavity" includes its ordinary meaning and can also include the paranasal sinuses and nearby anatomic structures. Additionally, the body surface may be a tract created by a man-made device, such as an indwelling catheter. The body surface may be the surface of an implanted device, such as the skin. In one embodiment, a synergistic moiety is introduced into the body surface prior to applying said device.

In one embodiment, a method of treating a patient includes providing a device including a proximal end, a distal end, and at least one semiconductor element at the distal end wherein the at least one semiconductor element or combination of semiconductor elements emit more than one individually controllable wavelength and applying the device to a patient. The method may further include applying the device to the patient to treat or prevent a medical condition. In one embodiment, the medical condition is rhinitis, sinusitis, a disorder of the anterior portion of the eye, a state of infection, an allergic condition, sinusitis, a state of organ rejection, and/or a dermatologic disorder.

In one embodiment, a method of treating a patient includes providing a device having a photon generator, a supply of power, and a mechanism of attachment to the patient, and attaching the device to a patient. The method may further include applying optical therapy to a patient with said device.

In another embodiment, a method of treating a patient includes providing a device having photon generator, a supply of power, a mechanism of attachment to the patient, and a system to control the spectral output of the device, and applying optical therapy to the patient. The method may further include programming said controller to deliver a custom spectral output.

In another embodiment, a method of treating a patient includes providing a device including a semiconductor based photon generator, a supply of power, a mechanism of attachment to the patient, and a system to control the spectral output of the device, and applying optical therapy to the patient.

In one embodiment, a method of treating a patient includes providing a device having at least one semiconductor-based generator of photons that emits light having a wavelength in the range of between about 200 nm and about 400 nm, and a mechanism of attachment to the patient. The method may further include treating a patient with optical therapy.

In one embodiment, a system for delivering optical therapy includes an array of individually controllable light emitting semi-conductor devices, a controller, and a handheld probe, wherein the spectral output of the system is programmable with the controller. The controller may be programmable to deliver one or more doses of optical therapy. The controller may be configured to deliver enough power to destroy said light emitting semiconductor devices after a defined number of optical therapy doses. The system may further include an optical guidance system.

At least one individually controllable semiconductor element may emit electromagnetic radiation having a wavelength in the range of between about 200 nm and about 400 nm. The at least one individually controllable semiconductor device may emit electromagnetic radiation having a wavelength in the range of between about 250 nm and about 350 nm. The system may further include a wireless transmitter in communication with said controller.

BRIEF DESCRIPTION OF THE DRAWINGS

FIG. 1A is a cross-sectional view of an optical therapy device in accordance with one embodiment of the present invention;

FIG. 1B is a cross-sectional view of the sheath of the optical therapy device of FIG. 1A;

FIGS. 4 and 5A are cross-sectional views of optical therapy devices in accordance with embodiments of the present invention;

FIG. 5B is a cross-sectional view taken along line 5B-5B of FIG. 5A;

FIGS. 6A-7A are cross-sectional views of optical therapy device in accordance with additional embodiments of the present invention;

FIGS. 11A and 11B are cross-sectional views of an optical therapy device according to additional embodiments of the present invention;

FIG. 11C is a cross-sectional view taken along line 11C-11C of FIG. 11B;

FIG. 11D is a cross-sectional view taken along line 11D-11D of FIG. 11B;

DETAILED DESCRIPTION OF THE PREFERRED EMBODIMENTS

The Atopic Diseases

Figure 2:
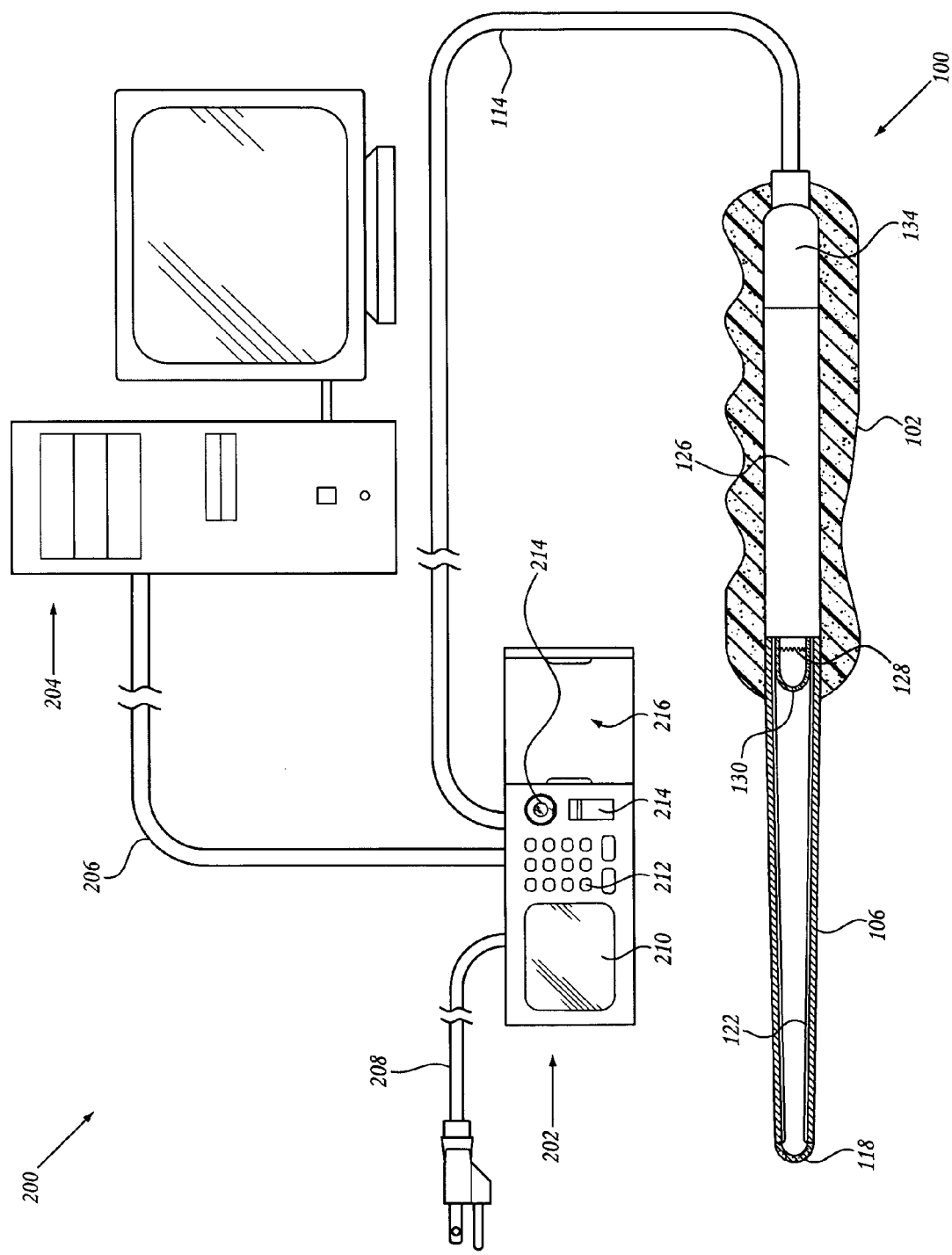
FIG. 2 illustrates an optical therapy system in accordance with another embodiment of the present invention.

Atopy refers to an inherited propensity to respond immunologically to many common, naturally occurring inhaled and ingested allergens with the continual production of IgE antibodies. Allergic rhinitis and asthma are the most common clinical manifestations of atopic disease affecting approximately 50 million people in the United States alone. Atopic dermatitis, or eczema, is less common, but nonetheless afflicts an estimated 20 million people in the U.S. There is a great deal of overlap among patients with atopic disease. Patients with atopic asthma have a greater likelihood of developing allergic rhinitis and dermatitis, and vice versa. Indeed, the pathophysiology for all atopic diseases is generally the same whether or not the affected organ is the skin, the nose, the lungs, or the gastrointestinal tract. Contact with an allergic particle (for example, pollen, cat dander, or food particle) reacts with an associated antibody on the mast cell, which leads to prompt mediator release and clinical symptoms. The IgE antibody response is perpetuated by T cells (antigen specific memory cells or other regulatory cells), which also have specificity for the allergens.

Kemeny, et al., in Intranasal Irradiation with the Xenon Chloride Ultraviolet B Laser Improves Allergic Rhinitis, 75 Journal of Photochemistry and Photobiology B: Biology 137-144 (2004) and Koreck, et al., in Rhinophototherapy: A New Therapeutic Tool for the Management of Allergic Rhinitis, Journal of Allergy and Clinical Immunology (March 2005), both of which are incorporated by reference, describe a treatment for allergic rhinitis using the same theory espoused for the efficacy of ultraviolet light in atopic dermatitis. Their placebo-controlled study showed the efficacy of ultraviolet therapy to treat allergic, or atopic, rhinitis over the course of an allergy season.

Ultraviolet Therapy, Other Skin Disorders, and Other Diseases

Ultraviolet A-1 therapy (typically performed with light having a wavelength in the range of about 340 nm to about 400 nm) has also been shown to be useful in the treatment of disorders of excess collagen production such as scleroderma. In this disease state, the phototherapy has been shown to induce collagenases within the skin which ultimately leads to softer and more compliant skin (See, for example, UVA-1 Phototherapy, 21 Photodermatology, Photoimmunology, and Photomedicine 103-08 (2003), which is incorporated by reference).

Collagenases are also present in other organ systems where scarring is a problem as well. For example, the myocardium is endowed with a very active collagenase system which has been shown to affect the scarring process in disease states such as diastolic heart failure and other cardiomyopathies (See, for example, Fibrosis as a Therapeutic Target Post-Myocardial Infarction, 11(4) Curr Pharm Des. 477-87, which is incorporated by reference). Similarly, interstitial bladder disease also results from imbalances in the collagenase system (Peters, et al., Dysregulated Proteolytic Balance as the Basis of Excess Extracellular in Fibrotic Disease, Am. J. Physiol. Jun, 272 (6 pt 2): R1960-5, which is incorporated by reference).

Antimicrobial Effects of Ultraviolet Light

Infection of a patient takes many forms. Typically, acute bacterial infections are rather easily controlled using standard antibiotic therapies. Chronic infections, on the other hand, are often very difficult to control for several reasons: 1) the antimicrobial flora of chronically infected regions of the body often develop resistance to standard antibiotics due to multiple attempts to treat the flora with antimicrobial therapy; 2) the microbes often form biofilms to protect themselves against the protective mechanisms of the patient; 3) many chronic infections occur around man-made implants which often serve as a nidus for microbes to proliferate as well as form biofilms. Examples of chronic infections include: sinusitis (including chronic bacterial and fungal), vascular access catheter infections, chemotherapy port infections, peritoneal dialysis access catheter infections, vaginal yeast infections, chronic skin ulcerations and wounds, ventriculoperitoneal shunts, sinus tracts in patients with Crohn's disease, chronic bronchitis and COPD, *helicobacter pylori* infections of the stomach, aerobic and anaerobic infections of the small intestine and colon, chronic ear infections, skin ulcers (e.g., diabetic skin ulcers), and fungal infections of the nail beds. There is also increasing evidence that atherosclerosis is caused by infections by micro-organisms such as *Chlamydia*.

It is well-known that ultraviolet light (typically the longer wavelengths of the UVC region of the spectrum, 250-280 nm) has the ability to sterilize and destroy microbes through multifactorial mechanisms. To destroy viruses and bacteria, a dose of 2.5-50 mJ/cm$^2$ can be utilized; for yeast, a dose of 6.6-35.6 mJ/cm$^2$ is typically utilized; and for molds, spores, fungi, and algae, a dose of 1-330 mJ/cm$^2$ is typically utilized.

Lighting Technologies

Advanced lighting technologies, including solid state devices (e.g., light emitting diodes, electroluminescent inorganic materials, organic diodes, etc.), miniature halogen lamps, miniature mercury vapor and fluorescent lamps, collectively offer the potential for less expensive and more flexible phototherapeutical units. Solid state technology has already revolutionized areas outside medicine and holds a great deal of promise inside the biomedical sciences.

Light emitting semiconductor devices (e.g., light emitting diodes or LEDs) offer many advantages in the biomedical sciences. For example, they are generally less expensive than traditional light sources in terms of cost per lumen of light; they are generally smaller, even when providing a similar amount of therapeutic power; they generally offer well-defined and precise control over wavelength and power; they generally allow for control of the pattern of illumination by allowing the placement of discrete optical emitters over a complex surface area and by allowing for individual control of each emitter; they also generally allow for easy integration with other microelectronic sensors (e.g., photodiodes) to achieve low cost integrated components; and finally, solid state components generally permit placement of the light source close to the treatment site rather than relying on costly, inefficient, and unstable optical guidance systems and light sources to do so. Solid state technology also promises portability and patient convenience (e.g., better patient compliance) because the lower cost and improved safety profile of the devices will allow for transfer of the therapies from the physician office and hospital to the patient's home.

Solid state lighting technology has recently advanced to the point where it is useful in the longer wavelength ultraviolet and even more recently in the short ultraviolet wavelengths. For example, S-ET (Columbia, S.C.) manufactures LED dies as well as fully packaged solid state LEDs that emit relatively monochromatic ultraviolet radiation from 240 nm to 365 nm. Similarly, Nichia Corporation (Detroit, Mich.) supplies ultraviolet light emitting diodes which emit relatively monochromatic, non-coherent light in the range 365 nm to 400 nm. White light emitting diodes have been available for a relatively long time and at power densities which rival conventional lighting sources. For example, the LED Light Corporation (Carson City, Nev.) sells high powered white light LEDs with output from 390 nm to 600 nm. Cree Inc. (Durham, N.C.) also produces and sells LED chips in the long wave ultraviolet as well as the blue, amber and red portions of the electromagnetic spectra.

Although some embodiments of the present invention include solid state light sources, other embodiment include non-solid state technologies, such as low pressure lamps, with or without solid state light sources. The Jelight Corporation (Irvine, Calif.) provides customized low pressure mercury vapor lamps complete with phosphors which emit a relatively narrow spectrum depending on the phosphor used. For example, Jelight's 2021 product emits 5 mW in the 305 nm to 310 nm portion of the electromagnetic spectrum.

Halogen lighting technology can also be used to generate ultraviolet light, including light having wavelengths in the UVA (e.g., 320-400 nm), UVB (e.g., 280-320 nm), and white light (e.g., 400-700 nm) portions of the spectrum, as well as relatively narrow-band ultraviolet light (for example, when the lamp is provided with an appropriate filter and/or phosphors). For example, Gilway Technical Lamp (Wolburn, Mass.) supplies quartz halogen lamps, which are enhanced for ultraviolet emission by virtue of the quartz (rather than ultraviolet absorbing glass) bulb covering the filament. Such lamps are generally inexpensive, small, generate minimal heat, and may therefore be incorporated with many of the embodiments of the present invention, as disclosed in greater detail below.

In many embodiments of the present invention, novel methods and devices to treat diseases utilizing optical therapies are disclosed. In addition to novel disease treatments and methods, many embodiments of the present invention are portable, and may be implemented with many of a variety of light sources. In many embodiments, a specific desired illumination pattern and controlling a preferred spectral output may be achieved.

An optical therapy device 100 in accordance with one embodiment of the present invention is illustrated in FIG. 1. The optical therapy device 100 generally includes a body and a light source 126. The term "body" is intended to have its ordinary meaning and can mean any structure of any size or configuration. In one embodiment, the body refers to the optical therapy device 100 without the light source 126 and without the external power supply 110 or power cords 114 connected. The body of the optical therapy device in combination with the light source 126 can be held in one's hand or hands for an extended period of time (e.g., a therapeutic time) without undue effort or discomfort. The body and the light source 126 together can also be held in one's hand or hands and applied to the nasal cavity of a patient without undue effort or discomfort. In one embodiment, where the device is applied to the patient's nasal cavity, the body is not longer than about 30 cm. In another embodiment where the device is applied to the patient's nasal cavity, the body is not longer than about 50 cm. In another embodiment where the device is applied to the patient's nasal cavity, the body is not longer than about 20 cm. The body and the light source 126 should be able to fit into a typically sized briefcase or overnight bag.

The body and light source in some embodiments do not weigh more than about one pound. In other embodiments, the light source and body do not weigh more than about two pounds. And in still other embodiments, the body and light source do not weigh more than about three pounds. When a cord 114 is attached, the device and computer 110 are attached (e.g., the optical therapy system), the body and light source continue to be held in one's hand or hands. Optical therapy device 100 can have a handpiece 102 that in one embodiment has a contoured surface for right-handed or left-handed gripping by a user. The distal end 104 of the handpiece 102 can be coupled to a tube 106 at the tube's proximal end 108; in one embodiment, the tube 106 is adapted to transport light. The proximal end 112 of the handpiece 102 can also be coupled to a power supply 110. A power coupling 114 can couple the handpiece 102 to the power supply 110.

The tube 106 is, in one embodiment generally shaped and sized to be inserted through the nostril of a patient and into the patient's nasal cavity. The nasal cavity is used herein to refer to the region of the nose from the nares to the nasopharynx and includes the paranasal sinuses and the nasal septum. For insertion into the nostril of a patient, the diameter of the distal end of the device body 116 is generally not larger than about 1 cm. In some embodiments, the diameter of the distal end of the device body 116 is not larger than about 5 mm. In other embodiments, the diameter of the distal end of the device body 116 is not larger than about 3 mm. In one embodiment, the tube 106 has a tapered shape, and tapers from a large diameter at its proximal end 108 to a smaller diameter (e.g., about 1 cm) at its distal end 116. The diameter at the proximal end 108 can be chosen for the ergonomic comfort of the person holding the device. In some embodiments, the diameter of the proximal end 108 is in the range of from about 1 cm to about 5 cm. The proximal end can also be contoured as a hand grip for a right or left-handed user. The distal end 116 has additional features which can control the illumination pattern. Additional features and embodiments of the tube 106 and its distal end 116 are provided in greater detail below.

In one embodiment, the tube 106 includes a tip 118 at the distal end 116 of the tube 106. The tip 118 of the tube 106 is any of a variety of optically transparent or partially transparent structures. The term "optically transparent" is intended to have its ordinary meaning, and to also mean transparent to wavelengths between about 250 nm and about 800 nm. In some cases, optically transparent can refer to more narrow ranges of transparency. For example, "optically transparent to ultraviolet light" can refer to transparency in the range from about 200 nm to 400 nm; "optically transparent to ultraviolet B" can refer to transparency in the range from about 280 nm to about 320 nm.

In one embodiment, the tip 118 includes a window, a diffusing lens, a focusing lens, an optical filter, or a combination of one or more of such tip types or other tip types which allow the spectral output to be conditioned. The terms conditioning, conditioner, and the like refer to their ordinary meaning, as well as a modification of the spectral output or the geometric illumination pattern of the device. In one embodiment, to provide a desired output spectrum, three types of tips are used in series within the tube 106. For example, in one embodiment, a lens is used to diffuse (e.g., refract) certain wavelengths while filtering (e.g., transmitting certain wavelengths and absorbing others) certain wavelengths, and serving as a window (e.g., transmitting) certain wavelengths. In another embodiment, the light from the tube 106 is transferred through tip 118 through a series of internal reflections. In one embodiment, the tip 118 is made at least in part from a different material than that of the tube 106. The tip 118 of the tube 106 may be shaped or designed to disperse light as it exits the reflecting tube 106 and is transmitted to a patient.

In some embodiments, tube 106 can be a reflecting tube and can be manufactured from any of a variety of materials, including plastic, stainless steel, nickel titanium, glass, quartz, aluminum, rubber, lucite, or any other suitable material known to those of skill in the art that may be adapted to be place inside of a patient's body. In some embodiments, the material of the tube is chosen to reflect certain wavelengths and/or absorb others. In some embodiments, the tube is configured to yield near or total internal reflection.

In one embodiment, the reflecting tube 106 is hollow. The inside wall 120 of the reflecting tube 106 at least partially reflects light of a selected wavelength. The inside wall 120 may include a reflecting layer 122 applied over its entire surface although in other embodiments the inside wall 120 does not include a reflecting layer 122. In one embodiment, the reflective layer 122 includes a coating of a reflecting material such as, for example, aluminum, silica carbide, or other suitably reflective material.

The proximal end 108 of the tube 106 is coupled to the distal end 105 of the handpiece 102 by any of a variety of couplings 124 well known to those of skill in the art. For example, in one embodiment, the coupling 124 includes a press-fit connection, a threaded connection, a weld, a quick-connect, a screw, an adhesive, or any other suitable coupling as is known to those of skill in the art. Coupling 124 includes mechanical, optical, and electrical couplings, as well as combinations thereof.

In one embodiment, the coupling 124 is releasable so that the tube 106 may be decoupled or removed from the handpiece 102. Such coupling 124 may also be made from a disposable material. In another embodiment, the reflecting tube 106 is permanently attached to the handpiece 102. In such case, the coupling 124 is a permanent connection.

In one embodiment, the handpiece 102 of the body includes a light source 126. The light source may be any of a variety of high, low, or medium pressure light emitting devices such as for example, a bulb, an emitter, a light emitting diode (LED), a xenon lamp, a quartz halogen lamp, a standard halogen lamp, a tungsten filament lamp, or a double bore capillary tube, such as a mercury vapor lamp with or without a phosphor coating. The particular light source selected will vary depending upon the desired optical spectrum and the desired clinical results, as will be described in greater detail below. Although the light source 126 of FIG. 1 is shown in the handpiece 102, the light source 126 can be placed anywhere on, in, or along the optical therapy device 100. In some of the embodiments discussed below, multiple light sources are placed within the optical therapy device 100, some of which may reside in the handpiece 102 and some of which may reside on or in the tube 106, and some of which may reside on or in the tip 118.

In one embodiment, the light source 126 includes a phosphor-coated, low pressure mercury vapor lamp. In a related embodiment, the phosphor is placed distal to the mercury vapor lamp; for example, the phosphor is coated onto the reflecting tube 106 or is incorporated into the tip 118. Optical emitter 128 illustrates the light emitting portion of the light source 126. In one embodiment, optical emitter 128 is a filament. Such filaments may be used when light source 126 is an incandescent or halogen lamp. When light source 126 is a mercury vapor lamp, optical emitter 128 can be an inner capillary tube where the mercury plasma emits photons. Leads 132 extending from the light source 126, electrically couple the light source 126 with a control circuit 134. In one embodiment, the control circuit 134 is in electrical communication with a controller 136 and with power supply 110 via the power coupling 114.

In some embodiments, it is desired to control variables or control parameters associated with the output of the optical therapy device 100. Examples of such variables include power, timing, frequency, duty cycle, spectral output, and illumination pattern. In one embodiment, the control circuit 134 controls the delivery of power from the power supply 110 to the light source 126 according to the activation or status of the controller 136. For example, in one embodiment, the control circuit 134 includes a relay, or a transistor, and the controller 136 includes a button, or a switch. When the button or switch of the controller 136 is pressed or activated, power from the power supply 110 is able to flow through the control circuit 134 to the light source 126.

The variables can be controlled in response to, for example, at least one photoreflectance parameter, which, for example, may be measured or obtained at the distal end 116 of the therapy device 100. Other variables or control parameters include a desired dosage, or a previous dosage. In some embodiments, the patient or treating physician can adjust the treatment time based on the prior history with the optical therapy device 100. In some embodiments, controller mechanisms, which can be integral to the optical therapy device 100, allow for control over dosage and illumination. In other embodiments, the controller tracks the total dose delivered to a patient over a period of time (e.g., days to months to years) and can prohibit the device from delivering additional doses after the preset dosage is achieved.

Although the control circuit 134 is illustrated within the handpiece 102 of the optical therapy device 100, in another embodiment, the control circuit 134 is located within the power supply 110. In such embodiments, the controller 136 communicates with the control circuit 134 through the power coupling 114. Control data, commands, or other information may be provided between the power supply 110 and the handpiece 102 as desired. In one embodiment, control circuit 134 stores information and data, and can be coupled with another computer or computing device.

In one embodiment, power from the power supply 110 flows to the control circuit 134 of the handpiece 102 through a power coupling 114. The power coupling 114 may be any of a variety of devices known to those of skill in the art suitable for providing electrical communication between two components. For example, in one embodiment, the power coupling 114 includes a wire, a radio frequency (RF) link, or a cable.

The light source 126 is generally adapted to emit light with at least some wavelengths in the ultraviolet spectrum, including the portions of the ultraviolet spectrum known to those of skill in the art as the UVA (or UV-A), $UVA_1$, $UVA_2$, the UVB (or UV-B) and the UVC (or UV-C) portions. In another embodiment of the current invention, light source 126 emits light in the visible spectrum in combination with ultraviolet light or by itself. Finally, in yet another embodiment, the light source 126 emits light within the infrared spectrum, in combination with white light and/or ultraviolet light, or by itself. Light source 126 may be adapted to emit light in more than one spectrum simultaneously (with various phosphors, for example) or a multiplicity of light sources may be provided to generate more than one spectrum simultaneously. For example, in one embodiment, the light source 126 emits light in the UVA, UVB, and visible spectra. Light emission at these spectra can be characterized as broad- or narrow-band emission. In one embodiment, narrow-band is over a bandgap of about 10-20 nm and broad-band is over a bandgap of about 20-50 nm.

In other embodiments, the spectrum is continuous. Continuous (or substantially continuous) emission is intended to have its ordinary meaning, and also to refer to generally smooth uniform optical output from about 320-400 nm for UVA, 280-320 nm for UVB, and below about 280 nm for UVC. In other embodiments, the light source 126 emits light in any two of the foregoing spectra and/or spectra portions. In addition, in some embodiments, some portions of the spectra are smooth and others are continuous.

For example, in one embodiment, the light source 126 emits light having a narrow-band wavelength of approximately 308 nm within the UVB portion of the UV spectrum. In another embodiment, the light source 126 emits light having a wavelength below approximately 300 nm. In other embodiments, the light source 126 emits light having a wavelength between about 254 nm and about 313 nm.

In one embodiment, the optical therapy device 100 includes more than one light source 126, where each light source 126 has an output centered at a different wavelength. Each light source 126 can have an output that can be characterized as broad-band, narrow-band, or substantially single band. All light sources 126 can be the same characterization, or may have one or more different characterizations. For example, in one embodiment, the optical therapy device 100 includes three light sources 126: one that emits light in the UVA region of the UV spectrum, one that emits light in the UVB region of the UV spectrum, and one that emits light in the visible region of the optical spectrum.

The light sources may each emit light at a different energy or optical power level, or at the same level. The optical therapy device 100 may be configured to provide light from three light sources 126, each having a different relative output energy and/or relative energy density level (e.g., fluence). For example, in one embodiment, the optical energy emitted from the light source 126 that provides light in the UVA region of the UV spectrum is about 10%, 20%, 25%, 35%, between about 15% and about 35%, or at least about 20% of the optical energy and/or fluence provided by the optical therapy device 100. In one embodiment, the optical energy emitted from the light source 126 that provides light in the UVB region of the UV spectrum is about 1%, 3%, 5%, 8%, 10%, between about 1% and about 11%, or at least about 2% of the optical energy and/or fluence provided by the optical therapy device 100. In one embodiment, the optical energy emitted from the light source 126 that provides light in the visible region of the optical spectrum is about 50%, 60%, 75%, 85%, between about 60% and about 90%, or at least about 65% of the optical energy and/or fluence provided by the optical therapy device 100.

In one embodiment, the optical therapy device 100 includes a UVA light source 126, a UVB light source 126, and a visible light source 126, where the UVA light source 126 provides about 25%, the UVB light source provides about 5%, and the visible light source provides about 70% of the optical energy and/or fluence provided by the optical therapy device 100. For example, in one embodiment, the optical therapy device 100 provides a dose to the surface it is illuminating (e.g., the nasal mucosa) of about 2 $J/cm^2$, where the UVA light source 126 provides about 0.5 $J/cm^2$, the UVB light source 126 provides about 0.1 $J/cm^2$, and the visible light source 126 provides about 1.4 $J/cm^2$. In another embodiment, the optical therapy device 100 provides a dose of about 4 $J/cm^2$, where the UVA light source 126 provides about 1 $J/cm^2$, the UVB light source 126 provides about 0.2 $j/cm^2$, and the visible light source 126 provides about 2.8 $j/cm^2$. In another embodiment, the optical therapy device 100 provides a dose of about 6 $j/cm^2$, where the UVA light source 126 provides about 1.5 $J/cm^2$, the UVB light source 126 provides about 0.3 $J/cm^2$, and the visible light source 126 provides about 4.2 $J/cm^2$. In yet another embodiment, the optical therapy device 100 provides a dose of about 8 $J/cm^2$, where the UVA light source 126 provides about 2 $J/cm^2$, the UVB light source 126 provides about 0.4 $j/cm^2$, and the visible light source 126 provides about 5.6 $j/cm^2$. In some embodiments, the white light is omitted from the therapy leaving only the doses of the ultraviolet light. In some embodiments, the white light and the UVA are omitted leaving only the UVB doses. In other embodiments, the UVB and the white light are omitted leaving only the UVA dose. In other embodiments the UVB dosage is concentrated in the range from 305 nm to 320 nm, sometimes referred to as $UVB_1$. $UVB_1$ can be used in place of UVB in any of the combinations and doses above. In other embodiments, $UVA_1$ (e.g., 340-400 nm) is used in any of the embodiments above in place of UVA. In yet other embodiments, $UVA_2$ (e.g., 320-340 nm) is used in the embodiments above in place of UVA. In some embodiments, blue light (e.g., 400-450 mm) or a combination of blue light and long wavelength UVA (e.g., 375-450 nm) is used to treat tissue. In some embodiments, the dose of blue light or combination UVA-blue light is about 20-100 times greater than UVB. In some embodiments, the fluence in the above measurements represents energy delivered to a body cavity. For example, when the body cavity is the nasal cavity, the area over which the light is delivered can be approximately 5-30 cm$^2$; therefore the energy in each region of the optical spectrum leaving the optical therapy device is in some embodiments 5-30 times the energy reaching the surface of the body cavity.

In some embodiments, a ratio is defined between the wavelengths. In one embodiment, the ratio between the total UVA power and the total UVB power (the power ratio) is about 5:1. In other embodiments, the ratio is between 5 and 10:1. In other embodiments, the ratio is between 10 and 15:1. In some embodiments, $UVB_1$ is substituted in the defined ratios. In any of the above ratios, visible light can be excluded or included. In some embodiments, the power ratio is further defined between $UVA_1$ and $UVB_1$; for example, the power ratio can be from 40:1 to 80:1 for a ration of $UVA_1$ to $UVB_1$.

Optical energy densities are generally derived from a power density applied over a period of time. Various energy densities are desired depending on the disorder being treated and may also depend on the light source used to achieve the optical output. For example, in some embodiments, the energy densities are achieved over a period of time of about 0.5 to 3 minutes, or from about 0.1 to 1 minute, or from about 2 to 5 minutes. In some embodiments, for example, when a laser light source is used, the time for achieving these energy density outputs may be from about 0.1 seconds to about 10 seconds. Certain components of the optical spectrum can be applied for different times, powers, or energies. In the case where multiple light sources are used, one or more light sources can be turned off after its energy density is provided or achieved.

Energy density or fluence or other dosage parameter, such as, for example, power, energy, illumination, or irradiance, may be measured at any of a variety of positions with respect to the tip 118 of the optical therapy device 100. For example, in one embodiment, fluence is measured substantially at the tip 118 of the optical therapy device 100. In this case, the dosage at the illumination surface is the fluence multiplied by the fluence area (for total power) and then divided by the illuminated surface area (e.g., in the nasal cavity, the surface area can range between 5 and 25 cm$^2$). Therefore to achieve the desired dosage density, the fluence at the tip is approximately the dosage multiplied by illuminated surface area and then divided by the tip area. In another embodiment, the fluence is measured at a distance of about 0.5 cm, about 1 cm, or about 2 cm from the surface of the tip 118 of the optical therapy device 100.

The particular clinical application and/or body cavity being treated may determine the energy density or dosage requirements. If the lining of the cavity is particularly far away from the optical therapy device 100, a higher energy, fluence, or intensity may be chosen. In the case where the nasal cavity is being treated and rhinitis is the disease, the dosage from the tip 118 may be chosen appropriately. For example, it has been shown by in-vitro work that T-cells undergo apoptosis at energy densities of about 50-100 mJ/cm$^2$ of combined UVA, UVB, and white light. The energy densities exiting from the tip of the optical therapy device used to achieve such energy densities as measured at the mucosa, or treatment site, may be 5-10 times this amount because of the optical therapy distance 100 from the nasal mucosa cells during treatment.

The energy densities may be further increased from that achieved in-vitro because of intervening biologic materials that may absorb light. For example, the mucus, which is present on top of the nasal mucosa in all patients, may absorb light in the desired region of the spectrum. In this case, the fluence or output of the optical therapy device 100 at the tip 118 can be corrected for the extra absorption. Furthermore, the mucosa may absorb more or less light at different time points during an allergy season (for example) and therefore the fluence of the optical therapy device may be controlled at these times. In many embodiments, this control is provided by the optical therapy devices. Photoreflectance data from the mucosa can be used by the patient, the medical practitioner, or automatic feedback (e.g., from the tip 118) to a controller and/or data processor. Such data can be used to estimate the thickness of the mucus layer and adjust the output of the optical therapy device 100 accordingly. In addition, the practitioner can evaluate the mucosa visually with a rhinoscope and adjust the optical parameters accordingly; in another embodiment, tube 106 delivers an image from the region surrounding the distal tip 118.

The dosage may be measured at a planar or curved surface with respect to the tip 118 of the optical therapy device 100. For example, in one embodiment, the dosage is measured at a plane that is tangential to the surface of the tip 118 of the optical therapy device 100. In another embodiment, the dosage is measured at a plane that is a distance of about 0.5 cm, 1 cm, 2 cm, 3 cm or 5 cm from the surface of the tip 118 of the optical therapy device 100. In another embodiment, the dosage is measured at a partially spherical plane that is at least partially tangential to, or at a distance of about 0.5 cm, 1 cm, 2 cm, 3 cm or 5 cm from the surface of the tip 118 of the optical therapy device 100. The selection of planar or curved surface for dosage measurement, and the distance between the measurement plane and the optical therapy device 100 tip 118 may be selected based upon the particular geometry of tip 118 utilized.

In one embodiment, the output portion 130 of the light source 126 is positioned so that it resides within at least a portion of the tube 106. When the output portion 130 of the light source 126 is so positioned, light emitted from the light source 126 is transmitted directly into the tube 106. In this embodiment, the tube is a reflecting tube. In such a case, optical losses may be minimized, or reduced. In addition, by positioning the output portion 130 of the light source 126 inside of the tube 106, additional optical focusing elements, such as lenses or mirrors, may not be required; moreover, the geometry of the tube can be optimized, such that light conduction is optimized by for example, creating surfaces within the tube designed to reflect light through and along the tube to transport the light to the distal end of the tube. In addition, the tube can be created to optimize total internal reflection of the light from the light source.

In some embodiments, the optical reflectance tube 120 includes one or more optical fibers that capture and guide the light from the light source/s 126. When the light sources 126 are small semiconductor structures, the fibers can encapsulate the semiconductor structure and faithfully transmit substantially all of the light from the light source 126. More than one fiber can be used to direct the light from multiple light sources 126. For example, each fiber can transmit light from one light source 126. In other embodiments, the optical tube 106 is or includes a light guide such as a liquid light guide (e.g., such as those available from EXFO in Ontario, Calif.).

The tube 106 may taper from a large diameter at its proximal end 108 to a smaller diameter at its distal end 116, in which case the tube 106 has a larger diameter at its proximal end 108 than at its distal end 116. In another embodiment, the tube 106 may taper from a larger diameter at its distal end 116 to a smaller diameter at its proximal end 108. In such case, the tube 106 has a larger diameter at its distal end 116 than at its proximal end 108. In other embodiments, the tube 106 is substantially cylindrical. In such case, the diameter of the tube 106 may be substantially constant along its entire length.

In one embodiment, the tube 106 is flexible so that its shape and orientation with respect to the handpiece 102 may be adjusted. A flexible material, such as rubber, plastic, or metal may be used to construct the tube 106, and to provide flexibility thereto. In one embodiment, a goose-neck tube, or spiral wound coil is used to provide a flexible tube 106. In such embodiments, an outer sheath 142 may be provided with the tube 106 to isolate the flexible portion of the tube 106 from the inside of a patient's nasal cavity.

An outer sheath 142 can be made from any of a variety of biocompatible materials well-known in the art such as, but not limited to, PTFE, ePTFE, FEP, PVDF, or silicone elastomers. The outer sheath can be disposable so that a clean, sterilized sheath can be used for each newly treated patient. The outer sheath 142 can also have beneficial optical properties. For example, the outer sheath can diffuse or otherwise pattern the light entering it from the optical tube 106. The outer sheath can be made of more than one material. For example, in some embodiments, the portion of the sheath where the light exits (e.g., the lens) 140 can be produced from an optically transparent material such as silicone, fused silica, or quartz, and the biocompatible portion which surrounds tube 106 can be produced from a material which is more flexible or lubricious, such as PTFE, but which does not necessarily transmit ultraviolet light.

In one embodiment, tube 106 is sized so it may be inserted into the nasal cavity of a patient or user as discussed above. In one embodiment, the tube 106 is inserted into the nasal cavity until its tip 118 reaches the turbinates, the sinuses, or the ostia to the sinuses. The tube 106 may be made of flexible materials so that it can bend, or be steered around corners, or conform to the shape of the nasal cavity, as required. In other embodiments, the light is emitted from just beyond the nares and diffuses along a cylindrical path toward the nasal mucosa.

The tube 106 may be made from any one or a combination of materials as described above. For example, the tube 106 may be made from polymers. In such case, since many polymers absorb light in the ultraviolet portion of the spectrum, the inside wall 120 of the tube 106 may be coated with a reflective coating or layer 122, as described above. The outside of the tube 106 can also be coated with a polymer with the inner material being one of the materials noted above.

In one embodiment, the reflective layer 122 includes an electrolessly-deposited metal. For example, layer 122 may include nickel, nickel-phosphorous, cobalt, cobalt-phosphorous, nickel-cobalt-phosphorous and/or a noble metal. In other embodiments, the layer 122 includes a reflective polymeric coating. In other embodiments, the reflecting layer is a specialty thin film, such as silica carbide deposited in a chemical vapor deposition process.

In one embodiment, the tube 106 includes quartz, fused silica, aluminum, stainless steel, or any material which reflects a substantial amount of light in the ultraviolet region and/or visible region of the electromagnetic spectrum.

The optical therapy device 100 generally allows for the use of low pressure light sources 126 and can be manufactured at low cost using safe light sources 126. By utilizing a low pressure light source 126, the light source 126 may be manufactured at a small size so that it can fit within a hand-held handpiece 102 of the optical therapy device 100.

The controller 136 of the optical therapy device 100 is adapted to control the quantity (e.g., total energy) and intensity (e.g., power) of light emitted by the light source 126 and thereby exiting the tip 118 of the optical therapy device 100. For example, in one embodiment, the controller 136 determines and/or controls the power from the power supply 110 as described in greater detail above. In one embodiment, the controller 136 may be programmed and may include a timer so that only a pre-specified amount of light can be provided by the optical therapy device 100 at any given time, and such that a user cannot receive more than a predetermined dose in a specified short time period (e.g., over a period of one day) or a number of doses in a specified time period (e.g., over a period of months, for example). In other embodiments, the controller 136 determines the illumination pattern. For example, by turning one or more light sources on and off, the illumination pattern can be controlled. The controller 136 can further control the illumination pattern by moving (actively or passively) or otherwise altering the aperture or pattern of the tip 118. The controller 136 can also apply current to the light sources at a desired frequency or duty cycle.

In another embodiment, the controller 136 delivers a large current or a current or voltage pulse to the light source 126 to "burn out" or destroy the light source 126 after a selected period of time. For example, after a predetermined "useful lifetime" of the optical therapy device 100 expires, a "burn out" current is provided and the optical therapy device 100 essentially ceases to function. At this time, the optical therapy device 100 is discarded. The controller 136 can also respond to or receive a control signal from one or more photodetectors placed in or on the tube 106 or the controller can respond to receive a control signal from one or more photodetector devices in an external calibration unit.

The power supply 110 of the optical therapy device 100 is adapted to receive power from an alternating current (AC) source, a direct current (DC) source, or both depending on the number and types of light sources. For example, in one embodiment, power supply 110 includes a battery, battery pack, rechargeable DC source, capacitor, or any other energy storage or generation (for example, a fuel cell or photovoltaic cell) device known to those of skill in the art. In some embodiments, an LED may utilize a DC power source whereas a mercury vapor lamp may utilize an AC power source.

In one embodiment, the light source 126 includes a low pressure lamp with an output (measured at any of the locations described above) between about 100 µW/cm$^2$ and about 5 mW/cm 2. In one embodiment, the light source 126 generates ultraviolet light and it includes at least a small amount of mercury within a nitrogen atmosphere. As discussed above, the output portion 130 of the light source 126 may be any material translucent to ultraviolet light, such as, for example, but not limited to, quartz, silicone or fused silica. The output portion can direct the light in a uniform or non-uniform pattern.

In one embodiment, when mercury vapor is used in connection with the light source 126, the light source 126 provides ultraviolet light having an output peak concentrated at 254 nm. In another embodiment, a phosphor or a combination of phosphors can be used, as is widely known to those skilled in the art. In one embodiment, phosphors are added to the light source 126 such that the output peaks from the light source 126 are customized based upon the desired clinical application and action spectra for the disease process being treated. In one embodiment, the light source 126 includes a mercury vapor lamp having a spectral output which resides in longer wavelengths of the ultraviolet spectrum and in some embodiments extends into the visible spectrum.

In one embodiment, light source 126 is a mercury vapor lamp such as the type 2095 lamp manufactured by Gelight Corporation. In another embodiment, the light source 126 includes a light emitting diode (LED) such as the UV LED manufactured by S-ET Corporation (Columbia, S.C.), which can be produced to emit narrowband light at any wavelength from about 250 nm to 365 nm. In another embodiment, the light source 126 emits at a wavelength of 275 nm. In such cases, the UV LED may have a sapphire substrate with conductive layers of aluminum gallium nitrite. For example, in one embodiment, the UV LED has about 50% aluminum. By varying the concentration of aluminum, the wavelength peak can be adjusted. In some embodiments, the several LEDs are packaged together such that light output with multiple peaks in the ultraviolet range can be achieved. In some embodiments, the aluminum concentration is varied along a dimension of the chip such that a more continuous spectrum is achieved when current is passed through the chip. In addition, the UV LED packaging may include flip-chip geometry. In such case, the LED die is flipped upside down and bonded onto a thermally conducting sub-mount. The finished LED is a bottom-emitting device that may use a transparent buffer layer and substrate.

In such embodiments, the light is two-times brighter when the LEDs are in a flip-chip geometry. This is due to the fact that light emitted from the LED is not physically blocked by an opaque metal contact on the top of the LED. In addition, flip-chip sub-mount pulls heat away from the device when made from materials having high thermal conductivity. This improves efficiency levels with less energy being converted to heat and more energy being converted to light. The resulting device will have a lower weight, will be smaller, and will be resistant to vibrations and shock.

In other embodiments, power delivery to the LEDs can be modified to optimize the optical power of the LEDs. In such cases, the LEDs are switched on and off in order to prevent heat build up which would otherwise decreases the efficiency of the LEDs. For example, a temperature rise may decrease the potential optical power. Such switching can increase the power output several-fold. In other embodiments, the semiconductor structure takes the form of a laser diode module wherein the semiconductor package contains reflecting optics to turn the non-coherent light into coherent light.

Although the power supply 110 of the optical therapy device 100 is illustrated in FIG. 1 as tethered to the proximal end 112 of the handpiece 102, it should be well understood by those of skill in the art that the power supply 110 may be incorporated into or included on or within the body of the device, including the handpiece 102. In such cases, the power supply 110 may include a battery, a battery pack, a capacitor, or any other power source. The power coupling 114 in such embodiments may include contacts or wires providing electrical communication between the power supply 110 and the control circuit 134.

A sleeve 140 may be provided to at least partially cover the tube 106. In one embodiment, the sleeve 140 is disposable and in another embodiment, the sleeve is not disposable. The term "disposable" is intended to have its ordinary meaning. In addition, as is known to those skilled in the art, disposable can also refer less to the particular material used and more to the cost of production and sales price of a component, as well as the procedure required to sterilize or otherwise clean the component between uses.

In some embodiments, the sleeve is sterilizable and in other embodiments, the sleeve is not sterilizable. Sterilizing methods include, without limitation, ethylene oxide (ETO), autoclaving, soap and water, acetone, and alcohol. In some embodiments, the sheath is machined and in other embodiments, the sleeve is formed from a mold. In still further embodiments, the sleeve is produced from a thermoforming process. In some embodiments, the sleeve is composed of multiple materials. For example, the body of the sleeve is produced from a material such as aluminum or a plastic coated with aluminum and the end of the sleeve is an optically transparent material. The end of the sleeve can also have an open configuration where the light diverges as it leaves the sleeve. The sleeve can also be solid and produced from the same or different materials. In this embodiment, the inner material will transmit light without absorbing the light. These configurations generally allow optical energy, or light, generated by the light source 126 to travel through the tube 106 and exit both the tip 118 of the tube 106 and the tip 140 of the sleeve. In such embodiments, light energy is emitted from the optical therapy device 100 and absorbed by the tissue within the body cavity (e.g., nasal cavity of the patient's nose).

The optical emitter 128 of the light source 126 is generally in electrical communication with leads 132. In one embodiment, the optical emitter 128 extends in a direction transverse the axis of the light source 126. As discussed above, the optical emitter 128 schematically represents only one embodiment of the light emitting portion of the handpiece 102 and light source 126. Optical emitter 128 (e.g., the light emitting portion of the light source 126) can be made from any of a variety of materials known to those of skill in the art; in cases where the optical emitter 128 represents a wire-filament type light source, the optical emitter 128 can include tungsten.

In embodiments where the light source 126 includes a gas-filled tube, such gases may include xenon, helium, argon, mercury, or mercury vapor, or a combination thereof, in order to produce a desired spectral output.

Although the optical emitter 128 of the light source 126 is shown at the distal end 124 of the handpiece 102, in other embodiments, the optical emitter 128 is positioned closer to the proximal end 112 of the handpiece 102. By moving the optical emitter 128 proximal with respect to the tip 118 of the tube 106, heat generated by the light source 126 may be at least partially separated from the tube 106, thereby lessening thermal communication with the patient's tissues.

Heat generated by the light source 126 may be removed from the optical therapy device 100 by any of a variety of methods and devices known to those of skill in the art. For example, in one embodiment, heat is directed away from the handpiece 102 by convection or conduction. In other embodiments, active cooling devices, such as thermo-electric coolers or fans may be employed. Alternatively, or in addition, passive cooling structures, such as heat fins, heat conductors and/or cooling tubes may be used to remove heat from the optical therapy device 100.

In one embodiment, the light source 126 includes a solid state light emitter (e.g., an LED or laser diode module) and the light source 126 is positioned at or near the distal end 116 of the tube 106 instead of within the handpiece 102.

In another embodiment, the light source 126 includes a solid state emitter and a mercury vapor lamp (or other analog-type light source that emits ultraviolet light as described above). Such combinations may be useful to provide light of multiple wavelengths or intensities that correspond to select spectral peaks. In another embodiment, multiple solid state emitters may be employed to achieve the same or similar results. In yet another embodiment, a visible light solid state emitter is combined with a mercury vapor or halogen lamp to enhance wavelengths in the visible light region. Alternatively, an array of solid state emitters may be arranged on an integrated circuit layout to produce spectral output that can be continuous or semi-continuous depending upon the wavelength, number and bandwidth of each emitter.

The tube 106 may include a soft coating on its outside surface 138. A soft coating, such as a polymer, rubber, or fluid-filled jacket, provides a comfortable interface between the outside surface 138 of the reflecting tube 106 and the patient's nose.

In addition, the reflecting tube 106 may include one or more filters along its length. In one embodiment, a filter is placed inside the reflecting tube 106 near its proximal end 112 or near its distal end 116. The filter may function as a lens if cut into an appropriate shape and placed at the distal end 116 of the reflecting tube 106. One such optical filter well known to those of skill in the art is manufactured by Schott and includes glass optimized for absorption at certain wavelengths.

In one embodiment, the light source 126 is about 10% to about 15% efficient. In another embodiment, the light source or combinations of light sources 126 generates about 10 mW to about 100 mW of optical power. In another embodiment, the light source dissipates between about 10 W to about 20 W of power in order to generate about 10 mW to about 100 mW of optical power. In one embodiment, excess heat is dissipated so that the optical therapy device 100 does not overheat, and/or so that the patient does not experience discomfort during its use.

Heat transfer control may become increasingly important when the optical therapy device 100 includes a light source 126 that is located near the distal end 116 of the tube 106 (e.g., heat may be closer to the patient's tissue). In one embodiment where the light source 126 is a mercury vapor light source, heat is generated near the output portion 130, for example, where the mercury plasma is generated. Since, in this embodiment, most of the light generated is non-blackbody radiation, very little heat is generated as photons propagate towards the distal end 116 of the tube 106 and enter the tissue of the patient. Therefore, in such embodiments, heat transfer mechanisms are generally confined to the output portion 130 of the light source 126, close to where the light is generated.

In one embodiment, a fan is used to transfer heat or to remove heat from the optical therapy device 100. For example, the fan may surround the output portion 130 of the light source 126 or the entire light source 126 itself. In such embodiments, the fan may surround the light source 126, or a portion thereof, in an annular fashion, and can direct heat away from the light source 126 and away from the patient via convection.

In another embodiment, a heat tube is placed around the light source 126 and the heat tube directs heat away from the patient towards the proximal end 112 of the handpiece 102. At the proximal end 112 of the optical therapy device 100, heat may be released into the environment. In one embodiment, the heat tube terminates in a structure optimized for heat transfer into the surrounding environment, for example, cooling fins. Alternatively, or in combination, in another embodiment, a fan is provided at the proximal end 112 of the optical therapy device 100 and at the proximal end of the heat tube. The fan provides active convection to carry heat away from the optical therapy device 100.

In one embodiment, a controller 136 controls the power output from the power supply 110 so that the light source 126 is activated for a predetermined time period. The controller 136 may include a switching mechanism that, in one embodiment, is controlled external to the device. Such external control may be implemented by any of a variety of mechanisms, such as, for example, a radio frequency communicator. The controller 136 helps avoid misuse or overuse of the optical therapy device 100. The controller 136 may also allow optimization to be carried out by the physician prescribing the device. In another embodiment, the controller 136 provides for preset dose quantity and frequency. In one embodiment, these parameters are set by the patient's physician. In one embodiment, parameters are set by the controller, a nurse, doctor, caregiver, patient, or other individual, or may be set according to prescription set forth by clinician.

In one embodiment, the optical therapy device 100 includes software (not shown) to control the dosage of optical energy to a patient. In one embodiment, the energy, power, intensity, and/or fluence of the optical output may be adjusted. Adjustments and settings may be saved within or loaded onto the optical therapy device 100 to correspond to the requirements of a particular patient, or clinical result.

In one embodiment, the treatment dose includes timing controls. Timing controls may include the amount of time the light source 126 of the optical therapy device 100 may be activated for a treatment. In another embodiment, timing controls include pulsing parameters, such as pulse width, timing of optical pulses, or relative sequence of pulses of light emitted from one or multiple light sources 126. In one embodiment, the light source 126 provides continuous (non-pulsed) optical output, and the timing controls include the duration of treatment, the time between treatments, and the number of treatments allowed in a specified time period, for example, one day.

In another embodiment, such as described with respect to FIG. 2 below, the controller 136 is not included within the handpiece 102 of the optical therapy device 100. In such embodiment, power delivery and timing controls are provided to the handpiece 102 from a source (such as control unit 202) outside of the handpiece 102. In such embodiment, the handpiece 102 may be disposable, and the physician may control the doses to the individual patient from a personal computer 204 or directly from power supply components, such as described below in additional detail.

The optical therapy device 100 may be used to treat or diagnose any of a variety of diseases. In one embodiment, the optical therapy device 100, is used to modulate immune or inflammatory activity at an epithelial or mucosal surface. Different immune and/or inflammatory reactions may be treated with combinations of ultraviolet and/or white light. In one embodiment, the optical therapy device 100 is used to treat allergic rhinitis, chronic allergic sinusitis, hay fever, as well as disease states such as dry eyes, allergic conjunctivitis or other immune-mediated mucosal diseases. In addition, the optical therapy device 100 may be used to treat any symptom associated with such conditions, such as sneezing, rhinorrhea, palate itching, ocular itching, congestion, and/or nasal itching. In other embodiments, optical therapy device 100 is used to treat skin disorders such as alopecia, acne, vitiligo, dermatoses, psoriasis, atopic dermatitis, and scleroderma. In some embodiments, the optical therapy device also diagnoses disease in combination with therapeutic delivery or alone without therapy.

Allergic rhinitis is an immune mediated process resulting from an allergen, such as ragweed, cat dander, mountain cedar, etc. The allergen combines with IGE present in and on cells of the mucosal surface of the nose or other mucosal surface, which leads to the degranulation of mast cells. This releases histamine and other mediators, which then lead to an immediate inflammatory reaction as well as an organized immune response that may last for days to weeks, or even months.

In other embodiments, the optical therapy device 100 is used to directly treat microbial pathogens or non-pathogens, such as fungi, parasites, bacteria, viruses that colonize, infect, or otherwise inhabit epithelial and/or mucosal surfaces. For example, patients with chronic sinusitis frequently have fungal colonization or a frank infectious process leading to the disease process. One clinical advantage of utilizing ultraviolet light to eradicate infections is that it avoids problems associated with antibiotic resistance. Antibiotic resistance is becoming an increasingly difficult problem to contend with in the medical clinic. In particular, patients with sinusitis generally undergo multiple courses of antibiotic therapy, which is typically ineffective. Antibiotic therapy is typically ineffective because the chronic nature of the sinuses in chronic sinusitis leads to production of a biofilm, which by its nature can prevent antibiotics from reaching the sinuses. Adjunctive phototherapy is another weapon in the armamentarium against microbes.

In some disease states, patients are allergic to allergens shed by microbes, such as in allergic fungal sinusitis. Microbes, and in particular fungi, are particularly sensitive to light with wavelengths ranging from 250 nm to 290 nm. At these wavelengths, the light directly affects the cellular macromolecules and can, for example, crosslink and/or dimerize DNA. Although the 250-290 nm wavelength light may be useful to injure or destroy pathogens, light having higher wavelengths (e.g., 300-450 nm) can also lead to cellular injury, albeit at higher optical powers. Ultraviolet light in the range 150-250 nm can also be used to destroy pathogens.

When combined with other chemicals or pharmaceuticals (e.g., moieties), light of different wavelengths can be used to treat pathogens. Such therapy, generally referred to as photodynamic therapy, allows almost any wavelength of light to be used to cause a biologic effect. This is because the light is absorbed by the moiety, which causes a toxic effect. The moiety can be chosen based upon its absorption characteristics, the light wavelength, or molecular specificity.

In some cases, the moiety or chemical entity resides in or around an epithelialized surface. For example, ultraviolet light can induce oxygen to become ozone, which can spontaneously release a toxic oxygen radical. The toxic oxygen radical can injure or destroy the pathogens.

Other examples of photodynamic moieties include psoralen, a DNA cross-linker, which has been used for many years in PUVA treatment for psoriasis and other skin diseases because it potentiates the actions of UVA. Another FDA approved and widely used photodynamic therapy is 5-aminolevulinic acid which is a photosensitizer with an absorption maximum at 630 nm and which generates oxygen free radicals upon light exposure. More recently, photodynamic moieties have become increasingly complex and can include nanoparticles, such as those described by Loo, et al. in Nanoshell-Enabled Photonics-Based Imaging and Therapy of Cancer, 3(1) Technol Cancer Res Treat 33-40 (February 2004), which is incorporated by reference.

Nanoparticle-based therapy systems allow for wavelength tuning so that the wavelength of maximal absorption can be customized to the application. Nanoparticles also allow for surface modifications so that the particle can target a specific tissue and then when the light focuses on that particular region, the specifically targeted nanoparticle will absorb the specific wavelength of light; therefore, regional specificity as well as wavelength specificity can be achieved with one particle. It is possible that the moieties resonate in response to specific frequencies (e.g., on-off frequency as opposed to electromagnetic frequency) in addition to wavelengths so that certain particles are activated when the optical therapy device deliver light of specific wavelength and with a specific on-off frequency.

When it is desired to treat microbes at epithelial or mucosal surfaces, such as the sinuses, an optical therapy device 100, including a mercury vapor lamp light source 126, may be utilized. Such a light source 126 generally emits light primarily at a 254 nm wavelength, which can destroy bacteria, fungi, viruses, and even fungal spores (discussed above). In other embodiments, an array (e.g., one or more) of light emitting diodes (LEDs) or laser diode modules is used. The array emits light (typically in the ultraviolet C and short wavelength ultraviolet B regimes) at one or more wavelengths selected to destroy polynucleotides (e.g., DNA and/or RNA), cell membranes, and/or proteins of the pathogens. In other embodiments, LEDs are used in photodynamic therapy and activate the moiety to exert its biologic effect.

An optical therapy system 200, in accordance with another embodiment of the present invention, is illustrated in FIG. 2. The optical therapy system 200 includes an optical therapy device 100, a control unit 202, and at least one computer 204. Control unit 202 communicates with optical therapy device 100 via power coupling 114, such as power coupling 114 described above, with respect to FIG. 1. Power coupling 114 may provide communication of power and electronic control signals between control unit 202 and the optical therapy device 100. The control unit 202 is also coupled to at least one computer 204 via computer coupling 206. Computer coupling 206 may be any of a variety of structures, devices, or methods known to those of skill in the art that enable communication between computers or computing devices. For example, in one embodiment, computer coupling 206 is a cable, such as a USB or Ethernet cable. In another embodiment, the computer coupling 206 is a wireless link. The at least one computer 204 may include a personal computer, such as a PC, an Apple computer, or may include any of a variety of computing devices, such as a personal digital assistant (PDA), a cellular telephone, a BLACKBERRY™, or other computing device.

Computer coupling 206 may include any wired or wireless computing connection, including a Bluetooth™, infrared (e.g., IR), radiofrequency (e.g., RF), or IEEE 802.11(a)-, (b)-, or (g)-standard connection. Control unit 202 and computer 204 may form a network within which multiple computers 204 or computing devices, or control units 202 may be included.

In one embodiment, control unit 202 is connected to a power supply via a power cord 208. Control unit 202 also generally includes a display 210, a keypad 212, controls 214, and a cradle 216. Display 210 may include a screen or other output device, such as indicators, lights, LEDs, or a printer. In some embodiments, the display 210 is of the touchscreen variety and includes touch controls to control the parameters of the optical therapy device 100. Controls 214 include any of a variety of input devices, including knobs, levers, switches, dials, buttons, etc. In some embodiments, cradle 216 is adapted to receive the handpiece 102 of the optical therapy device 100 when not in use. Such a cradle 216 may furthermore be configured to provide electrical power (e.g., a rechargeable battery) to the handpiece of the optical therapy device 100 and/or control signals. In such embodiment, power coupling 114 may not be provided, or may be provided via the cradle 216 through electrical contacts. In some embodiments, the cradle 216 includes an optical detector, such as a photodiode, which can provide an indication of the output or strength of the optical light source 126 and can provide for calibration of the optical therapy device 100 over time.

Figure 3A:
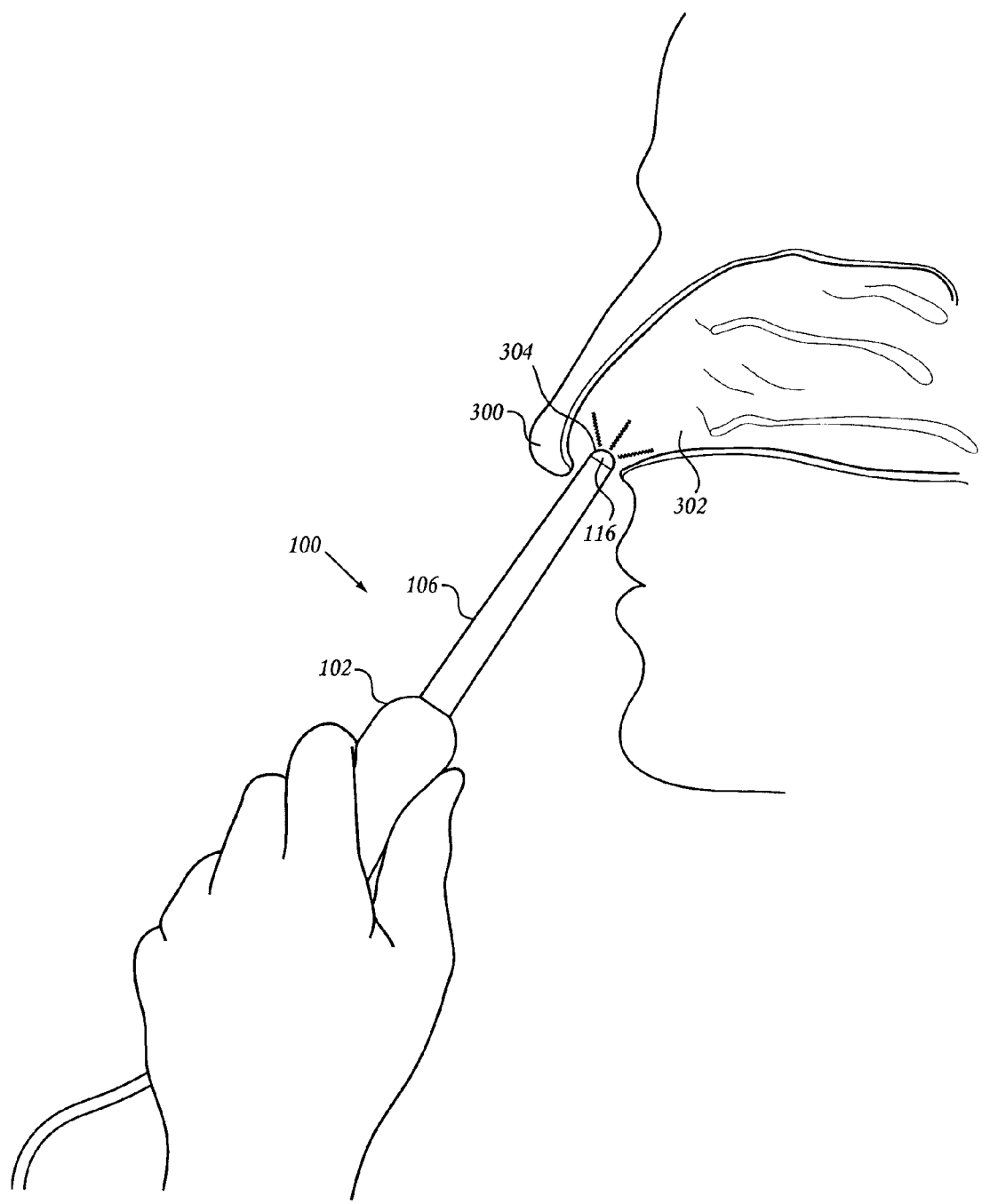
FIGS. 3A and 3B illustrate an optical therapy device inserted into a person's nasal cavity.

FIG. 3A illustrates one embodiment of the use of the optical therapy device 100. In the illustrated embodiment, the user (e.g., medical practitioner, nurse, doctor, or patient) holds the handpiece 102 of the optical therapy device 100 and inserts the tube 106 into his or her nose 300 (or into the nose of the patient when the medical practitioner is the user of the device). The light-emitting distal end 116 of the reflecting tube 106 is inserted inside of the nasal cavity 302 of the patient. Light is emitted from the optical therapy device 100 along a light propagation access 304 where it is absorbed by the mucosa and other soft tissues within the nasal cavity 302.

Figure 3B:
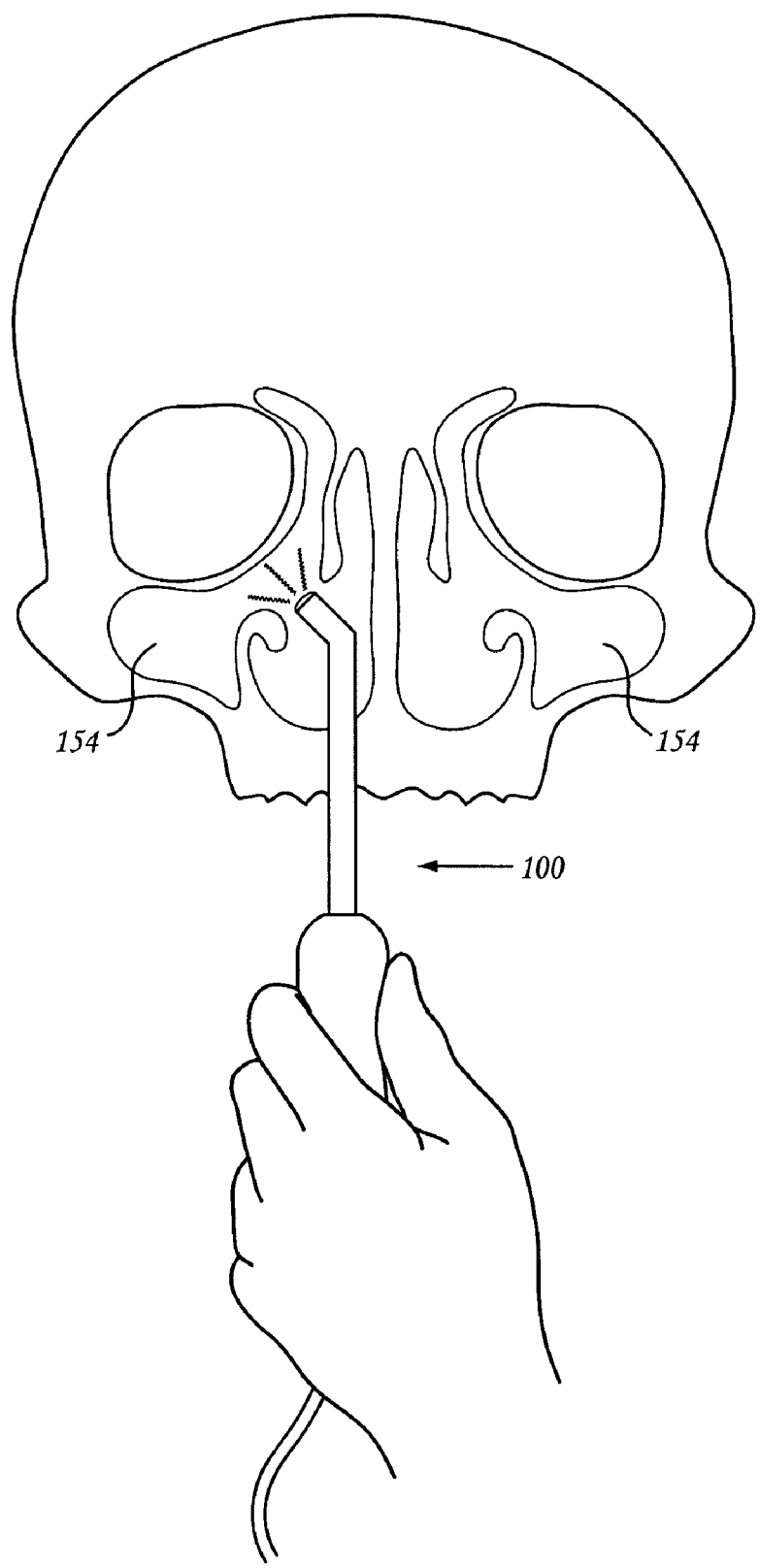

FIG. 3B illustrates one embodiment of an optical therapy device 100 adapted to be inserted into the paranasal sinus cavities 154, to treat conditions such as sinusitis. Optical therapy device 100 has a specific shape or contour to reach the sinus as will be described below. The various wavelengths of the optical therapy device 100 may be chosen depending upon whether fungal sinusitis or allergic sinusitis is to be treated. When allergic sinusitis is to be treated, wavelengths including visible light and ultraviolet light may be utilized. In the case where it is desired to treat fungi and/or other microbes, a lower wavelength, such as from 250-300 nm, may be used. In some cases, it is desirable to use all of these wavelengths separately or in combination, sequentially or concomitantly.

Although the optical therapy device 100 is illustrated and described herein as used for treating a patient's nose 300, the optical therapy device 100 may be adapted to treat any of a variety of cavities, surfaces, portions, or organs of the human or animal body. For example, in one embodiment, the optical therapy device 100 is adapted to treat the skin, or to be inserted into and treat tissue within the mouth, ear, vagina, stomach, esophagus, small intestine, bladder, renal pelvis, rectum and/or colon. For example, the optical therapy device 100 may be used to reduce inflammation within any mucosa of the body.

Furthermore, the optical therapy device 100 may be inserted into a body cavity to treat the walls of an organ without entering the lumens of the organ or the organ itself. Such is the case, for example, when the optical therapy device 100 is placed inside the chest cavity to treat the lungs, heart, or the esophagus. Such is also the case when the optical therapy device 100 is placed inside of the abdominal cavity to treat the intestines, stomach, liver, or pancreas. The optical therapy device can be adapted for insertion through a laparoscope, hysteroscope, thoracoscope, endoscope, otoscope, bronchoscope, cystoscope, or cardioscope.

In one such embodiment, the optical therapy device 100 is used to treat the clinical disease state of diastolic heart failure. In diastolic heart failure, collagen deposition in between or in place of (as is the case of ischemic cardiomyopathy) the myocardial fibers lead to a decreased compliance of the myocardium and a failure of the myocardium to relax properly during diastole. Ultraviolet light therapy, specifically ultraviolet A (UVA) light therapy, can activate the native collagenase system in human skin and lead to an increased compliance in diseases such as scleroderma, as discussed in greater detail above. A similar collagenase system is present within the myocardium and if activated, can decrease the compliance of the myocardium with a similar mechanism as in the skin.

In one embodiment, the optical therapy device 100 is adapted to treat inflammation and/or infection of the gastrointestinal tract caused by any of a variety of conditions, such as, Crohn's disease, ulcerative colitis (inflammatory bowel diseases), *C. difficile* colitis, and/or esophagitis. In some embodiments, the optical therapy device 100 can ameliorate the internal consequences of T-cell-mediated diseases, such as autoimmune and collagen vascular diseases, such as rheumatoid arthritis, systemic lupus erythematosis, psoriatic arthritis, etc. In some embodiments, the optical therapy device 100 is adapted to treat skin conditions, such as psoriasis. In yet another embodiment, the optical therapy device 100 is adapted to be inserted into the vagina to treat any of a variety of conditions, including yeast infection, vaginitis, vaginosis, *Candida*, parasites, bacteria, and even an unwanted pregnancy. The optical therapy device 100 may be inserted within the ear, and deliver light to the external or internal auditory canals to reduce inflammation and/or infection therein. In yet another embodiment, the optical therapy device 100 may be provided to the bladder, kidney, ureter, and/or urethra to treat and/or reduce inflammation. The optical therapy device 100 may also be used to treat rheumatoid arthritis, or to reduce or eliminate herpetic lesions (e.g., cold sores) by decreasing viral shedding time and/or time to healing.

In yet another embodiment, the optical therapy device 100 is adapted for veterinary use. For example, in one embodiment, the optical therapy device 100 is adapted to be inserted inside the nose of an equine, such as a racehorse, to treat rhinitis, reduce inflammation, or treat any of the diseases of conditions described herein. Other animals may benefit from treatment with the optical therapy device 100, including domestic animals, such as dogs, cats, and rabbits, as well as exotic animals, such as cheetah, gorilla and panda.

Figure 4:
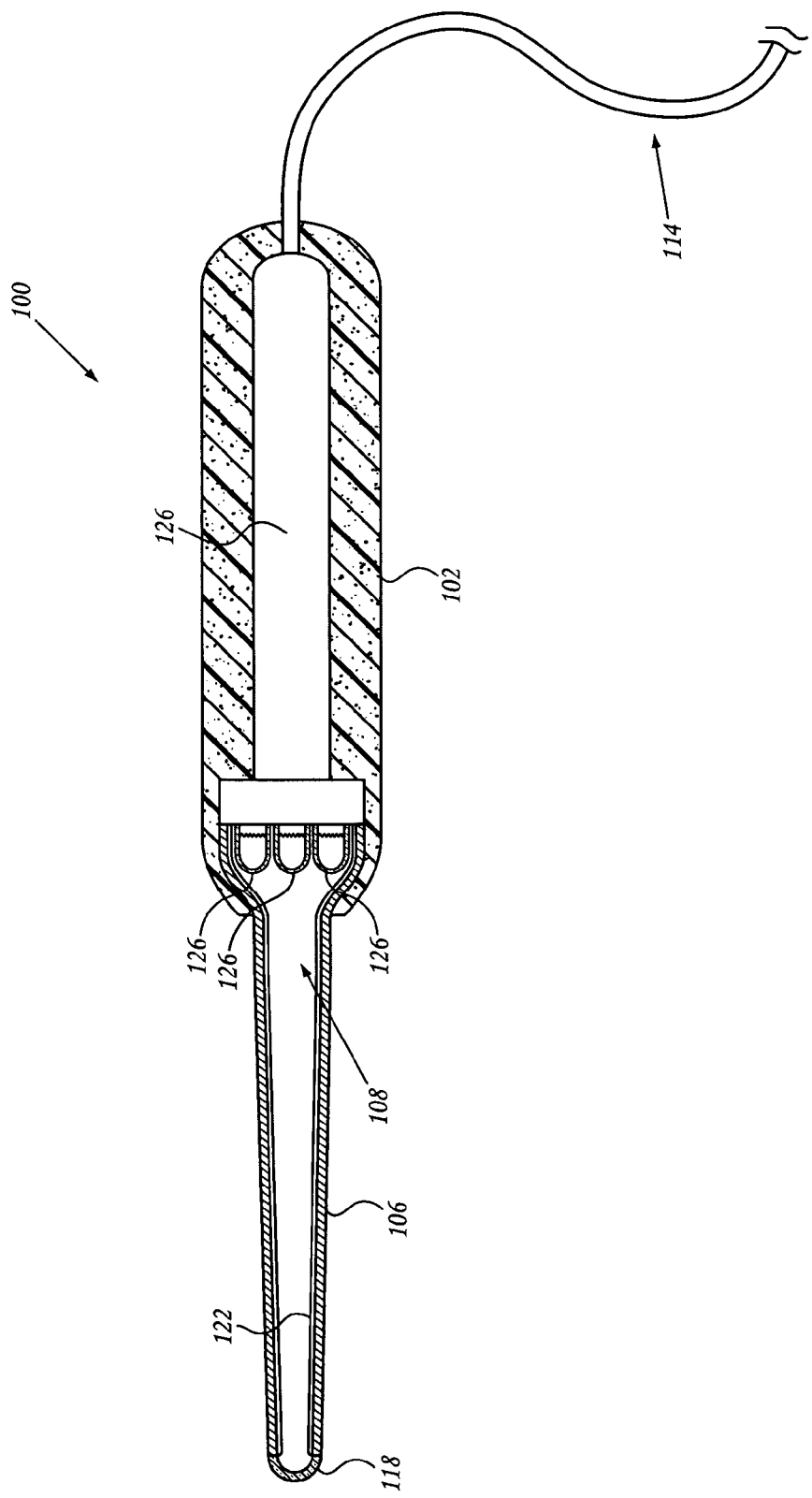

An optical therapy device 100, in accordance with another embodiment of the present invention, is illustrated in FIG. 4. The optical therapy device 100 of FIG. 4 includes a handpiece 102 and tube 106 similar to the optical therapy devices discussed above. In addition, the optical therapy device 100 of FIG. 4 includes multiple light sources 126. For example, as illustrated, optical therapy device 100 includes three light sources 126. Any number of light sources 126 may be utilized, including one, two, three, or more than three light sources 126. Light source 126 may be a bulb-type light source, such as a mercury vapor lamp or filament based light source, as discussed above, or an LED light source, or a combination thereof. Any of the control systems and power delivery systems discussed above may be incorporated into the optical therapy device 100 of FIG. 4.

Although the multiple light sources 126 of FIG. 4 are shown in close proximity, individual light sources 126 can be placed anywhere along the tube 106 or handpiece 102. In one embodiment, the light source(s) 126 is (are) located close to the distal tip 118. For example, in one embodiment, a UVB emitting source is placed close to the distal tip 118 and a white light source and/or UVA light source are/is placed proximally, toward the handpiece 102. Such a configuration can assure that UVB wavelengths reach the nasal mucosa because in many cases UVB light is difficult to transport faithfully. Even though the UVA and white light sources 126 may have more losses than the UVB light source 126, this is acceptable since, in at least one embodiment, the UVA and white light sources 126 generate a higher amount of optical energy or power and typically undergo less loss along an optical guidance system than UVB light.

An optical therapy device 100 in accordance with yet another embodiment of the present invention, is illustrated in FIG. 5A. Optical therapy device 100 includes a tube 106 and a handpiece 102, such as those described above with reference to FIGS. 1-4. However, in the present embodiment, optical therapy device 100 includes a passive cooling mechanism integrated therein. In one embodiment, the passive cooling mechanism includes a cooling sleeve in thermal communication with a heat diffuser 502 located at the proximal end 112 of the handpiece 102. A thermal interface 504 covers at least a portion of the proximal end 112 of the handpiece 102, and provides for dissipation of heat from the heat diffuser 502. In one embodiment, the cooling sleeve at least partially surrounds light source 126 of the handpiece 102.

The cooling sleeve may be made from any of a variety of thermally conductive materials, including aluminum, copper, steel, stainless steel, etc. In addition, the cooling sleeve may be filled with a thermally conductive material or a cooling material such as water, alcohol, freons, dowtherm A, etc. For higher temperature lamps, the cooling fluid could include sodium, silver, and others materials as are generally well-known in the art. In one embodiment, heat diffuser 502 includes cooling fins to increase its surface area. Increased surface area of the heat diffuser 502 provides efficient cooling for the light source 126 of the optical therapy device 100. The thermal interface 504 and/or heat sink 502 may be made from any of a variety of thermally conductive materials, including metals, such as aluminum, copper, steel, stainless steel, etc. The rounded surface of the thermal interface 504 protects the user and his or her hand from sharp or jagged edges of the heat sink 502. The thermal interface 504 can further be perforated to allow for convective flow from the heat sink 502.

In one embodiment, cooling sleeve is or includes a series of cooling pipes, or heat pipes 500, as is well-known in the art, such as those illustrated in FIGS. 5A-5B. Heat pipes 500 extend axially along the longitudinal axis of the handpiece 102 and generally run parallel to the light source 126.

A cross-sectional view of optical therapy device 100, taken along line 5B-5B, is illustrated in FIG. 5B. In the illustrated embodiment, a circumferential arrangement of heat pipes 500 is shown. As is well-known in the art, heat pipes 500 include a liquid (the coolant) that generally has a boiling point in the range of temperature of the portion to be cooled. Common fluids include water, freons, and dowtherm A, which has a boiling point temperature range of about 500-1000° C. A second portion of the heat pipe 500 is a wicking portion, which transmits the coolant in its liquid state. The coolant picks up heat at the hot region (e.g., proximate to the light source 126), is vaporized and travels down the center of the pipe, where the fluid then condenses at the cooler portion of the heat pipe 500, and then wicks back through the wicking portion of the heat pipe 500. The configuration of heat pipes 500 in FIG. 5B is only one example of any numerous shapes, sizes, and configurations of heat pipes 500, which may include flat, horseshoe shaped, annular, as well as any other shape. The heat pipes 500 can be placed anywhere along the tube 106 and even at its distal portion. The heat pipes 500 can be used in combination with any of the configurations, devices, and light sources above.

Figure 6A:
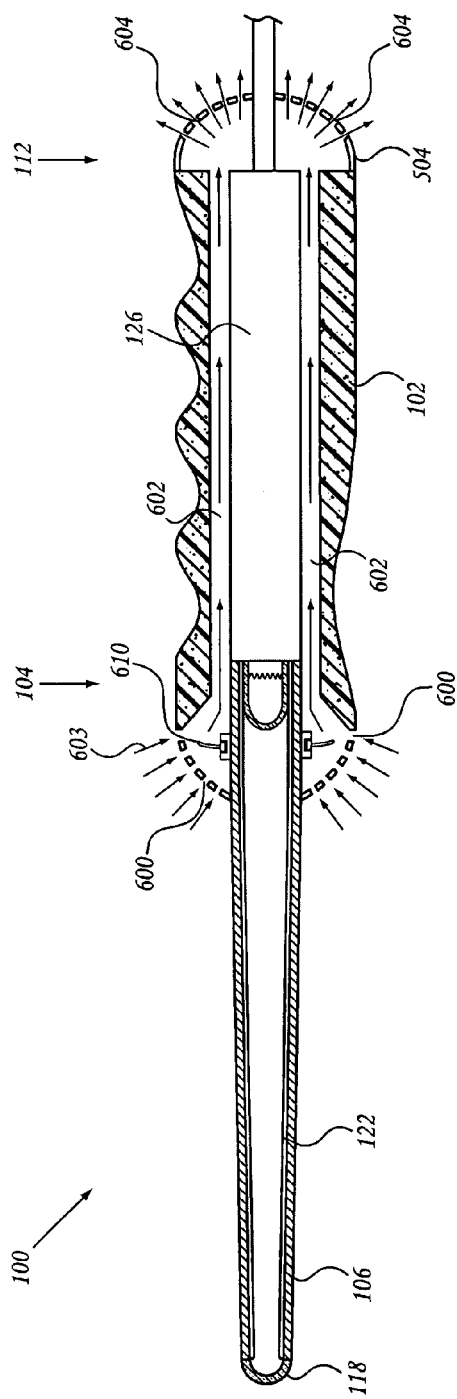
Figure 6B:
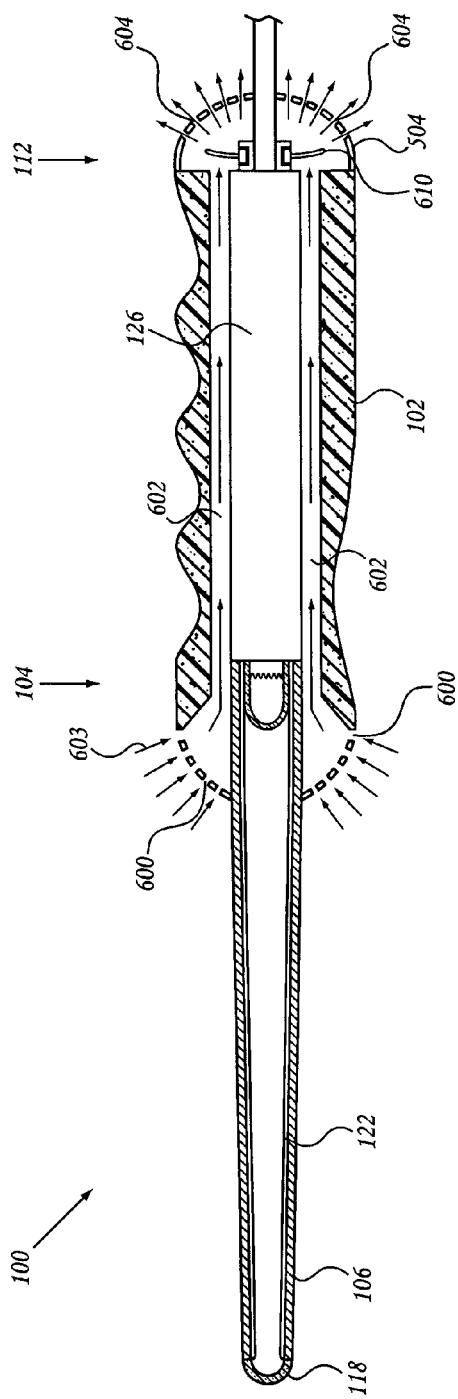

FIG. 6A and FIG. 6B illustrate an optical therapy device 100 in accordance with yet another embodiment of the present invention. In one embodiment, a fan 610 is provided near the distal end 104 of the handpiece 102 to actively transfer heat away from the optical therapy device 100. Handpiece 102 also includes at least one light source 126 as described in greater detail above. The fan 610 provides for active cooling by pulling air 603 into the handpiece through distal heat vents 600, through the handpiece 102 (e.g., in the direction of the arrows) via channel 602, and out the proximal end 112 of the handpiece 102 via heat vents 604 located in the thermal interface 504. In some embodiments, fan 610 is used in conjunction with fins, heat pipes, cooling pipes, cooling sleeves, and/or cooling tubes as described above. In another embodiment, fan 610 provides cooling by pulling or pushing air through the handpiece 102.

In another embodiment, such as illustrated in FIG. 6B, fan 610 is located at the proximal end 112 of the handpiece 102. Air is pulled through a channel 602 in the handpiece via distal heat vents 600. Air flowing through the handpiece 102 via channel 602 removes heat from light source 126. In this manner, the light source 126 is cooled.

Figure 7A:
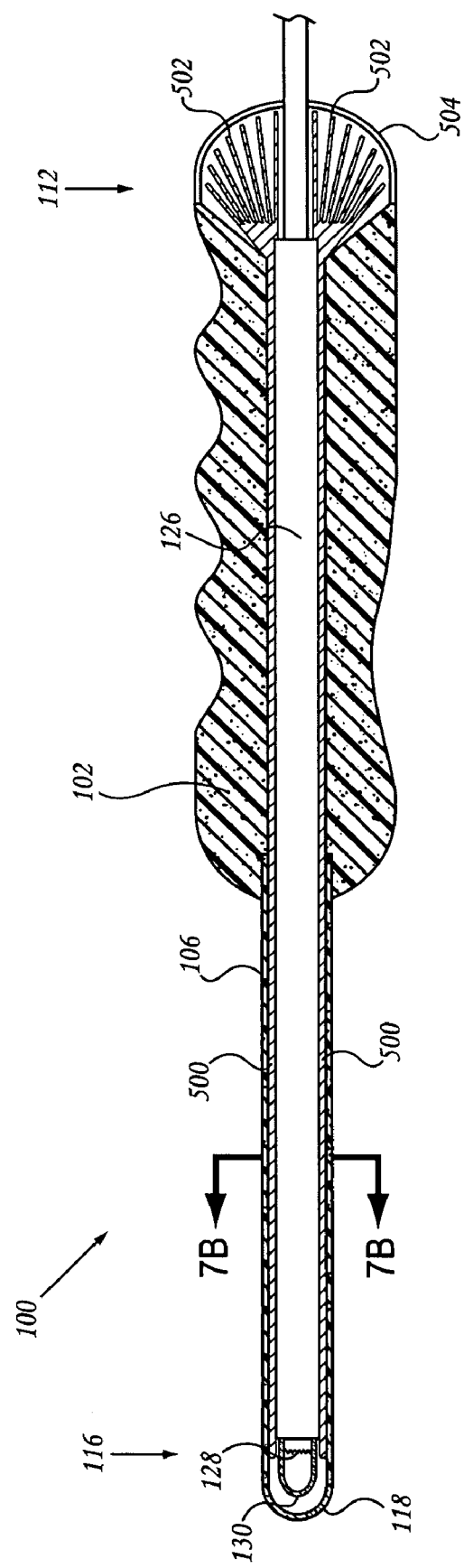

An optical therapy device 100 in accordance with another embodiment of the present invention is illustrated in FIG. 7A. Optical therapy device 100 includes handpiece 102 and tube 106, as described above with respect to FIGS. 1-6B. However, in the present embodiment, the light source 126 of the optical therapy device 100 is located at the distal end 116 of tube 106 near its distal tip 118. In the illustrated embodiment, tube 106 may not be configured to guide or reflect light since the light source 126 is located at or near its distal end 116. The tube 106 may be configured to guide light in cases when light exiting the tip of the device 118 includes light originating in the handpiece 102 and at the distal tip 118 of the tube 106.

As discussed above, light source 126 can be any of a number of different light sources. In one embodiment, light source 126 is an LED or multiple LEDs. In another embodiment, light source 126 includes one or more LEDs for generating UVB light and one or more LEDs for generating white light and/or UVA light. Additional light sources 126 can be combined (e.g., at the distal end 116), or one or more light sources 126 can be located closer to the proximal end 112. Of course, in this embodiment, an optical guidance system may be used to transmit or guide the light generated by the light source 126 located in the handpiece 102.

Since, in one embodiment, the majority of heat generated by the light source 126 is generated at the light source's distal end, heat pipes 500 are used to remove the heat therefrom. In one embodiment, when the light source 126 includes a double-bore mercury vapor lamp, optical emitter 128 is a double-bore quartz capillary tube. Mercury vapor lamps typically generate heat at their cathode and anode, which are generally located at the ends of the inner capillary tube. Therefore, in some embodiments, heat is generated primarily at the ends of the inner capillary tube. In another embodiment, when light source 126 consists of LEDs, optical emitter 128 is the chip array or package used to create light, such as solid state light. Heat generated at the circuitry may be carried away from the distal end 116 by heat pipes 500. In the case when light source 126 is an LED or a combination of LEDs, the heat generation from the conversion from electricity to light is minimal, or less significant; however, significant heat can be generated in the circuitry—especially when several LEDs are used in combination. In such and other cases, heat pipes 500 including heat conduction rods produced from materials that have good thermal conductivity, such as aluminum, copper, steel, stainless steel, etc., may be used.

Heat pipes 500 generally run parallel to the light source 126 along the axial length of the optical therapy device 100. Heat is transmitted, or is conducted, through the heat pipes 500 to the heat sink, as discussed in greater detail above. In other embodiments, heat pipes 500 are circumferentially wrapped around the light source 126 or tube 106.

Heat is carried from the light source 126 through the heat pipes 500 to the heat sink 502 located at the proximal end 112 of the handpiece 102. In one embodiment, heat is dissipated from the handpiece 102 through a heat sink 502 (which may include cooling fins), after which the heat exits handpiece 102 via a thermal interface 504.

Figure 7B:
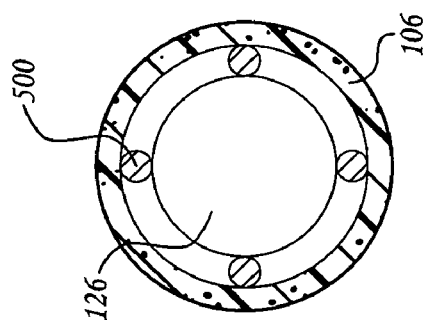
FIG. 7B is a cross-sectional view taken along line 7B-7B of FIG. 7A.

FIG. 7B shows a cross-section of the optical therapy device 100 of FIG. 7A along line 7B-7B.

Figure 8A:
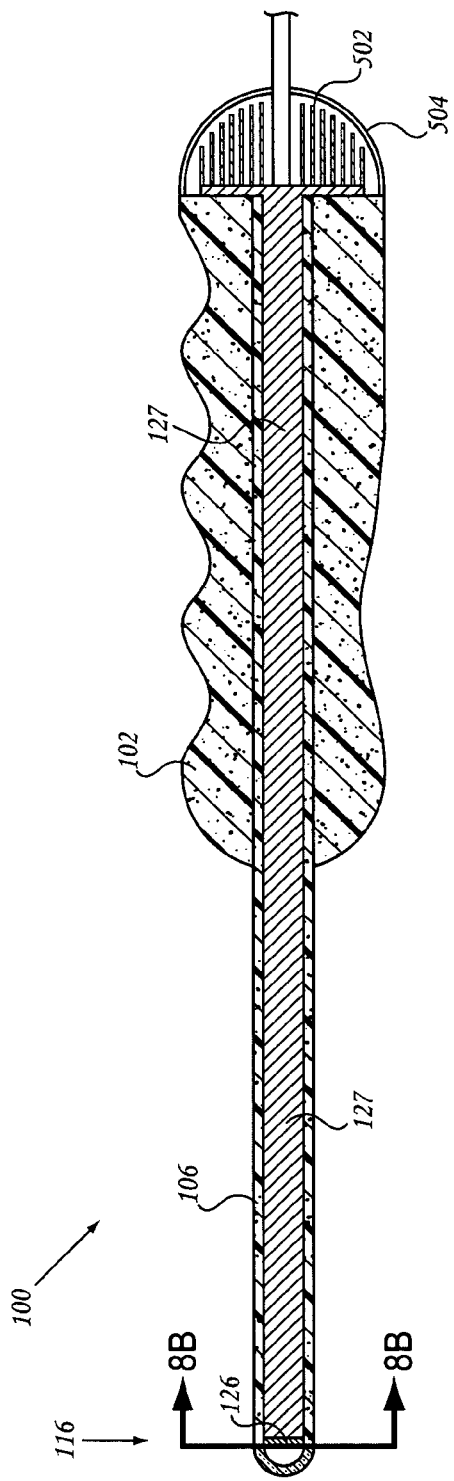
FIG. 8A is a cross-sectional view of an optical therapy device in accordance with other embodiments of the present invention.

FIG. 8A illustrates an optical therapy device 100 in accordance with yet another embodiment of the present invention. Optical therapy device 100 includes a handpiece 102 and tube 106 (which may or may not be a reflecting tube depending on the combination of light sources used) as described in greater detail above. In the present embodiment (illustrated in FIGS. 8A and 8B), light source 126 is located near the distal end 116 of the tube 106 similar to that described above with respect to FIG. 7A. However, in the present embodiment, light source 126 includes a solid state array of light sources, or a multitude of light sources arranged in a two- or three-dimensional array. In the case where all the desired wavelengths are emitted from the diode array, tube 106 does not have to be a reflecting tube. In such cases, the tube 106 can serve as a conducting tube for heat transfer (depending on the number and efficiency of the light emitting diodes, specialized heat transfer may or may not be employed). In addition, the tube 106 may be made from a soft, flexible material comfortable to the patient. In some embodiments, only certain wavelengths are provided by LED array and other wavelengths are transmitted through an optical tube 106, as described above.

Figure 8B:
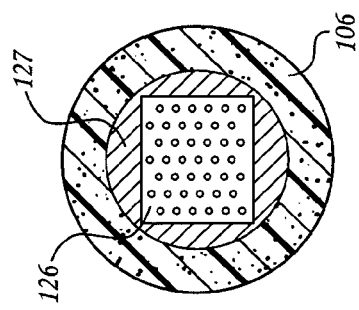
FIG. 8B is a cross-sectional view taken along line 8B-8B of FIG. 8A.

A cross-sectional view of optical therapy device 100 taken along line 8B-8B is illustrated in FIG. 8B. A diode array light source 126 is illustrated in the cross-section view of FIG. 8B. In one embodiment, all desired wavelengths are provided by the array 126, and a region 127 is adapted to transfer heat by any or all of the mechanisms discussed above. The region 127 can also be used to transmit additional optical spectra through optical fibers, tubes, or any of the devices described above.

FIGS. 9A-9H represent optical therapy devices 100 having different tubes 106 in accordance with alternative embodiments of the present invention and generally configured to treat the sinuses of a patient. The handpiece 102 is shown in a cutaway view, as it may be substantially the same for these embodiments. Each tube 106 is configured to optimize a particular parameter based upon specific clinical needs and/or reach a particular body region such as the maxillary sinus, the ethmoid sinus, the frontal sinus, etc. As such, tubes 106 having varying lengths, shapes, curvatures, diameters, radiuses, bends, and tapers may be utilized or selected by a clinician as required. The tube 106 may also have light sources 126 placed anywhere in, on, or along the tubes 106. In some embodiments, the tube 106 is not optically reflecting because the light is generated at its distal end. In such embodiment, the tube 106 may serve as a conduit for electrical or heat transfer.

Figure 9A:
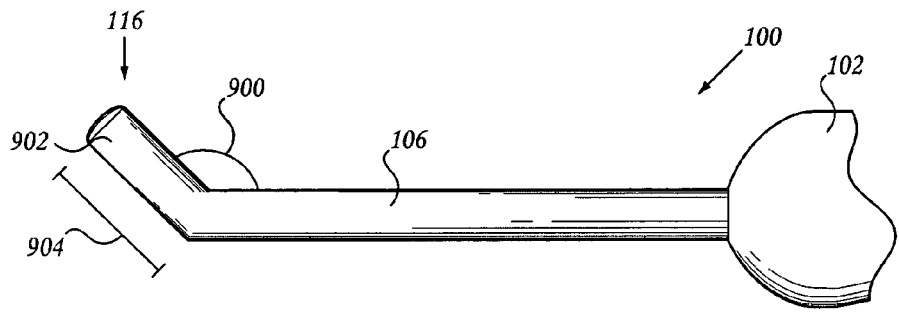
FIGS. 9A-9H illustrate optical therapy devices having different tubes in accordance with additional embodiments of the present invention and generally configured to treat the sinuses of a patient.

In the optical therapy device 100 illustrated in FIG. 9A, handpiece 102 is connected to reflecting tube 106 that has a bend at its distal end 116. The distal end 116 of the tube 106 is bent at a bend angle 900 to create a distal segment 902. The distal segment 902 has a distal length 904 that may be selected to configure to the anatomy of a particular patient. In some embodiments, optical therapy device shown in FIG. 9A is utilized to treat the sinuses of a patient.

In some embodiments, tip 902 can be flexible and may include a hinge (not shown) and/or a flexible material so that angle 900 can be adjusted by the practitioner. A light source 126 or combinations of light sources 126 can be placed anywhere along tube 106 as described above. The light source 126 can also reside in handpiece 102, as described above. Tube 106 can also contain an optical fiber bundle or it can be hollow and configured to reflect light, as discussed above. Furthermore, depending on the light source 126 selected, the tube 106 can be configured to transfer heat from the light source 126, as described above.

Figure 9B:
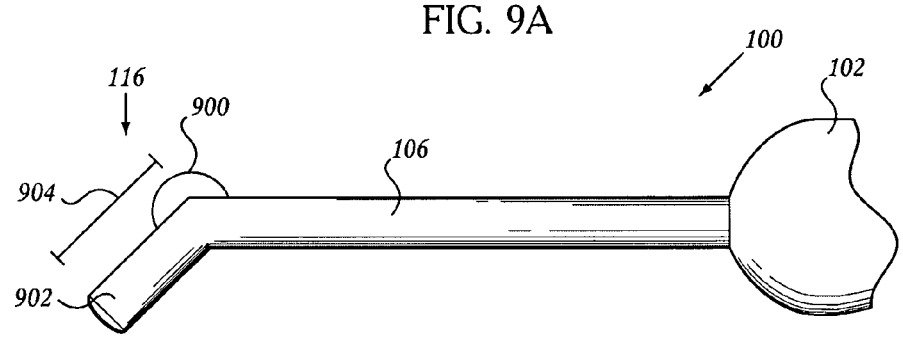

Similarly, as illustrated in FIG. 9B, optical therapy system 100 includes a handpiece 102 that is connected to a reflecting or non-reflecting tube 106 having a distal segment 902 of a different bend angle 900 at its distal end 116. The distal length 904 of the distal segment 902 may be the same or different than that of FIG. 9A. In addition, the bend angle 900 is shown at a greater angle than that shown in FIG. 9B is greater than that shown in FIG. 9A. Similarly, such designs are used to reach the sinuses or other internal cavities or surfaces of a patient.

Figure 9C:
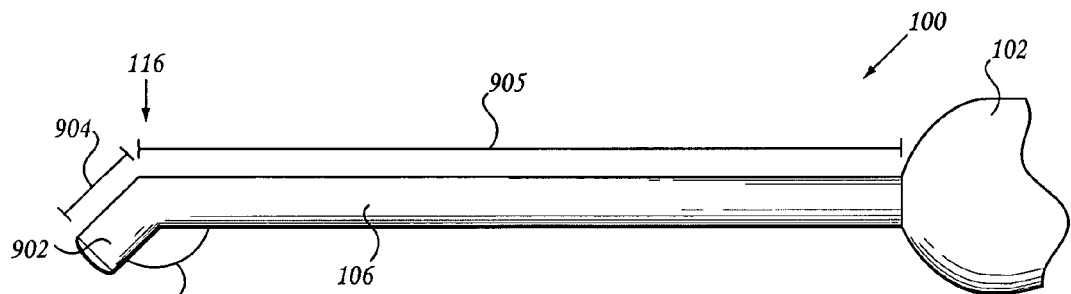

The distal length 904 of the distal segment 902 may be varied as clinically required, as illustrated in FIG. 9C. The distal length 904 may vary between 1 cm and 4 cm. Proximal length 905 varies between about 6 and 12 inches. Bend angle 900 varies from about 45-60 degrees in some embodiments, and from about 60-80 degrees in other embodiments.

Figure 9D:
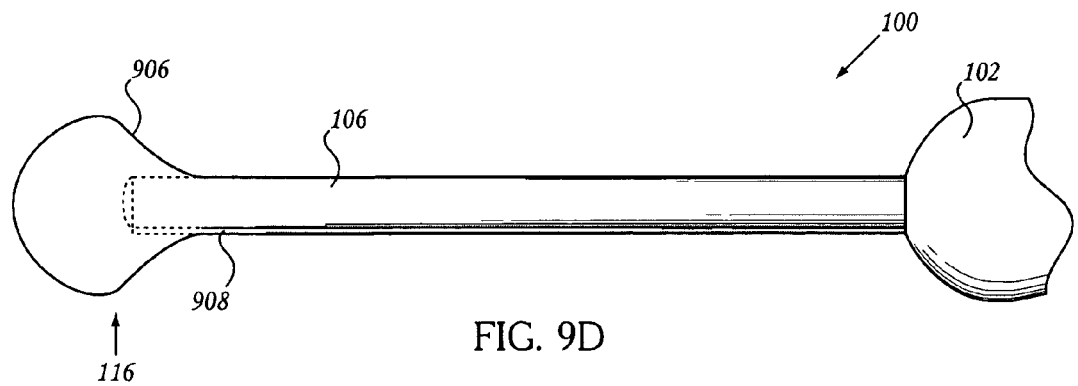

An optical therapy device 100 in accordance with yet another embodiment of the present invention is illustrated in FIG. 9D. The optical therapy device 100 of FIG. 9D includes a handpiece 102 coupled to a reflecting tube 106 that includes an expandable balloon 906 at the reflecting tube's distal end 116. The reflecting tube 106 may be inserted into a patient's nose and/or sinus and the expandable balloon 906 may thereafter be inflated with a liquid, gas, polymer, a hydrogel, or a combination thereof, including a combination of fluids. By inflating the expandable balloon 906, the tissue (e.g., mucosa) on the inside surface of the patient's nose or sinus is flattened out to allow a more even distribution of light energy thereto. In addition, inflating the expandable balloon 906 allows the optical therapy device 100 to be positioned within the patient's body in such a way as to allow more exposure of mucosal surface area. The temperature of the fluid inserted into the balloon described above can be varied from low temperature (e.g., lower than body temperature) to high temperature (e.g., above body temperature) to treat the mucosa of the sinuses and to work independently or synergistically with the optical therapy device 100.

In one embodiment, the compression balloon 906 is made from an optically transparent material; for example, a material which is transparent to ultraviolet light. Examples of transparent materials include certain formulations of PVDF as can be found in Japanese Patent No 01241557, which is incorporated by reference herein; certain fluoropolymers such as fluorinated ethylene propylene (FEP) produced by Zeus Inc; certain derivatives of Teflon (e.g., Teflon-AF produced by Dupont); certain formulation of silicone; and/or certain elastomeric formulations of silicone dioxide. The balloon may be compliant or non-compliant and may have single, double or multiple lumens.

The compression balloon 906 may be inflated by passing a fluid, liquid, gas, or a combination through an inflation lumen 908 from the handpiece 102 to the compression balloon 906. The compression balloon 906 may be deflated in a similar matter.

Figure 9E:
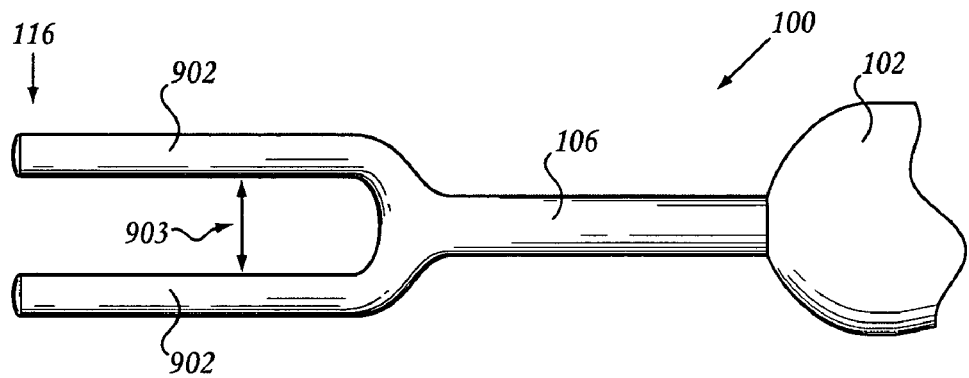

The reflecting tube 106 of the optical therapy device 100 may include more than one distal segment 902 such as is illustrated in FIG. 9E. In the embodiment of FIG. 9E, optical therapy device 100 includes a tube 106 having two distal segments 902. In one embodiment, the distal segments 902 have equal distal lengths 904 although in other embodiments, the distal lengths of the distal segments 902 are different.

In another embodiment, the distal segments 902 are flexible so that the relative spacing 903 between the distal segments 902 may be adjusted to accommodate the anatomy of particular patients. Incorporating more than one distal segment 902 can be highly beneficial in the clinical setting since the total amount of time the patient spends receiving the optical therapy may be reduced. This results in improved patient compliance because of the decreased treatment times.

In one embodiment, the distal segments 902 are parallel to one another although in other embodiments, they are not. In one embodiment, each distal segment is oriented at an angle with respect to the axis of the reflecting tube 106. For example, in one embodiment, distal segment 902 projects at an angle between about 1 and 15 degrees with respect to the axis of the reflecting tube 106.

In the distal segments 902, flexibility may be achieved by forming the distal segment 902 from a flexible material. For example, the distal segment 902 may be manufactured from a polymer coated in rubber or a thin metal sleeve coated in rubber or other flexible coating. In other embodiments, the optical therapy device 100 (such as the optical therapy device illustrated in FIG. 9E) includes pivots (not shown) on the end of each of the distal segments 902, which may be parallel. Pivots will allow for the parallel end of the optical therapy device to move or be moved independently of the linear portions of the parallel reflecting tubes 902.

Figure 9F:
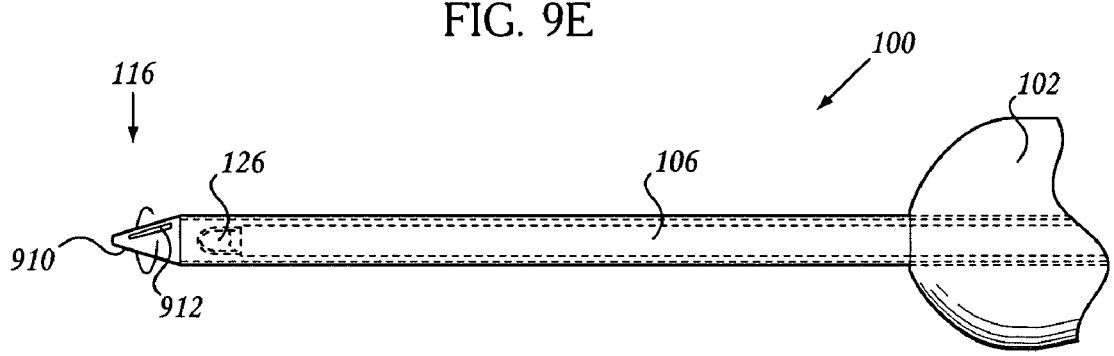

An optical therapy device 100, in accordance with another embodiment of the present invention, is illustrated in FIG. 9F. The optical therapy device 100 includes a handpiece 102 and a tube 106. At the distal end 116 of the tube 106 is a rotational member 910 mounted thereto. Rotational member includes an aperture 912 through which light energy emitted from the light source 126 may be transmitted. In one embodiment, the rotational member 910 is able to rotate about an axis parallel to the central axis of the reflecting tube 106.

In one embodiment, the rotational member 910 is shaped to focus the light from the light source 126 to the aperture 912 of the rotational member 910. The rotational member 910 is, in one embodiment, substantially non-transmissive and substantially reflects all of the light emitted by the light source 126 to the aperture 912. By rotating within the nose, the rotational member 910 is able to provide the light from the light source 126 through the aperture 912 to the soft tissue of the inside of the nose or other body cavity in a circumferential manner.

Figure 9G:
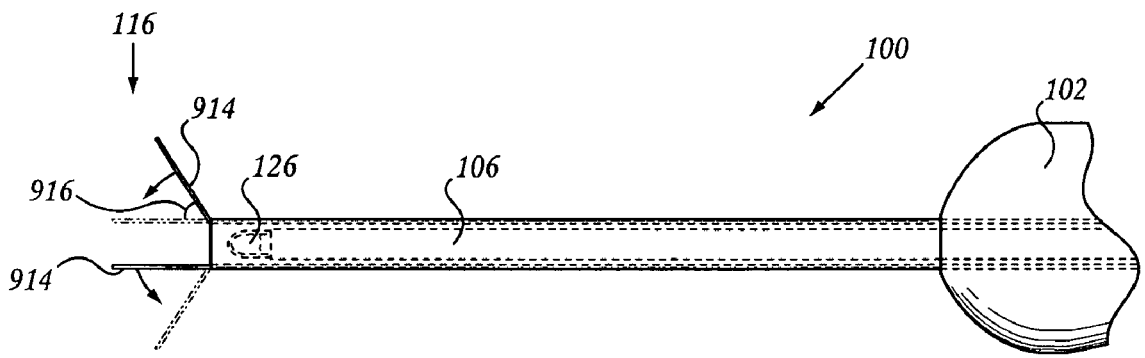

FIG. 9G illustrates another optical therapy device in accordance with yet another embodiment of the present invention. In the optical therapy device 100 of FIG. 9G, tube 106 includes light guides 114 mounted at the tube's distal end 116. Adjustable light guides 914 may be oriented at an adjustment angle 916 with respect to the tube 106.

In one embodiment, adjustment angle 916 may be adjusted between an angle of about 0 and about 60 degrees with respect to the reflecting tube 106. In another embodiment, the adjustment angle is between about 10 and 30 degrees.

The inside surface of the adjustable light guides 914 are generally reflective or covered with a reflective material so that light emitted from the light source 126 reflects off the adjustable light guides onto the tissue on the insider surface of the nose. The outside surface of the adjustable light guide is generally covered with a nonabrasive material or coating that is comfortable to a user when inserted inside or his or her nose.

Figure 9H:
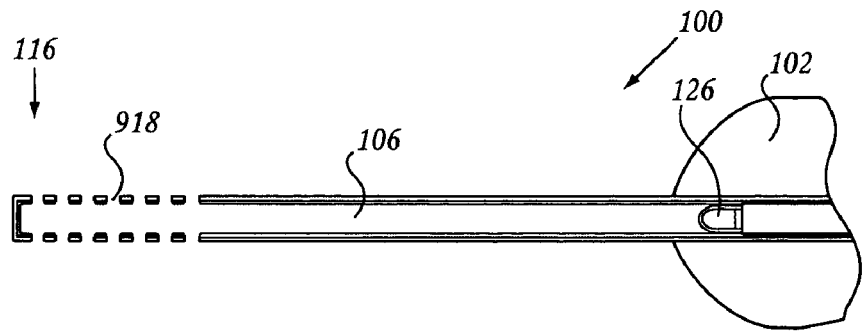

An optical therapy device 100, in accordance with yet another embodiment of the present invention, is illustrated in FIG. 9H. The optical therapy device 100 of FIG. 9H includes a handpiece 102 coupled to a tube 106. The tube 106 includes multiple apertures 916 at its distal end 116. Apertures 116 may be provided around the entire circumference of the reflecting tube 116 or may be provided on only one side or along only a selected portion of the reflecting tube 106.

The apertures 916 may be between 0.1 and 1 mm in diameter, or may be between 0.5 and 2 mm in diameter. The apertures 916 may be spaced between 0.5 to 1.0 mm, or between 1 to 3 mm from one another. In one embodiment, the distal end 116 of the tube 106 includes at least four apertures. In another embodiment, tube 106 includes between two and ten apertures. In another embodiment, tube 106 includes greater than ten apertures. Apertures 916 allow light emitted from light source 126 to escape from the insider of the tube 106 and enter the patient's nose. In this embodiment, light is emitted through the apertures 916 of the reflecting tube 106 in a longitudinal fashion (e.g., along the length of the tube) rather than at a distal end alone.

Figure 9I:
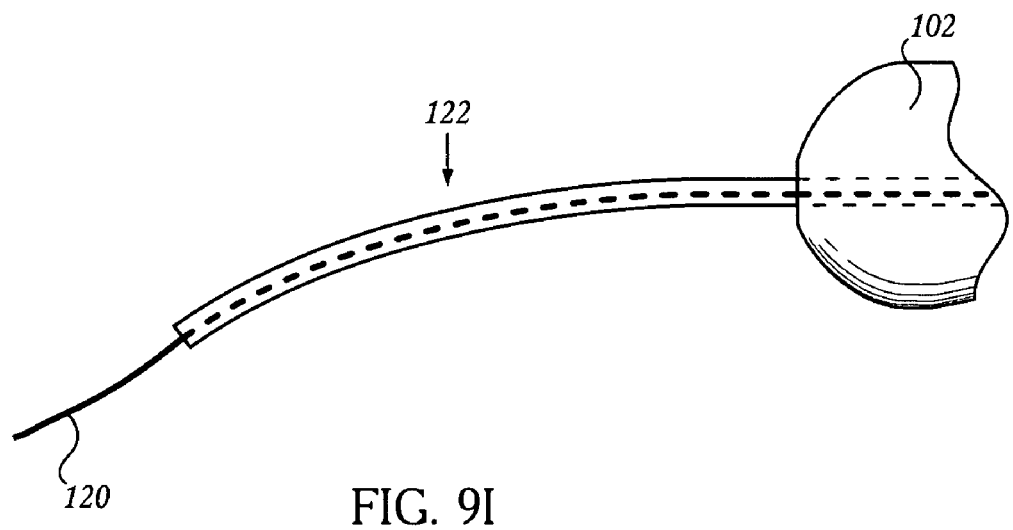
FIGS. 9I-9J illustrate another optical therapy device in accordance with another embodiment of the present invention.
Figure 9J:
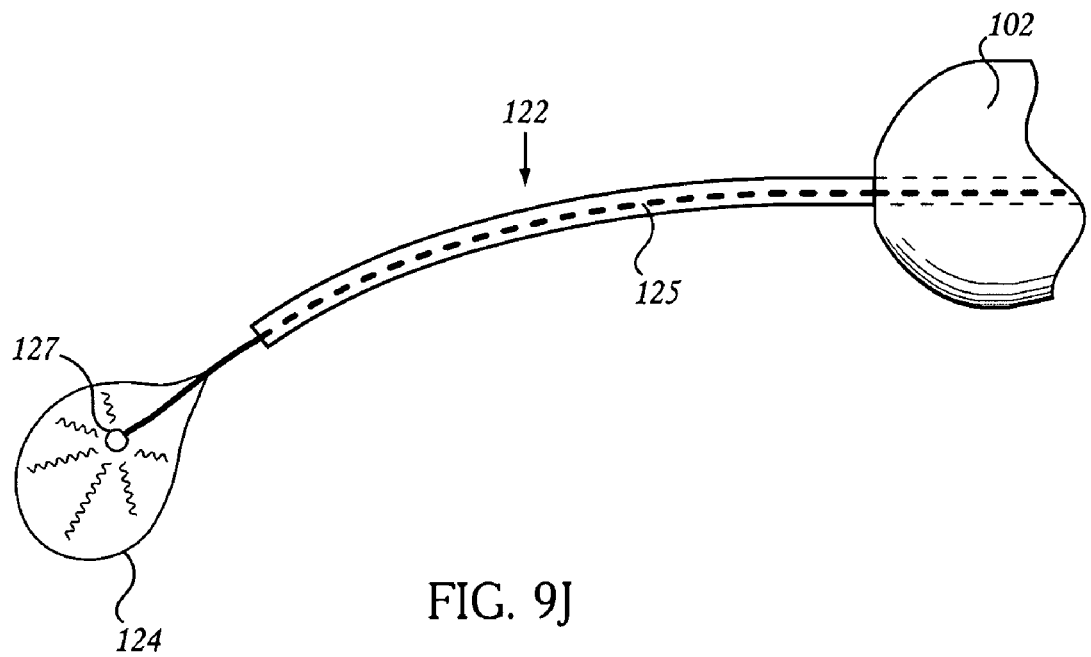

FIGS. 9I-9J illustrate additional embodiments of the present invention. Handpiece 102 is connected to a flexible component 122 which has a lumen 125 within flexible component 122. As described above and below, flexible component 122 can transmit light, can comprise the pathway to transmit electrical power, conduct heat, or can perform all three functions. Lumen 125 is sized to at least allow a second flexible device such as a guidewire 120 (well-known in the medical device arts) to pass through. The guidewire can allow for access to small orifices such as those which lead to the sinuses. After the guidewire 120 gains access to or purchase in the desired small orifice, the catheter 122 is fed over the guidewire 120. The guidewire 120 can have an expandable component 124, such as a balloon or anchor, on its end, such that the expandable component 124 can hold the guidewire 120 in the nose. The optical therapy can then be delivered through the guidewire with therapy that is generated by a light source located along the body or handpiece of the optical therapy device and delivered to the expandable component, or light can be generated in the expandable component 124. In the embodiment illustrated in FIG. 9J, a light source 127 is located at the distal end of the guidewire 120.

Figure 10A:
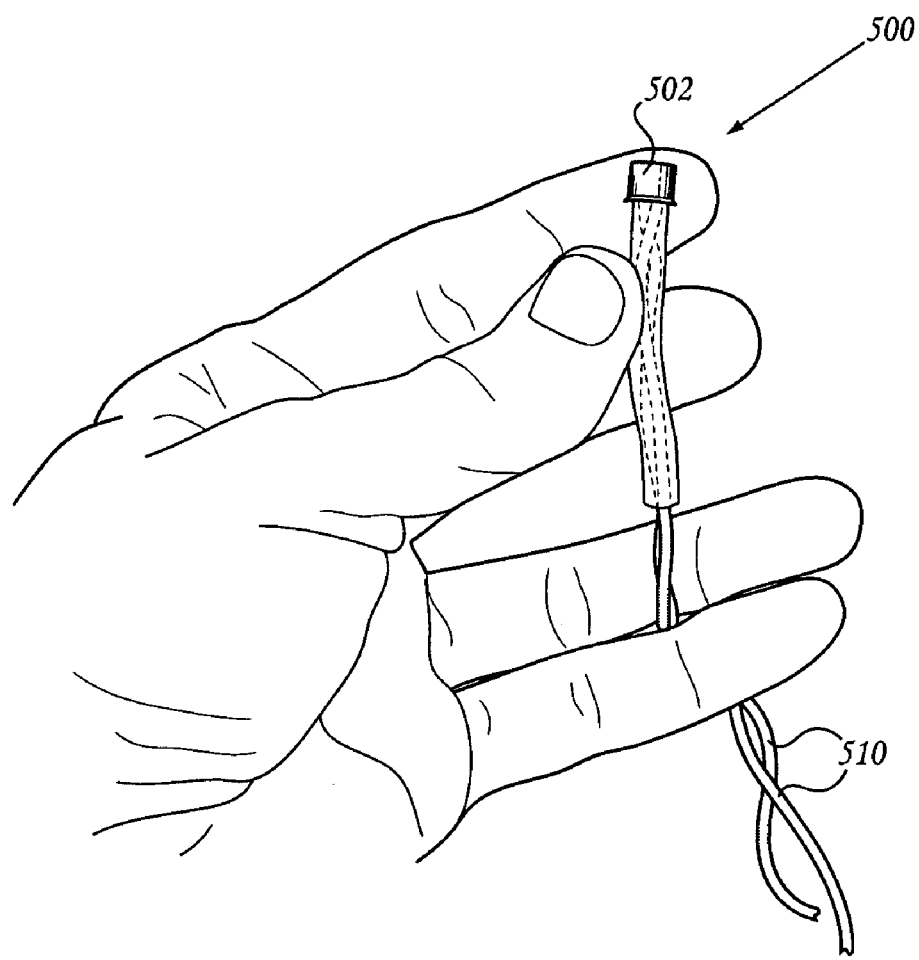
FIG. 10A illustrates a light emitting diode (LED) device in accordance with one embodiment of the present invention.

FIG. 10A illustrates a light emitting diode (LED) device 500 in accordance with one embodiment of the present invention. FIG. 10C illustrates a recording by a spectroradiometer of the optical output from an LED device 500 that emits light centered at a 308 nm wavelength peak. In the illustrated embodiment, the total output (e.g., optical power or area under the spectral output curve) at the 308 nm wavelength peak is in the range of from about 0.1 $\mu W/cm^2$ to about 500 $\mu W/cm^2$, from about 500 $\mu W/cm^2$ to about 1 $mW/cm^2$, or from about 1 $mW/cm^2$ to about 5 $mW/cm^2$.

FIG. 10A shows the size of the LED device 500 relative to an average size finger. The temperature of the LED 500 is often negligible, as it can be held in one's hand as shown without a perceptible temperature change. Embodiments of an LED package 502 are provided in FIGS. 10A and 10B. The package 502 includes its ordinary meaning and also generally refers to the structures supporting the LED chip 504, including the electrical leads 510, 511, the heat conducting element 506, and the covering optical element 508. Covering optical element 508 can accomplish a number of functions, including conditioning the light. Conditioning can include diffusing the light from the LED chip, focusing the light from the LED chip, directing the light, combining the light with a phosphor, or mixing and combining the light from multiple chips. Although one spectral peak is shown for the LED 500 of FIG. 10C, in another embodiment, the LED 500 has more than one spectral peak. For example, multiple chips (e.g., dies) may be included in the same LED package 502. In another embodiment, the multiwavelength spectrum emanates from one chip. The spectrum of one embodiment of a multi-wavelength, multi-chip LED 500 (mLED) is illustrated in FIG. 10E. The arrows of FIG. 10E point to the mLED's spectral peaks, which, in the illustrated embodiment, occur at 308 nm, 310 nm, 320 nm, and 330 nm.

The mLED device 500 appears (on the outside) the same as LED device 500 of FIG. 10A; however, on the inside of the package, 502 there may be differences in that the individual diode chips (e.g., dies) are assembled in a cluster, or chipset. Each diode chip (e.g., die) can further be driven at an independent current (e.g., 20 mA) and its duty cycle (e.g., the ratio of the on time divided by the sum of the time and the off time) can be adjusted independently. The drive current is generally directly proportional to the optical output power and the optical efficiency is substantially unchanged at low temperatures. The duty cycle variable determines the amount of optical power available from each led die. For example, LED dies typically become less efficient at higher temperature (for example, due to an increase in resistance) and will generate more heat than light per electron than they would at lower temperature. If the "on" time is a small fraction of the "off" time, then the chip has time to cool down; therefore the short burst of current during the "on" period can result in a short duration of very high power. Thus, despite the fact that the relative power at each wavelength is shown to be similar in FIG. 10E, the relative power of each die can be varied using a combination of current and duty cycle.

The total optical power provided by the LED devices 500 of FIGS. 10A-E may be in the range of between approximately 100 µW and approximately 1 mW, between about 1 mW to about 5 mW, or between about 5 mW to about 15 mW. Depending on the light conditioning structure 508, the intensity of the output can be concentrated greatly into a smaller spot size. Focused intensities can range from about 1 mW/cm$^2$ to about 1 W/cm$^2$ depending on how small the spot size is at the focal distance. The focal distance can range from 0.5 mm to 10 mm depending on the focal length of the light conditioner.

In one experiment, the device depicted in FIG. 10A was attached to the skin of a human subject. After 14 minutes, the device was removed. Within the following 12 hours, a "sunburn" was detected over an area of 1 cm$^2$ thereby demonstrating a biological effect of the ultraviolet semiconducting structures (UV LEDs).

Figure 10B:
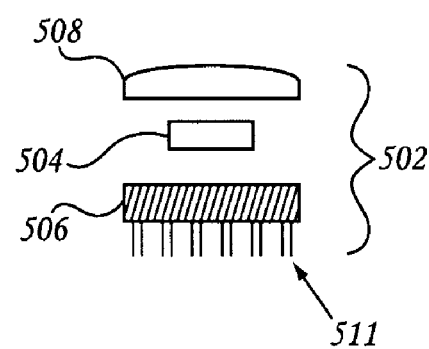
FIG. 10B is an exploded view of the LED of FIG. 10A.
Figure 10C:
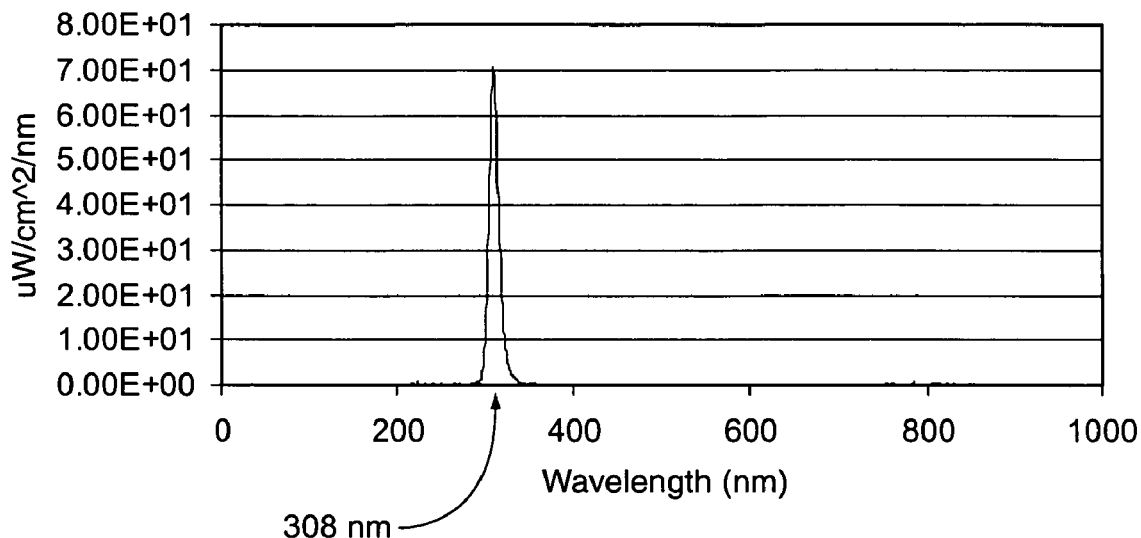
FIG. 10C illustrates a spectroradiometer measurement of the optical output from an LED device, such as the LED of FIG. 10A, having a peak at about 308 nm.

FIG. 10B illustrates a partial exploded view of the LED (or mLED) package 502 of FIG. 10A. The light emitting portion of the package includes LED chips (e.g., dies) 504 on a platform 506. The platform is also referred to as the header, submount, or combination of header and submount, and can serve as a heat dissipating module. Typical LED chips include several semiconductor layers having specific bandgap differences between them. When voltage is applied across the semiconductor, light of a particular wavelength is emitted as the current flows through the different layers of the die.

An LED chip 504 can be a cluster of multiple chips (otherwise referred to as a chipset) located on a platform 506, as shown in FIG. 10B. The platform 506 can include a heat transferring element. For example, the heat transfer element can be a ceramic heat sink and/or diffuser. Alternatively, the heat transfer module can be an active device, such as a thermo-electric cooling device. Such heat transfer modules are well known to those skilled in the art of semiconductor and LED packaging. Additional elements on the platform 506 include reflectors, which are also well known to those skilled in the art. A light conditioner in the form of a lens 508 can receive and direct light from the LED chip or chips 504 as desired. In one embodiment, the lens 508 focuses the light from the LED cluster 504. The lens 508 can be made from materials which are generally transparent to the wavelengths of interest (e.g., silicone or quartz). In another embodiment, the conditioner 508 scatters or diffuses light from the LED cluster 504. In another embodiment, the conditioner 508 contains a coating or contains particles within the material of the conditioner 508 which act as phosphors to alter the wavelength of output. In another embodiment, the conditioner 508 configures the pattern of light to generate a relatively uniform illumination pattern in an internal body cavity, such as the nasal cavity. For example, in one embodiment, the lens 508 projects light to 70% of the exposed area of a body cavity (e.g., the nasal cavity) such that the illumination is substantially uniform (for example, does not vary more than 10%-20% across the surface of the body cavity).

The LED chip or chips 504 can include about 1-5 LED chips, about 5-10 LED chips, about 11-20 chips, or greater than about 20 chips. The electrical power to each chip can be controlled independently by one or more of the leads 511 of FIG. 10B. The leads 511 can be extended and/or combined into a larger connector, leads or computer bus, 510. Furthermore, in addition to power, the duty cycle of one or more of the chips in the chipset 504 can be controlled independently and may be turned on or off at any given time. For example, the duty cycle of an individual or multitude of chips 504 (e.g., dies) can be controlled at a frequency of from about 1 Hz to about 1000 Hz, from about 1000 Hz to about 10,000 Hz, from about 10 kHz to about 1000 kHz, from about 1 MHz to about 100 MHz, from about 100 MHz to about 1 GHz, and/or from about 1 GHz to about 1000 GHz. It may be desired to have a very high frequency for its own sake and not to limit the heat generation from the chip or chips.

Thus, it is possible to integrate such packaged LED chips (e.g., mLEDs) into a medical device to perform phototherapy to treat diseases (as discussed above and below) with a defined or pre-selected set of wavelengths and power outputs from an LED package 502. The single and multichip packages 502 shown in FIG. 10B allows the light source of a medical device to be reduced in size, and to be placed inside of catheters and endoscopes to deliver phototherapy to internal organs, cavities, surfaces, and lumens. The LEDs on such internal medical devices can be any of the wavelengths from about 240 nm to well into the infrared portion of the electromagnetic spectrum, such as for example, about 1.5 micron wavelength electromagnetic energy. In addition, solid state technology, specifically LEDs, allow for abrupt changes in spectral output and illumination pattern. Standard light sources in use today offer very limited control of spectral output, illumination pattern, and on-off frequency. Furthermore, because the LED chips can be placed anywhere on platform 506, the illumination pattern (e.g., the optical power applied to specific tissue regions) can be well controlled.

Figure 10D:
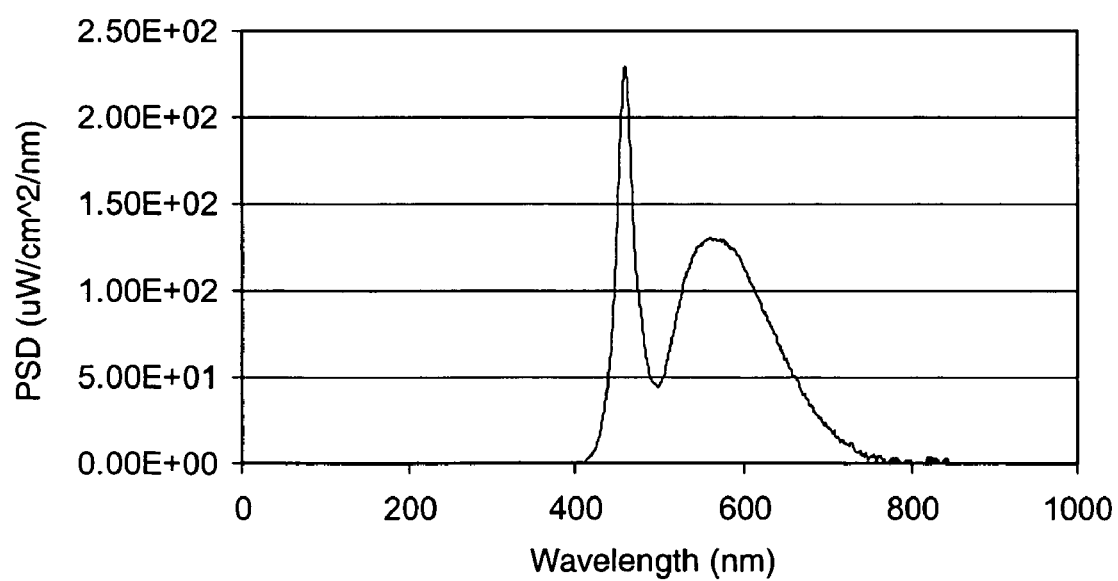
FIG. 10D illustrates the output from one embodiment of a set of three white-light emitting LEDs (wLED)
Figure 10E:
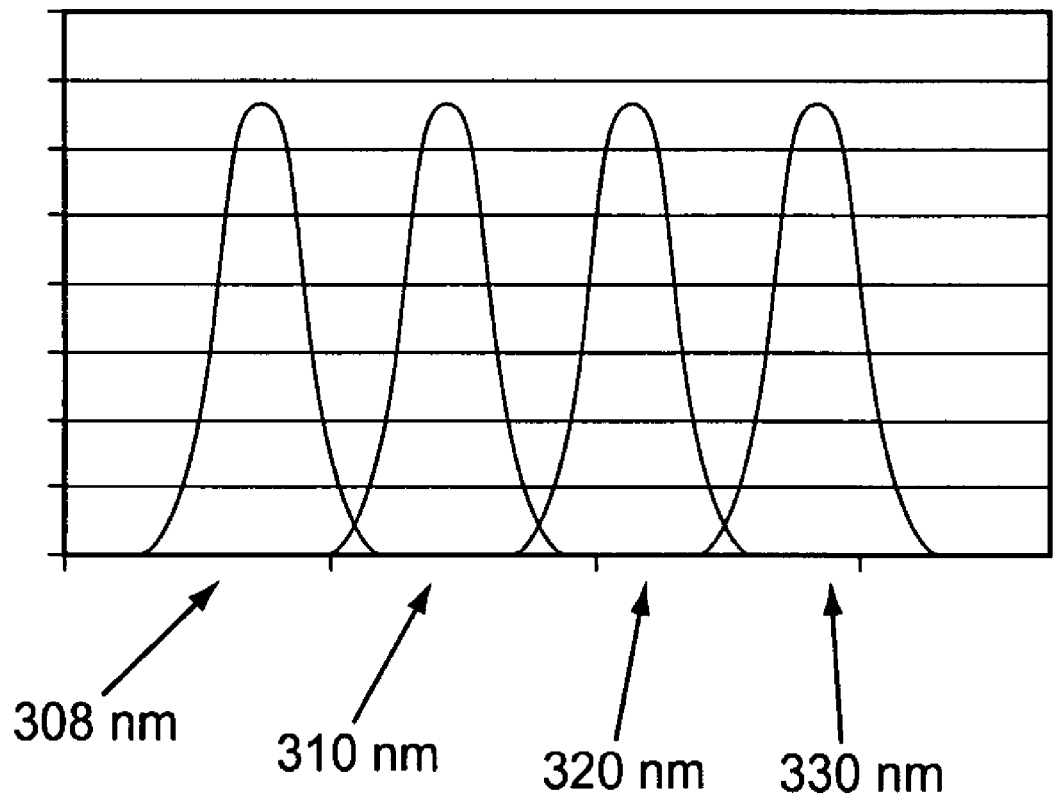
FIG. 10E illustrates a spectroradiometer measurement of the optical output from a multi-chip LED (mLED)

FIG. 10D illustrates the output from one embodiment of a set of three white-light emitting LEDs (wLED). The relatively broadband white light from these wLEDs is generated with a phosphor placed between the light emitting chips and the protective casing 508 (e.g., epoxy) overlying the chips. The total output of the wLEDs in this spectrum can be in the range of about 20 mW/cm$^2$ to about 30 mW/cm$^2$, about 10 mW/cm$^2$ to about 40 mW/cm$^2$, or about 5 mW/cm$^2$ to about 50 mW/cm$^2$.

The package size of the wLEDs may be in the range of about 3 mm to about 4 mm, about 2.5 to about 5 mm, or about 2 to about 6 mm. The size of a wLED package is often smaller than that of a uLED package. In addition, at least three fully packaged wLEDs can fit into an area of about 1-2 cm in diameter. White light may therefore be less expensive in terms of size and cost. In addition, white light is often more easily transmitted through optical guidance systems.

In other embodiments, LED chips are packaged as surface mounts (SMTs) (such as those available from Nichia Corporation, Southfield, Mich.), which may be produced in sizes as small as about 1-3 mm, about 2-5 mm, about 0.5-3.5 mm, or smaller than about 3 mm in diameter and having white light power outputs from about 1 mW to about 100 mW. Surface mounts can be placed directly in the LED package 502 (package within a larger package) shown in FIG. 10B or the surface mounts can be placed along side of another LED package 502.

In one embodiment, an ultraviolet LED, or uLED, is used without an optical guidance system. The uLED may be placed at the end of a probe that is inserted into a body cavity or is placed on or close to an external surface of a patient. The external surface of a patient includes the skin, conjunctiva, cornea, finger nails, toe nail, etc. An internal body cavity includes the nasal cavity, sinuses, tracheobronchial tree and any of the cavities mentioned above; also included, are cavities, such as the chest, and organs; such as the heart or lungs. The term probe is intended to have its ordinary meaning, and in addition can mean any device, including any of the devices 100 described herein. The probe may emit one wavelength of ultraviolet light (e.g., one narrow band, such as may be emitted by an uLED) or it can emit several wavelengths (e.g., peaks) of ultraviolet light (e.g., such as emitted by the mLED described above). The probe can also combine several wavelength peaks from the white light spectrum or it can combine a phosphor-based white light LED system as described above to produce almost any pattern of spectrum. The probe can also be used to cure adhesive compositions inside the body.

In this embodiment, the probe (and light) are brought very close to the treatment area, which has many beneficial effects in treating disease. The probe being close to the treatment area also creates a very beneficial economic effect in the sense that light therapy is generated at the point of use rather than being generated away from the point of use and then transported to the point of use. Often times, the light-transport mechanism is highly inefficient and costly. Light generation at the point of use also facilitates providing a device that is disposable after one or several uses.

FIGS. 11A-C illustrate additional embodiments of an optical therapy device 100, which may incorporate any one of or a combination of uLeds, wLEDs, and/or mLEDs as its light source 126. The probe can also incorporate LEDs with individual wavelengths in the white or infrared region of the electromagnetic spectrum. The light source 126 can be located at the distal end of a probe 106 adapted to be inserted into a patient's body. The probe 107 may be similar to or the same as the tube 106 described with respect to the various embodiments discussed above. The device 100 has a simplified structure when LEDs are used as the light source 126.

Because LEDs are efficient light generators and because they emit a relatively narrow band of light, they generate very little heat and can therefore be positioned at the distal end of the probe 107 and can be placed directly into a patient's or user's body cavity. Because of the size of the mLEDs and uLEDs and their minimal heat creation, they can be placed directly into the body cavity of interest without an optical guidance system and with minimal heat transfer requirement from the device. Thus, an optical guidance system may not be required for the ultraviolet light portion of the action spectrum of the optical therapy device 100.

Such components and designs considerably simplify the device 100 in terms of the logistics of the therapy and ultimately the cost of the device 100, particularly to the physician. The optical portion (e.g., the LED chipset) can even be placed at the end of a catheter, endoscope, or laparoscope and inserted into the body cavity of interest. In this case, the probe portion between the handle 102 and the light source 126 can be a long flexible catheter, endoscope, or laparoscope, etc. The probe portion in this embodiment is merely a structural element to allow control of the light source 126 at the distal end of the device and deliver power to the distal end of the device. The LED chipset at the end of the device 100 provides the efficient light generation relative to heat output and can minimize unwanted wavelengths in the spectrum. In some embodiments, the LEDs chipset at the end of the catheters, endoscopes, and laparoscopes deliver only white for the purpose of visualization. In other embodiments, the LEDs deliver therapeutic optical energy to a body region as discussed in many of the embodiments above.

The spectral output of the device 100 of FIGS. 11A-D is derived from combinations of the LEDs and LED packages shown in FIGS. 10A-E, which can be centered in a single narrow band (e.g., when using an uLED), a summation of distinct bands (e.g., when using a mLED), and/or combined with white light (e.g., either phosphor based or through a combination of LEDs to produce to sum to white light). Additional LED light sources 126 can also be fit into the probe 107. Depending on the ultimate size of the probe 107 and the body cavity to which it is desired to apply therapy, additional LEDs (e.g., white light LEDs with the spectral output shown in FIG. 10D) can be added to achieve combinations of ultraviolet light such as a combination of UVA, UVB, and white light as described above and in U.S. patent application Ser. Nos. 10/410,690 and 10/440,690, filed Apr. 9, 2003 and May 19, 2003, and published as U.S. Publication Nos. 2004/0204747 and 2004/0030368, respectively, which are incorporated by reference herein.

FIG. 11B illustrates one embodiment of a device 100 that incorporates white light generating LEDs 400 (as further illustrated in FIG. 11C taken along line C-C of FIG. 11B) and an ultraviolet emitting center portion 402 (as further illustrated in FIG. 11D taken along line D-D of FIG. 11B). The illustrated embodiment of FIG. 11B is similar to the uLED or the mLEDs depicted in FIGS. 10A-D. The white light is transmitted from their respective LEDs 400 (which may be surface mounted, chips, or otherwise) through an optical guidance system (as illustrated in FIG. 11D) and are directed into an annulus 404 around a uLED and/or an mLED 402. The uLEDs and/or mLEDs may not have an optical guidance system to transmit their light, for example, if they are placed at or near the distal end, including at position D-D in FIG. 11B.

It is also possible to mount the surface mounted wLEDs directly on the same chip platform as the mLEDs (e.g., at the level D-D in FIG. 11B). Although in many cases, phosphor based wLEDs are preferable, in other embodiments, the chip LEDs from the white light spectrum (e.g. blue, green, red, amber, yellow dies, etc.) are mounted directly on the chipset with the mLEDs and/or uLEDs (see above) rather than using a phosphor based white light surface mount and setting the entire surface mountable wLEDs behind the ultraviolet LEDs. Independent of the final configuration, the arrangement of light sources in FIGS. 11A-D generates an equivalent or greater amount of optical power than the larger, less efficient light sources (e.g., xenon, mercury vapor, halogen, etc.) discussed above and at a fraction of the heat output, power, and cost. A portion of the increase in efficiency may be due to the elimination of the coupling steps required for more traditional light sources (e.g., the requirement to collect the light and direct into an optical fiber). LEDs and other semiconductor technology allow for efficient and precise delivery of light to body surfaces and cavities.

Such a device is also more portable and practical for a medical practitioner or patient because the ultraviolet generating light source is directly inside the body cavity or is positioned directly on, in or adjacent the body surface. This arrangement of LEDs also can obviate the need for a complex heat transfer system within the optical therapy device or in a table top box as in U.S. patent application Ser. Nos. 10/410, 690 and 10/440,690, filed Apr. 9, 2003 and May 19, 2003, and published as U.S. Publication Nos. 2004/0204747 and 2004/0030368. Although FIG. 11B illustrates the individual sets of LED chips as being at different positions along the axis of the device 100, the surface mountable wLEDs 400 and/or all LED chips may be placed at substantially the same position along the device 100 longitudinal axis. For example, in one embodiment, the wLEDs 400 and other LED chips are placed at the distal end of the device 100.

In some embodiments, the mLEDs and uLEDs can be placed at the end of a flexible device (e.g., a catheter, endoscope, ureteroscope, hysterocope, laryngoscope, bronchoscope) to enter body cavities or body lumens and deliver ultraviolet light without guiding the light from one place to another. For example, the mLEDs and uLEDs can be placed at the end of a catheter or an endoscope to treat the lumen of an internal organ. In some embodiments, the LEDs are placed inside a balloon inside a body cavity. In these embodiments, the mLEDs can include wavelengths in the visible to infrared, or from the ultraviolet to visible, or combinations of wavelengths from the ultraviolet to the infrared.

There are any number of disease states which can be treated with devices where LEDs are placed at the point of therapeutic application and on devices which can be delivered into body cavities, surfaces, and/or lumens. One example is treatment of infected indwelling catheters and implants. For example, indwelling vascular catheters often become infected and have to be removed at a very high cost to the patients and health care system. A system of mUV LEDs or uLEDs which emit light in the wavelength range of about 250 nm to about 400 nm at the region of infection would eradicate infection within the catheters and obviate or delay the need to remove the catheters and replace them.

Figure 12A:
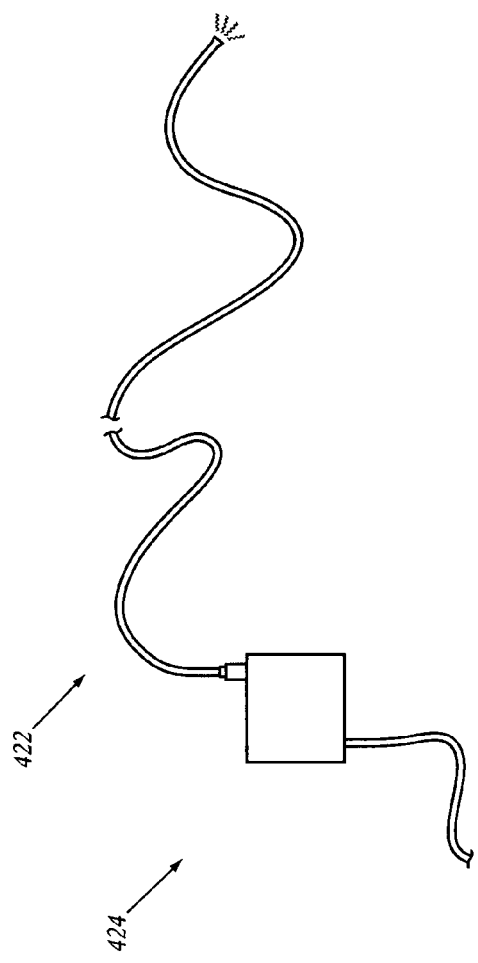
FIG. 12A illustrates another embodiment of an optical therapy device positioned at the end of a flexible medical device.
Figure 12B:
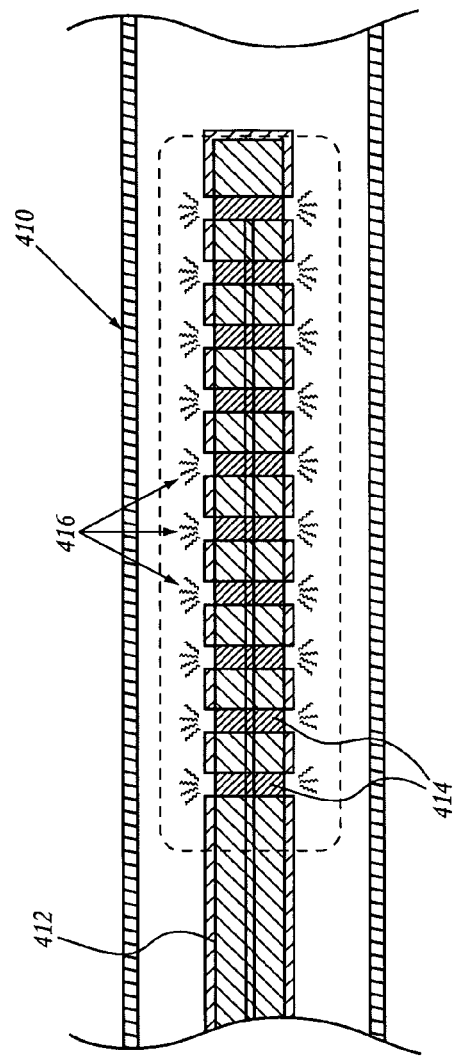
FIG. 12B illustrates one embodiment of an indwelling catheter according to another embodiment of the present invention.

FIG. 12B illustrates an indwelling catheter 410 which is used to administer parenteral nutrition (TPN) (for example) to a patient by providing venous access in a patient. Such a catheter can also be used for chronic or semi-chronic delivery of chemotherapy, for dialysis access, or for a variety of additional applications. Catheter 410 may also be used to provide chronic implants, such as those used for chronic dialysis access or other permanent vascular or nonvascular devices. A second catheter 412 is shown within the indwelling catheter 410. The second catheter 412 has a series of LEDs 414 along its length with corresponding optical windows 416 in the second catheter 412 which allow for transmission of sterilizing wavelengths. The therapy (e.g., sterilizing wavelengths) can be applied periodically (e.g., on a maintenance basis to prevent infections from occurring) or the therapy can be applied at the time of an acute infection. Although the LEDs are shown at the point of therapy in FIG. 12B, in some embodiments a light guide is used to transport light some distance prior to the point of therapy. The light guide can be a flexible fiber optic light guide with total internal reflection or the light guide can be more rigid as illustrated in several of the embodiments above. The LEDs can deliver light to the indwelling implants from any point along the light guide.

In another embodiment (not shown), an indwelling vascular graft is placed in the aorta or peripheral vessels or is used in dialysis. Similar to the case of indwelling vascular catheters, indwelling vascular conduits often become infected and lead to substantial morbidity and mortality in patients. A catheter based system to deliver ultraviolet light sterilizing therapy to treat infected indwelling grafts would be highly beneficial and may obviate or delay the need to remove these implants. Implanted vascular conduits such as dialysis grafts also become occluded secondary to a process called restenosis or intimal hyperplasia. This is a similar process to that seen in smaller vessels such as coronary arteries when a device such as a stent is placed. Because of the anti-proliferative properties of UV light (see Perree, et al., UVB-Activated Psoralen Reduces Luminal Narrowing After Balloon Dilation Because of Inhibition of Constrictive Remodeling, 75(1) Photochem. Photobiol. 68-75, which is incorporated by reference), a device carrying LEDs can be used at the region of the lesion to treat the lesion and prevent the process of restenosis or intimal hyperplasia.

Figure 12C:
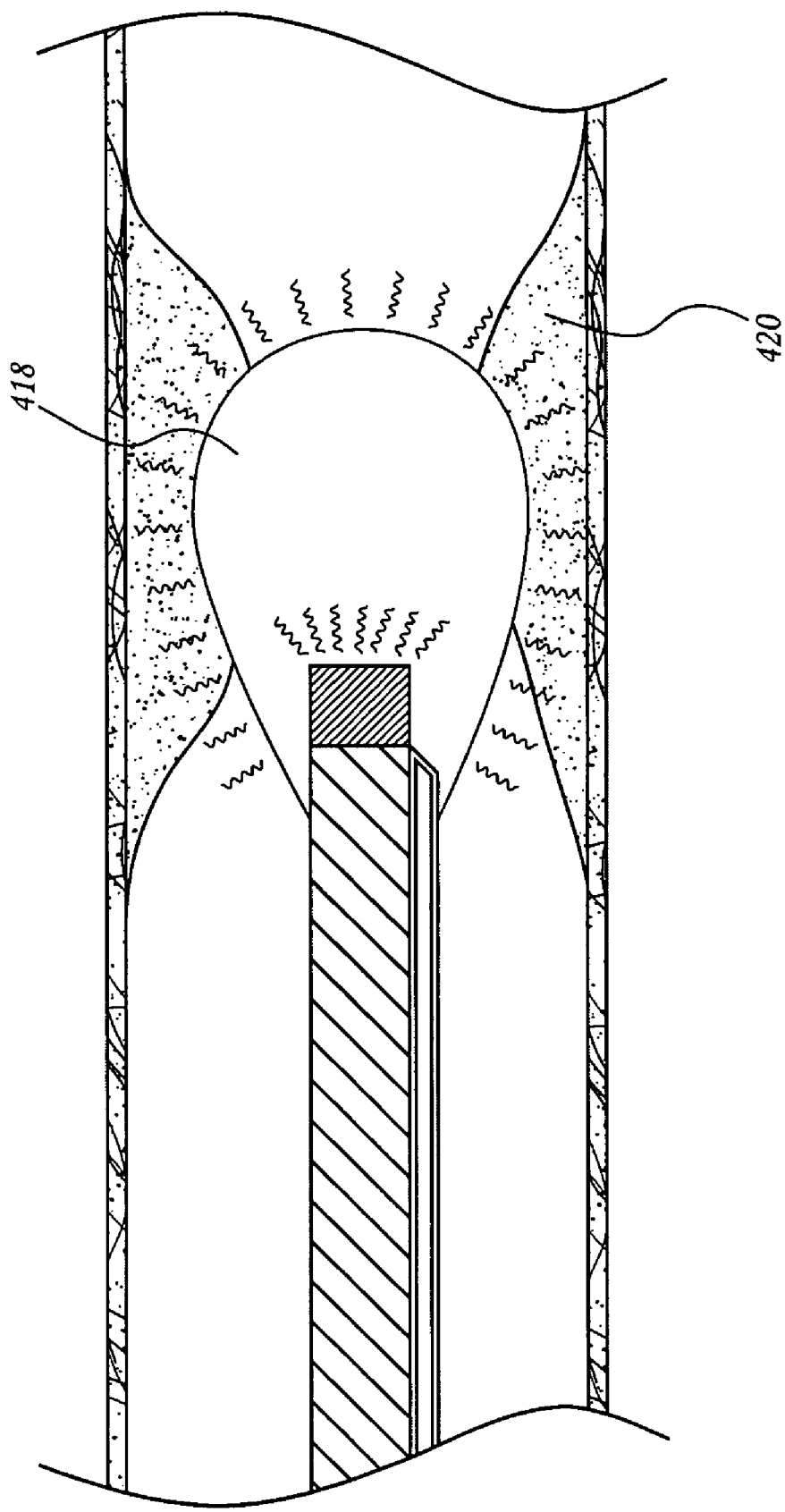
FIG. 12C illustrates one embodiment of an optical therapy device located inside of an at least partially optically-transparent balloon.

FIG. 12C depicts such a device incorporated into an optically transparent balloon 418 (e.g., a balloon that is at least partially transparent to at least some ultraviolet light wavelengths) to transmit the light directly to a lesion 420. The balloon 418 is expanded (e.g., with any of the fluids or liquids known to those of skill in the art) and the light therapy is then directly applied to the lesion 420 without interfering blood.

FIG. 12A illustrates an optical therapy device 422 at the end of a flexible medical device 424, such as an endoscope, a catheter, or handheld probe. The device 422 can be flexible, as illustrated in FIG. 12A, rigid or semi-rigid. In addition, the device 422 or any of the devices described above and below can be used in conjunction with one or more moieties or agents, such as psoralen, in a photodynamic therapy system.

Another embodiment of the present method is referred to as "internal ultraviolet therapy," and is to treat transplanted organs. Current treatment for organ rejection is hospitalization and administration of pharmaceuticals directed to the destruction of T cells. OKT3, is a monoclonal antibody directed toward CD3 positive cells, a subset of T cells. T cells orchestrate the acute and sub-acute rejection processes seen in organ rejection. Antibodies which destroy the T cells can quell the rejection process. As noted above, ultraviolet light can specifically affect T cell viability and can therefore be used to treat organ rejection.

Figure 13A:
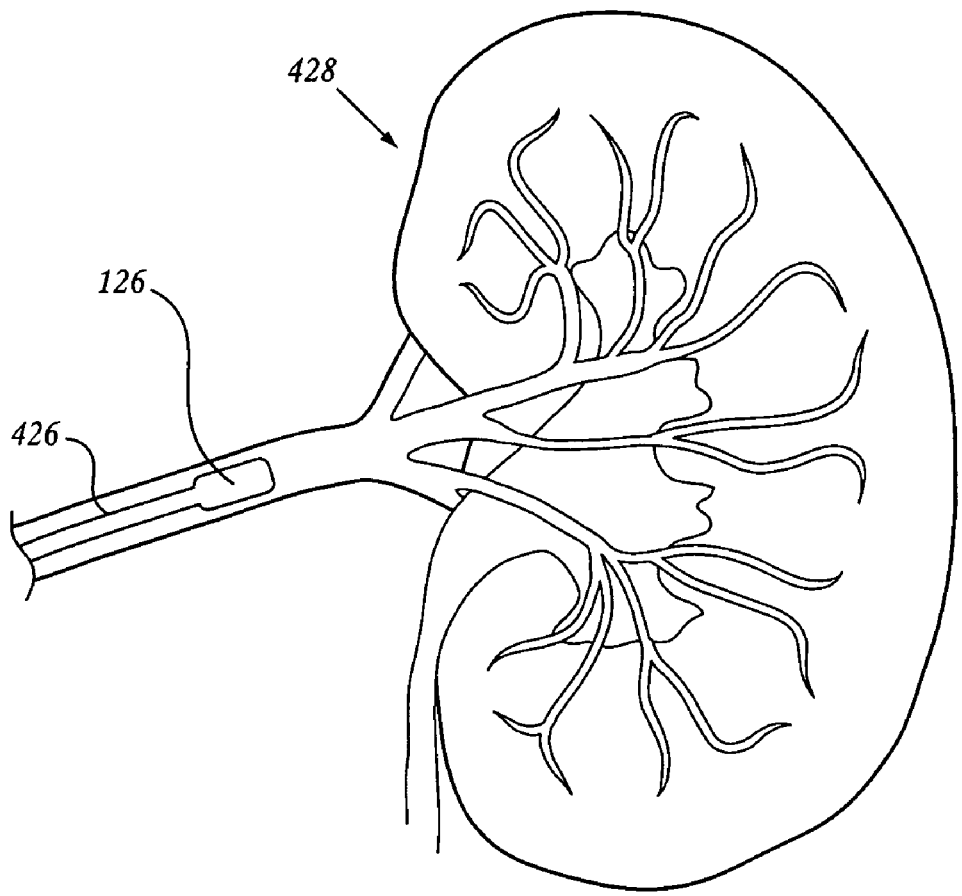
FIGS. 13A-13B illustrates one embodiment of an optical therapy system used to treat transplanted organs, such as transplanted kidney.
Figure 13B:
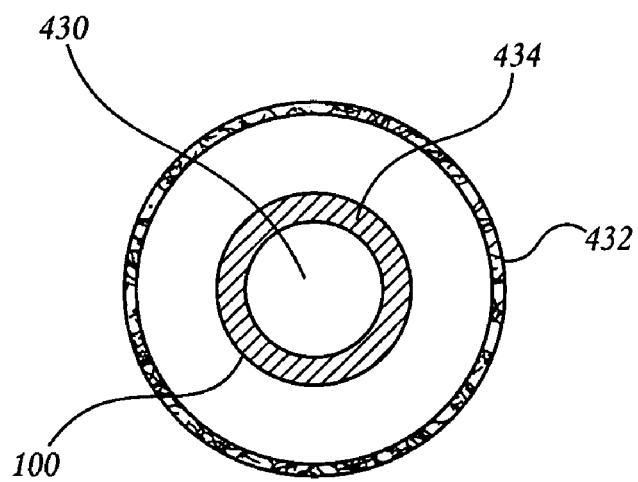

FIGS. 13A-B illustrates one embodiment of a system to treat transplanted organs that are being rejected. A catheter 426 with a light source 126, such as uLEDs or mLEDS, is placed in an artery leading to a transplanted organ 428 (in this case, a kidney). Since white blood cells travel substantially along the outer diameter of blood vessels and the red blood cells travel toward the center, ultraviolet therapy can be applied more directly and specifically to the white blood cells (T cells) by implementing the arrangement shown in FIG. 13B.

Red blood cells and platelets generally flow in the blood vessel's flow through lumen 430. The optical therapy device 100 is generally configured such that it has a lumen in its center for blood flow therethrough. The surface of the optical therapy device 100 is directed toward the outside of the vessel 432 wherein the white blood cells and the T cells flow over the surface of the device. With this device 100 positioned as illustrated in the cross-sectional view of FIG. 13B, as blood flows past the catheter 100 and along its outer circumference 434, the UV light induces T cells to undergo apoptosis. The device 100 may be placed in the artery leading to the transplant organ, or it may systemically lead to immunosuppression through placement in any vessel of a patient. In at least this respect, "optical immunosuppression" therapy may be achieved.

Figure 14A:
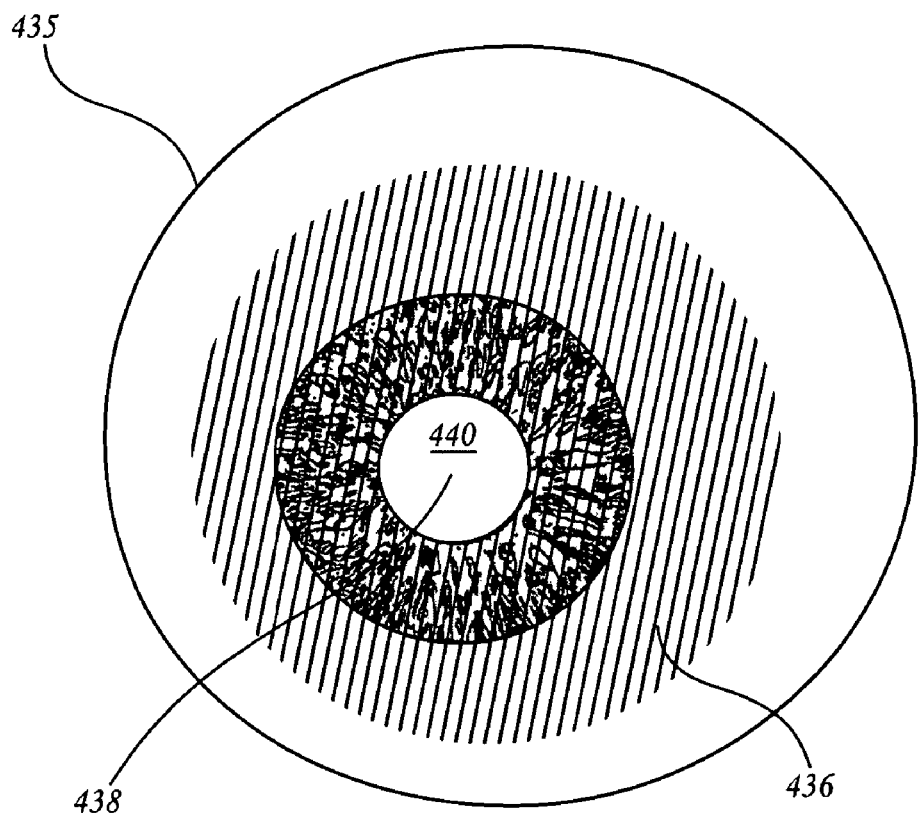
FIGS. 14A-14B illustrate another embodiment of an optical therapy device used to treat disorders of the eye.
Figure 14B:
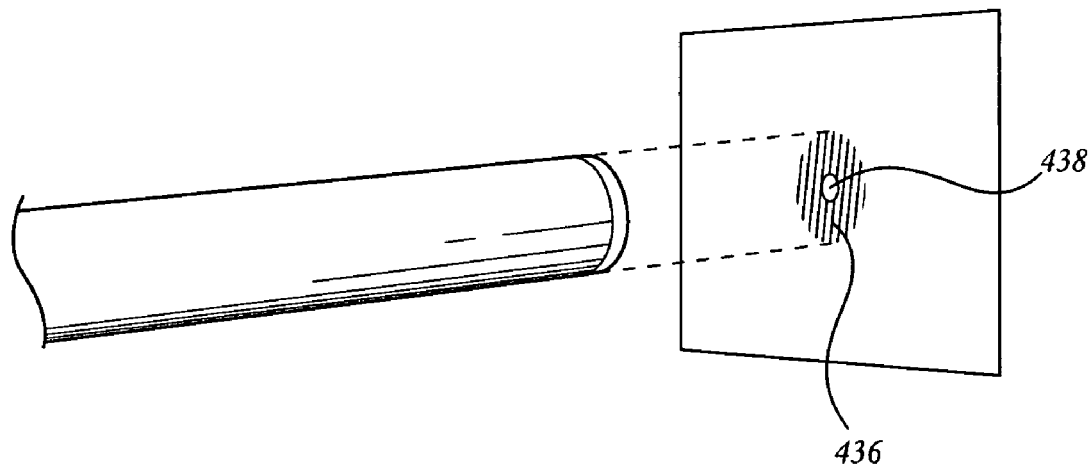

FIGS. 14A-B illustrate another embodiment of an optical therapy device used to treat disorders of the external surface of the eye (e.g., allergic conjunctivitis). Allergic conjunctivitis is a common clinical problem, and there are few therapies that are well accepted. Immunosuppressive regimens which involve tacrolimus (see, Joseph, et al., Topical Tacrolimus Ointment for Treatment of Refractory Anterior Segment Inflammatory Disorders, 24(4) Cornea 24417-20, which is incorporated by reference) has been used to treat atopic keratoconjunctivitis, chronic follicular conjunctivitis, and blepharokeratoconjunctivitis. Ultraviolet light may be used to treat allergic conjunctivitis by providing a local therapy to suppress the inflammatory response and immune reaction against the offending antigen. The optical therapy device for the eyes is generally configured to prevent ultraviolet rays from affecting the patient's lens or retina. Other disease states, including dry eyes, have also been shown to respond to immunosuppressive drugs such as cyclosporine (see Tang-Liu, et al., Ocular Pharmacokinetics and Safety of Cyclosporine, a Novel Topical Treatment for Dry Eye, 44(3) Clin Pharmacokinetics 247-61 (2005), which is incorporated by reference).

In some embodiments, the optical therapy device is used with a slit lamp to treat patients with allergies such that only the sclera 435 (see FIG. 14A-B, the portion of the eye affected by the conjunctivitis) absorbs the UV light and the lens and the retina do not. The UV is essentially focused onto an area 436 having a hole 438 or region without UV light in the center. The hole 438 in the center generally corresponds to the location of the pupil 440 and allows this region to be excluded from the optical therapy. In another embodiment, such as illustrated in FIG. 14A, a contact lens 436 is provided. In the case of the contact lens 436, a source of ultraviolet light can be used which does not have a UV sparing region in its center. In such an embodiment, the contact lens 436 creates the pattern wherein the pupil region is excluded from the ultraviolet light.

The mLEDs and uLEDs can be used for therapies such as psoriasis or other skin disorders currently treated with ultraviolet light (e.g., vitiligo, cutaneous T cell lymphoma, fungal infections, etc.). The preferred action spectrum to treat psoriasis is approximately 308-311 nm. In addition, narrow-band radiation is generally more effective than broad-band radiation. One limiting factor in current modalities and technologies for the treatment of psoriatic lesions is that typical devices available on the market today are large and expensive, and generally require patients to visit a physician's office for treatment. Home-treatment devices are typically large fluorescent lamps that are adapted to treat a broad area rather than a localized region. Whether in the home or in the office of the medical practitioner, the therapy takes time out of the patient's daily schedule. In addition, it is typically difficult for a patient to perform other tasks while the therapy is being applied. Furthermore, with current technology, it is difficult to treat a small area of the skin with narrowband light. Lasers are sometimes used to do so, but lasers are generally expensive and are not practical as home-based therapy devices.

Figure 15A:
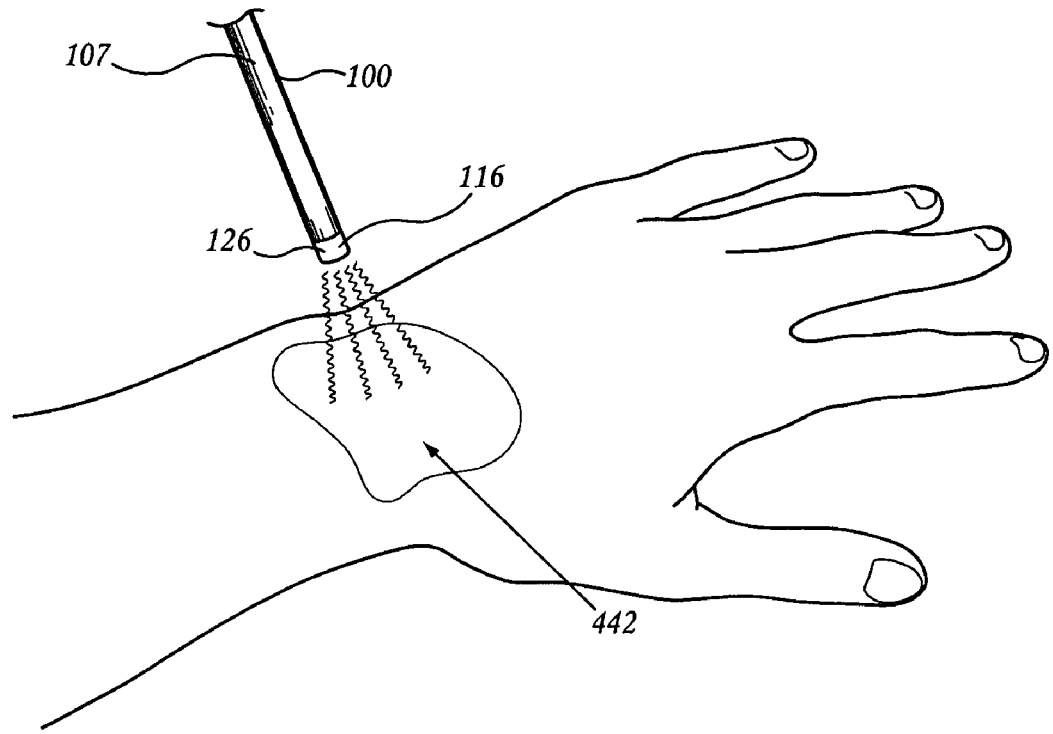
FIG. 15A illustrates an optical therapy device delivering optical therapy to a patient's skin.

FIG. 15A depicts one embodiment of the therapeutic device 100 of the current invention applied to a patient's skin 442. The optical output is similar to any or all of the devices depicted above and can be narrow-band, broad-band a combination of narrow band and broadband (for different wavelength regions), or a combination of multiple narrow-band, and/or broadband, and/or low or high power white light. The light sources are any of the light sources in any of the configurations described above. In one example, the light sources are solid state light sources which, as described above, are easily portable by the patient and are powered with a battery pack. The dose of the therapy can be set by an integrated microcontroller which is programmed by a physician before the optical therapy device is dispensed. The uLEDs, mLEDS, and/or wLEDs are used singly or in combination. In one embodiment, the LEDs are positioned at the end 116 of the probe 107. The probe can also include a tip 126 which can be purely passive (for example, a transmissive sheath) or the tip 126 can alter the light output in some way (for example, a diffusive tip). The output of the probe 107 in each spectral region can be controlled so that some LEDs are off while others are on. For example, although a mLED is placed at the end of the probe 107, if one uLED on the chipset is activated, the mLED will output only UV wavelength light.

The therapeutic device 100 can also be used in conjunction with any of a multitude of moieties as a photodynamic therapy device, as described above. The diseases of the skin which can be treated with the therapeutic device 100 include but are not limited to: vitiligo, psoriasis, atopic dermatitis, mycoses fungoides (T-cell lymphomas), skin cancers, and infections (e.g., fungal infections). The device 100 may also contain integrated photodetectors, which can continuously readjust the device's output or can detect a disease state of the skin so that the optical therapy can be applied.

Figure 15B:
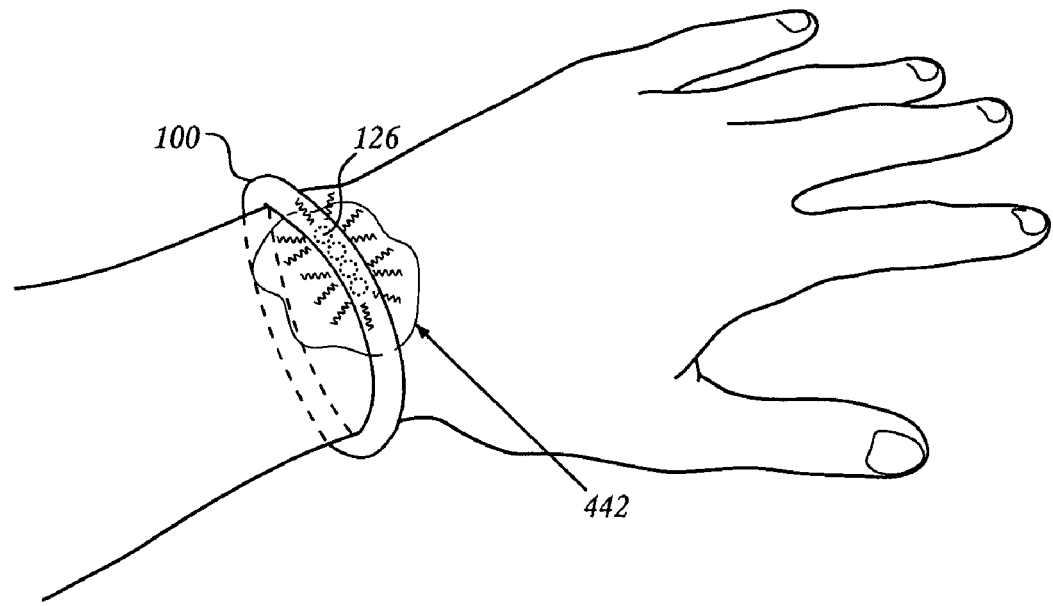
FIG. 15B illustrates a wearable optical therapy device in the form of a wrist bracelet.

FIG. 15B shows another embodiment of the therapeutic device 100 in which uLEDs, wLEDs, and/or mLEDS are incorporated into a device which can be worn or otherwise fixtured, carried or attached to a patient while the therapy to treat a skin disorder is being applied. Although the device 100 of the embodiment illustrated in FIG. 15B has the form of a bracelet, the light source 126 LEDs can be incorporated into any material which can at least partially cover or are in direct or indirect contact with the patient's skin 442. For example, the therapeutic device 100 may have the form of a bandage, blanket, any articles of clothing, a ring, jewelry, a hat, a wristband, a shirt, a sock, underwear, a scarf, a headband, a patch, a gauze pad, or any other wearable article, etc.

In another embodiment, several devices 100 (e.g., bandages) are brought together or applied to treat a larger area. In one embodiment, a kit can having different sized bandages is provided. Adhesive can be a component of the kit and/or a component of the bandages. The individual sized bandages can be fit together to fit different shaped and sized areas or plaques. With such a "wearable" device 100, a patient can treat his or her disorder (e.g., psoriasis) while performing other tasks or sleeping and can treat small or large areas of disease in a time- and cost-effective manner.

Such a localized therapy is also safer than treatments which apply light over a broad area of skin because portions of the skin which are not psoriatic can be unnecessarily exposed to ultraviolet light. With the LED systems described above, broad-band or narrow-band optical therapy can easily be applied to the skin depending upon clinical requirements. In addition, photodetectors may be integrated into the therapeutic device 100 for feedback control of the therapy. Internal body cavities can be treated as well with permanent or semi-permanent optical therapy devices 100. For example, in one embodiment, inner ear infections are treated by placing an optical therapy device 100 inside of the ear canal or a nasal or para-nasal cavity or airway such as the lungs can be treated with a permanent or semi-permanent light emitting implant. In some embodiments, an implant is surgically placed inside a body cavity or organ such as an intra-abdominal organ or an intra-thoracic organ. Implants can also be placed in a genitourinary system such as the bladder, uterus, or vagina to treat infectious, allergic, and/or inflammatory diseases. An implant can also be used for contraception. The implant can be powered by directly contacting the implant with a power source or through an external power source coupled via electromagnetic coupling.

Figure 15C:
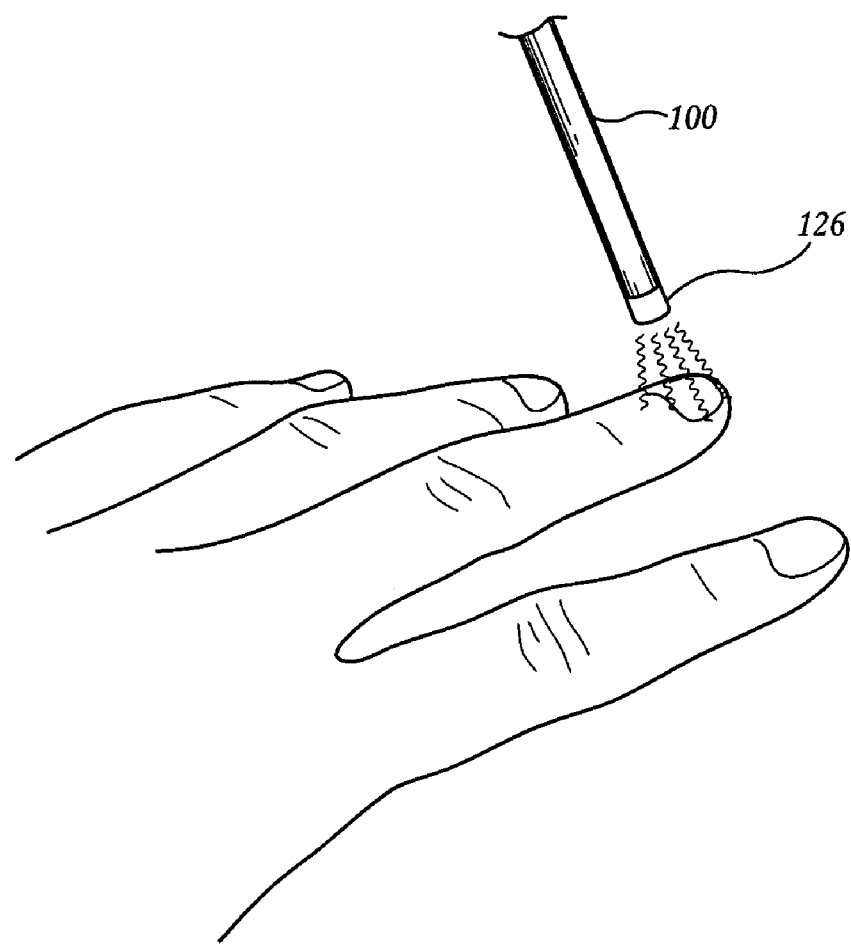
FIG. 15C illustrates an optical therapy device delivering optical therapy to a patient's fingernail.
Figure 15D:
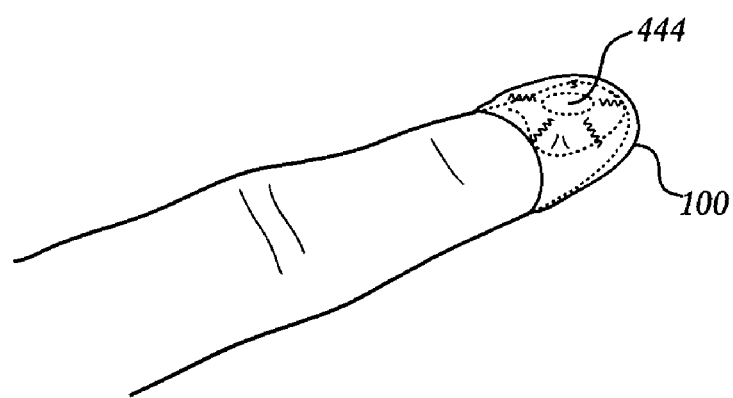
FIG. 15D illustrates an optical therapy device in the form of an adhesive bandage.

FIG. 15C illustrates an optical therapy device 100 being applied to a finger or toe nail. In such a case, tinea infections of the nails may be treated with the device by choosing the appropriate sterilization wavelengths (e.g., 255-320 nm) for the uLEDs and mLEDs. FIG. 15D illustrates an optical therapy device 100 used to treat fungal infection of the nail beds 444. The optical therapy device 100 has the form of a bandage or band-aid. Such a device 100 allows patients to go about their daily lives while the treatment is being applied.

Any of the above devices can be further applied to polymer curing applications internally or externally to a patient. The devices can also be used in any context with phosphors which change the effective wavelength of light. The devices can also be used as the light activating component of a photodynamic therapy, which also changes the effective wavelength desired by the optical device.

Any of the above devices can also be used in spectroscopic applications where light (specific wavelength and/or on-off frequency) is applied to a tissue and then an optical parameter from the tissue is measured in response to the light application. The sensor to detect the optical parameter can be incorporated into the optical therapy device or can be a separate instrument.

Although this invention has been disclosed in the context of a certain preferred embodiment, it will be understood by those skilled in the art that the present invention extends beyond the specifically disclosed embodiment to other alternative embodiments and/or uses of the invention and obvious modifications and equivalents thereof. In particular, while the present optical therapy devices, systems and methods have been described in the context of a particularly preferred embodiment, the skilled artisan will appreciate, in view of the present disclosure, that certain advantages, features and aspects of optical therapy devices, systems and methods may be realized in a variety of other combinations and embodiments. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. An optical therapy device for providing therapeutic light to a nasal cavity of a person, the optical therapy device comprising:
a body, wherein at least a distal end of the body is configured to be inserted into the nasal cavity and wherein the body is further configured to be hand-held; and
multiple light sources positioned in or on said body, wherein the multiple light sources comprise:
a first light source capable of emitting optical energy comprising between about 15 percent and about 35 percent of the optical energy provided by the optical therapy device as light in the UVA region of the UV spectrum;
a second light source capable of emitting between about 1 percent and about 11 percent of the optical energy provided by the optical therapy device as light in the UVB region of the UV spectrum; and
a third light source capable of emitting between about 60 percent and about 90 percent of the optical energy provided by the optical therapy device as light in the visible region of the optical spectrum;
wherein said device is configured for the at least multiple light sources to be able to emit a dose of UV light toward tissue in the nasal cavity when the distal end of the body is positioned in the nasal cavity.

2. The optical therapy device of claim 1, wherein the multiple light sources comprise a solid-state light source.

3. The optical therapy device of claim 1, wherein the body further comprises a microcontroller electrically coupled to the multiple light sources.

4. The optical therapy device of claim 1, wherein the multiple light sources each comprise a light emitting diode.

5. The optical therapy device of claim 1, further comprising a light conditioner.

6. The optical therapy device of claim 5, wherein the light conditioner comprises a light scattering medium.

7. The optical therapy device of claim 5, wherein said light conditioner comprises a light focusing element.

8. The optical therapy device of claim 5, wherein said light conditioner comprises a lens.

9. The optical therapy device of claim 5, wherein said light conditioner comprises a light reflecting element.

10. The optical therapy device of claim 5, wherein said light conditioner comprises a mirror.

11. The optical therapy device of claim 5, wherein said light conditioner comprises a filter.

12. The optical therapy device of claim 11, wherein said filter comprises an optical filter.

13. The optical therapy device of claim 5, wherein said light conditioner comprises a sheath.

14. The optical therapy device of claim 1, wherein the multiple light sources are located at the distal end of the body.

15. The optical therapy device of claim 14, wherein the body is elongate and has a length extending from a proximal end of the body to the distal end, and the length is less than or equal to about 30 cm.

16. The optical therapy device of claim 14, further comprising a cooling module to dissipate heat generated by said multiple light sources.

17. The optical therapy device of claim 16, wherein said cooling module comprises a heat pipe.

18. The optical therapy device of claim 16, wherein said cooling module comprises an active cooling device.

19. The optical therapy device of claim 1, wherein said body further comprises a body proximal portion and a body distal portion, the body distal portion comprising the distal end of the body, and wherein the multiple light sources are located at the body proximal portion.

20. The optical therapy device of claim 1, wherein said body further comprises a body proximal portion and a body distal portion, the body distal portion comprising the distal end of the body, and wherein said optical therapy device further comprises a window, wherein the window is located at or near the body distal portion.

21. The optical therapy device of claim 20, wherein the window is at least partially transmissive of UV light generated by the UV light source.

22. The optical therapy device of claim 1, further comprising a sheath, wherein the sheath is configured to at least partially cover the body.

23. The optical therapy device of claim 22, wherein said sheath comprises at least one material that is at least partially transmissive of UV light.

24. The optical therapy device of claim 23, wherein said at least one material conditions said light.

25. The optical therapy device of claim 1, further comprising a controller, wherein said controller controls a parameter of the dose.

26. The optical therapy device of claim 25, wherein said controller is in or on said body.

27. The optical therapy device of claim 25, wherein the controller is programmed and comprises a timer so that only a pre-specified amount of light can be provided by the optical therapy device at any given time.

28. The optical therapy device of claim 27, wherein the parameter comprises a sequence for activating said multiple light sources.

29. The optical therapy device of claim 27, wherein said controller can record a total number of doses, and wherein said controller can prevent the emission of the dose after the total number of doses reaches a predetermined level.

30. The optical therapy device of claim 1, further comprising a power supply for powering said multiple light sources, wherein said power supply is positioned in or on the body.

* * * * *